United States Patent
Ishiwatari et al.

(10) Patent No.: US 9,222,944 B2
(45) Date of Patent: Dec. 29, 2015

(54) METHOD FOR SCREENING A SALTY TASTE MODULATING SUBSTANCE

(75) Inventors: Yutaka Ishiwatari, Kawasaki (JP); Yuko Kai, Kawasaki (JP); Takami Maekawa, Kawasaki (JP); Yuzuru Eto, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 168 days.

(21) Appl. No.: 13/190,885

(22) Filed: Jul. 26, 2011

(65) Prior Publication Data
US 2012/0028263 A1 Feb. 2, 2012

Related U.S. Application Data

(63) Continuation of application No. PCT/JP2010/066962, filed on Sep. 29, 2010.

(30) Foreign Application Priority Data

Sep. 29, 2009 (JP) .................... 2009-224942

(51) Int. Cl.
*C12Q 1/68* (2006.01)
*G01N 33/68* (2006.01)
*G01N 33/50* (2006.01)

(52) U.S. Cl.
CPC ........ *G01N 33/6872* (2013.01); *G01N 33/5008* (2013.01)

(58) Field of Classification Search
USPC ................................... 435/7.1, 29
See application file for complete search history.

(56) References Cited

U.S. PATENT DOCUMENTS

| | | | |
|---|---|---|---|
| 5,145,707 A | 9/1992 | Lee | |
| 2003/0099760 A1 | 5/2003 | Okai | |
| 2006/0223117 A1* | 10/2006 | Moyer et al. | ............ 435/7.1 |
| 2008/0153120 A1 | 6/2008 | LeCoutre et al. | |
| 2008/0261824 A1 | 10/2008 | Moyer et al. | |
| 2009/0075320 A1 | 3/2009 | Bos et al. | |
| 2009/0155408 A1 | 6/2009 | Dupuy-Cornuaille et al. | |

FOREIGN PATENT DOCUMENTS

| | | |
|---|---|---|
| GB | 2 372 503 A | 8/2002 |
| JP | 1-281054 | 11/1989 |
| JP | 02-131552 | 5/1990 |
| JP | 4-262758 | 9/1992 |
| JP | 11-187841 | 7/1999 |
| JP | 2002-510790 A | 4/2002 |
| JP | 2003-144088 | 5/2003 |
| JP | 2003-530098 A | 10/2003 |
| JP | 2007-108949 A | 4/2007 |
| JP | 2008-529987 | 8/2008 |
| JP | 2008-289426 | 12/2008 |
| WO | WO 99/51777 | 10/1999 |
| WO | WO 01/77676 | 10/2001 |
| WO | WO 2007/132123 | 11/2007 |
| WO | WO 2007/146120 | 12/2007 |
| WO | WO 2008/009565 | 1/2008 |

OTHER PUBLICATIONS

Witkowski et al.; Conversion of beta-ketoacyl synthase to a malonyl decarboxylase by replacement of the active site cysteine with glutamine; Biochemistry 38:11643-11650, 1999.*
Seffernick et al.; Melanine deaminase and atrazine chlorohydrolase: 98 percent identical but functionally different; J. Bacteriol. 183(8):2405-2410, 2001.*
Branden et al. (Introduction to Protein Structure, Garland Publishing Inc., New York, p. 247, (1991).*
Chen et a.; Characteristics of Action Potentials and Their Underlying Outward Currents in Rat Taste Receptor Cells; Journal of neurophysiology; vol. 75, No. 2, pp. 820-831, published Feb. 1996.*
Cai et al.; Multiple Modes of A-Type Potassium Current Regulation; Current Pharmaceutical Design, (2007), vol. 13, pp. 3178-3184.*
Human KCNC2 transcript variant 3; *Homo sapiens* potassium voltage-gated channel, Shaw-related subfamily, member 2 (KCNC2), transcript variant 3, accession No. NM_153748, updated Feb. 10, 2008.*
Jayaram Chandrashekar, et al., "The receptors and cells for mammalian taste", Nature, vol. 444, Nov. 2006, pp. 288-294.
Alexander A. Bachmanov, et al., "Taste Receptor Genes", Annu. Rev. Nutr., vol. 27, 2007, pp. 389-414.
John A. D Esimone, et al., "Analysis of amiloride inhibition of chorda tympani taste response of rat to NaCl", Am. J. Physiol. Regulatory Integrative Comp. Physiol., vol. 249, 1985, pp. 52-61.
"Reducing Salt Intake in Populations—Report of a Who Forum and Technical Meeting", http://www.who.int/dietphysicalactivity/reducingsalt/en/, Oct. 5-7, 2006, 61 pages.
William E. Riha, et al., "Salty taste enhancement with amino acids", Chem. Senses, vol. 22, 1997, p. 778.
Nelsa Estrella, et al., "The Effect of pH on Arginine Enhancement of Salty Taste", Chem. Sense, vol. 34, 2009, pp. A117-A118.
Bernardo Rudy, et al., "Kv3 channels: voltage-gated K+ channels designed for high-frequency repetitive firing", Trends in Neurosciences, vol. 24, No. 9, Sep. 2001, pp. 517-526.
George A. Gutman, et al., "International Union of Pharmacology. LIII. Nomenclature and Molecular Relationships of Voltage-Gated Potassium Channels", Pharmacological Reviews, vol. 57, No. 4, 2005, pp. 473-508.
T. McCormack, et al., "Molecular cloning of a member of a third class of Shaker-family K+ channel genes in mammals", Proc. Natl. Acad. Sci. USA, vol. 87, Jul. 1990, pp. 5227-5231.
R. Hernandez-Pineda, et al., "Kv3.1-Kv3.2 Channels Underlie a High-Voltage-Activating Component of the Delayed Rectifier K+ Current in Projecting Neurons From the *Globus pallidus*", J. Neurophysiol., vol. 82, 1999, pp. 1512-1528.

(Continued)

*Primary Examiner* — Antonio Galisteo Gonzalez
(74) *Attorney, Agent, or Firm* — Oblon, McClelland, Maier & Neustadt, L.L.P.

(57) ABSTRACT

By contacting a test substance with a cell that expresses a Kv3.2 protein, and comparing observed cation influx into the cell with cation influx into the cell observed when the test substance is not contacted with the cell, a salty taste modulating substance such as salt alternative compound, or salt perception enhancing or inhibiting compound is screened.

15 Claims, 3 Drawing Sheets

(56) References Cited

OTHER PUBLICATIONS

Michael Madeja, et al., "Sensitivity of native and cloned hippocampal delayed-rectifier potassium channels to verapamil", Neuropharmacology, vol. 39, 2000, pp. 202-210.

Frauke Stahler, et al., "A Role of the Epithelial Sodium Channel in Human Salt Taste Transduction?" Chemosensory Perception, vol. 1, 2008, pp. 78-90.

English translation of Written Opinion of the International Searching Authority issued Nov. 2, 2010 in patent application No. PCT/JP2010/066962 filed Sep. 29, 2010.

L. Liu, et al., "Expression and Characterization of Delayed Rectifying K+ Channels in Anterior Rat Taste Buds", Am J. Physiol Cell Physiol, 2005, vol. 289, pp. C868-C880.

T. Katsumata, et al., "Effect of Maillard Reacted Peptides on Human Salt Tast and the Amiloride-Insensitive Salt Taste Receptor (TRPV1t)", Chem. Senses, 2008, vol. 33, pp. 665-680.

V. Lyall, et al., "Regulation of the Benzamil-Insensitive salt Taste Receptor by Intracellular $Ca^{2+}$, Protein Kinase C, and Calcineurin", J. Neurophysiol, 2009, vol. 102, pp. 1591-1605.

R. Strausberge, et al., "*Mus musculus* Potassium Voltage Gated Channel", Shaw-Related Subfamily, Member 2, mRNA (cDNA clone MGC: 143909 Image: 40094886), Database GenBank, [Online], Jun. 29, 2006, Accession No. BC116289.

P. Carninci, et al., "*Mus musculus* Adult Male Corpora Quadrigemina cDNA", Riken Full-Length Enriched Library, Clone: B230117107 Product: Voltage-Gated Potassium Channel Protein KV3.2 (KSHIIIA) Homolog [*Rattus norvegicus*], Full Insert Sequence,Database GenBank, [Online], Dec. 5, 2002, Accession No. AK045425.

T. McCormack, et al., "Rat $K^+$ Channel Protein (KShIIIA) mRNA, Complete cds",Database GenBank, [Online], Apr. 27, 1993, Accession No. M34052 M69011.

O. Pongs, et al., "R. Rattus mRNA for Potassium Channel Protein (3120 bp)", Database GenBank, [Online], Jan. 14, 1993, Accession No. X62839.

Extended European Search Report issued Oct. 17, 2012, in European Patent Application No. 10820590.7.

Timothy A. Gilbertson, et al., "Fatty acid responses in taste cells from obesity-prone and -resistant rats", Physiology & Behavior, vol. 86, No. 5, XP-027726181, Dec. 15, 2005, pp. 681-690.

P. Hevezi, et al., "Genome-Wide Analysis of Gee Expression in Primate Taste Buds Reveals Links to Diverse Processes", PLoS One, Jul. 2009, vol. 4, Issue 7, pp. 1-13.

Japanese Office Action issued May 22, 2012 in patent application No. 2011-534279 with partial English translation.

Juri Iida, et al., "Analysis of Transcriptional Network", Protein Nucleic Acid Enzyme, vol. 49, No. 17, 2004, pp. 2717-2722 with partial English translation.

\* cited by examiner

SEQUENCE LISTING

```
<160> NUMBER OF SEQ ID NOS: 53

<210> SEQ ID NO 1
<211> LENGTH: 1842
<212> TYPE: DNA
<213> ORGANISM: Homo sapiens
<220> FEATURE:
<221> NAME/KEY: CDS
<222> LOCATION: (1)..(1839)

<400> SEQUENCE: 1 atg ggc aag atc gag aac aac gag agg gtg atc ctc aat gtc ggg ggc        48
Met Gly Lys Ile Glu Asn Asn Glu Arg Val Ile Leu Asn Val Gly Gly
1               5                   10                  15 acc cgg cac gaa acc tac cgc agc acc ctc aag acc ctg cct gga aca        96
Thr Arg His Glu Thr Tyr Arg Ser Thr Leu Lys Thr Leu Pro Gly Thr
                20                  25                  30 cgc ctg gcc ctt ctt gcc tcc tcc gag ccc cca ggc gac tgc ttg acc       144
Arg Leu Ala Leu Leu Ala Ser Ser Glu Pro Pro Gly Asp Cys Leu Thr
            35                  40                  45 acg gcg ggc gac aag ctg cag ccg tcg cct cca ctg tcg ccg ccg             192
Thr Ala Gly Asp Lys Leu Gln Pro Ser Pro Pro Leu Ser Pro Pro
        50                  55                  60 ccg aga gcg ccc ccg ctg tcc ccc ggg cca ggc ggc tgc ttc gag ggc       240
Pro Arg Ala Pro Pro Leu Ser Pro Gly Pro Gly Gly Cys Phe Glu Gly
65                  70                  75                  80 ggc gcg ggc aac tgc agt tcc cgc ggc ggc agg gcc agc gac cat ccc       288
Gly Ala Gly Asn Cys Ser Ser Arg Gly Gly Arg Ala Ser Asp His Pro
                85                  90                  95 ggt ggc ggc cgc gag ttc ttc ttc gac cgg cac ccg ggc gtc ttc gcc       336
Gly Gly Gly Arg Glu Phe Phe Phe Asp Arg His Pro Gly Val Phe Ala
            100                 105                 110 tat gtg ctc aat tac tac cgc acc ggc aag ctg cac tgc ccc gca gac       384
Tyr Val Leu Asn Tyr Tyr Arg Thr Gly Lys Leu His Cys Pro Ala Asp
        115                 120                 125 gtg tgc ggg ccg ctc ttc gag gag gag ctg gcc ttc tgg ggc atc gac       432
Val Cys Gly Pro Leu Phe Glu Glu Glu Leu Ala Phe Trp Gly Ile Asp
    130                 135                 140 gag acc gac gtg gag ccc tgc tgc tgg atg acc tac cgg cag cac cgc       480
Glu Thr Asp Val Glu Pro Cys Cys Trp Met Thr Tyr Arg Gln His Arg
145                 150                 155                 160 gac gcc gag gag gcg ctg gac atc ttc gag acc ccc gac ctc att ggc       528
Asp Ala Glu Glu Ala Leu Asp Ile Phe Glu Thr Pro Asp Leu Ile Gly
                165                 170                 175 ggc gac ccc ggc gac gac gag gac ctg gcg gcc aag agg ctg ggc atc       576
Gly Asp Pro Gly Asp Asp Glu Asp Leu Ala Ala Lys Arg Leu Gly Ile
            180                 185                 190
```

-continued

| | | | | | | | | | | | | | | | | |
|---|---|---|---|---|---|---|---|---|---|---|---|---|---|---|---|---|
| gag | gac | gcg | gcg | ggg | ctc | ggg | ggc | ccc | gac | ggc | aaa | tct | ggc | cgc | tgg | 624 |
| Glu | Asp | Ala | Ala | Gly | Leu | Gly | Gly | Pro | Asp | Gly | Lys | Ser | Gly | Arg | Trp | |
| | | | 195 | | | | 200 | | | | 205 | | | | | |
| agg | agg | ctg | cag | ccc | cgc | atg | tgg | gcc | ctc | ttc | gaa | gac | ccc | tac | tcg | 672 |
| Arg | Arg | Leu | Gln | Pro | Arg | Met | Trp | Ala | Leu | Phe | Glu | Asp | Pro | Tyr | Ser | |
| 210 | | | | | 215 | | | | | 220 | | | | | | |
| tcc | aga | gcc | gcc | agg | ttt | att | gct | ttt | gct | tct | tta | ttc | ttc | atc | ctg | 720 |
| Ser | Arg | Ala | Ala | Arg | Phe | Ile | Ala | Phe | Ala | Ser | Leu | Phe | Phe | Ile | Leu | |
| 225 | | | | 230 | | | | | 235 | | | | | 240 | | |
| gtt | tca | att | aca | act | ttt | tgc | ctg | gaa | aca | cat | gaa | gct | ttc | aat | att | 768 |
| Val | Ser | Ile | Thr | Thr | Phe | Cys | Leu | Glu | Thr | His | Glu | Ala | Phe | Asn | Ile | |
| | | | | 245 | | | | | 250 | | | | | 255 | | |
| gtt | aaa | aac | aag | aca | gaa | cca | gtc | atc | aat | ggc | aca | agt | gtt | gtt | cta | 816 |
| Val | Lys | Asn | Lys | Thr | Glu | Pro | Val | Ile | Asn | Gly | Thr | Ser | Val | Val | Leu | |
| | | | 260 | | | | 265 | | | | 270 | | | | | |
| cag | tat | gaa | att | gaa | acg | gat | cct | gcc | ttg | acg | tat | gta | gaa | gga | gtg | 864 |
| Gln | Tyr | Glu | Ile | Glu | Thr | Asp | Pro | Ala | Leu | Thr | Tyr | Val | Glu | Gly | Val | |
| | | 275 | | | | | 280 | | | | | 285 | | | | |
| tgt | gtg | gtg | tgg | ttt | act | ttt | gaa | ttt | tta | gtc | cgt | att | gtt | ttt | tca | 912 |
| Cys | Val | Val | Trp | Phe | Thr | Phe | Glu | Phe | Leu | Val | Arg | Ile | Val | Phe | Ser | |
| | 290 | | | | | 295 | | | | | 300 | | | | | |
| ccc | aat | aaa | ctt | gaa | ttc | atc | aaa | aat | ctc | ttg | aat | atc | att | gac | ttt | 960 |
| Pro | Asn | Lys | Leu | Glu | Phe | Ile | Lys | Asn | Leu | Leu | Asn | Ile | Ile | Asp | Phe | |
| 305 | | | | | 310 | | | | | 315 | | | | | 320 | |
| gtg | gcc | atc | cta | cct | ttc | tac | tta | gag | gtg | gga | ctc | agt | ggg | ctg | tca | 1008 |
| Val | Ala | Ile | Leu | Pro | Phe | Tyr | Leu | Glu | Val | Gly | Leu | Ser | Gly | Leu | Ser | |
| | | | | 325 | | | | | 330 | | | | | 335 | | |
| tcc | aaa | gct | gct | aaa | gat | gtg | ctt | ggc | ttc | ctc | agg | gtg | gta | agg | ttt | 1056 |
| Ser | Lys | Ala | Ala | Lys | Asp | Val | Leu | Gly | Phe | Leu | Arg | Val | Val | Arg | Phe | |
| | | | 340 | | | | | 345 | | | | | 350 | | | |
| gtg | agg | atc | ctg | aga | att | ttc | aag | ctc | acc | cgc | cat | ttt | gta | ggt | ctg | 1104 |
| Val | Arg | Ile | Leu | Arg | Ile | Phe | Lys | Leu | Thr | Arg | His | Phe | Val | Gly | Leu | |
| | 355 | | | | | 360 | | | | | 365 | | | | | |
| agg | gtg | ctt | gga | cat | act | ctt | cga | gct | agt | act | aat | gaa | ttt | ttg | ctg | 1152 |
| Arg | Val | Leu | Gly | His | Thr | Leu | Arg | Ala | Ser | Thr | Asn | Glu | Phe | Leu | Leu | |
| | 370 | | | | | 375 | | | | | 380 | | | | | |
| ctg | ata | att | ttc | ctg | gct | cta | gga | gtt | ttg | ata | ttt | gct | acc | atg | atc | 1200 |
| Leu | Ile | Ile | Phe | Leu | Ala | Leu | Gly | Val | Leu | Ile | Phe | Ala | Thr | Met | Ile | |
| 385 | | | | | 390 | | | | | 395 | | | | | 400 | |
| tac | tat | gcc | gag | aga | gtg | gga | gct | caa | cct | aac | gac | cct | tca | gct | agt | 1248 |
| Tyr | Tyr | Ala | Glu | Arg | Val | Gly | Ala | Gln | Pro | Asn | Asp | Pro | Ser | Ala | Ser | |
| | | | | 405 | | | | | 410 | | | | | 415 | | |
| gag | cac | aca | cag | ttc | aaa | aac | att | ccc | att | ggg | ttc | tgg | tgg | gct | gta | 1296 |
| Glu | His | Thr | Gln | Phe | Lys | Asn | Ile | Pro | Ile | Gly | Phe | Trp | Trp | Ala | Val | |
| | | | 420 | | | | | 425 | | | | | 430 | | | |
| gtg | acc | atg | act | acc | ctg | ggt | tat | ggg | gat | atg | tac | ccc | caa | aca | tgg | 1344 |
| Val | Thr | Met | Thr | Thr | Leu | Gly | Tyr | Gly | Asp | Met | Tyr | Pro | Gln | Thr | Trp | |
| | | | 435 | | | | | 440 | | | | | 445 | | | |
| tca | ggc | atg | ctg | gtg | gga | gcc | ctg | tgt | gct | ctg | gct | gga | gtg | ctg | aca | 1392 |
| Ser | Gly | Met | Leu | Val | Gly | Ala | Leu | Cys | Ala | Leu | Ala | Gly | Val | Leu | Thr | |
| | 450 | | | | | 455 | | | | | 460 | | | | | |
| ata | gcc | atg | cca | gtg | cct | gtc | att | gtc | aat | aat | ttt | gga | atg | tac | tac | 1440 |
| Ile | Ala | Met | Pro | Val | Pro | Val | Ile | Val | Asn | Asn | Phe | Gly | Met | Tyr | Tyr | |
| 465 | | | | 470 | | | | | 475 | | | | | 480 | | |
| tcc | ttg | gca | atg | gca | aag | cag | aaa | ctt | cca | agg | aaa | aga | aag | aag | cac | 1488 |
| Ser | Leu | Ala | Met | Ala | Lys | Gln | Lys | Leu | Pro | Arg | Lys | Arg | Lys | Lys | His | |
| | | | | 485 | | | | | 490 | | | | | 495 | | |
| atc | cct | cct | gct | cct | cag | gca | agc | tca | cct | act | ttt | tgc | aag | aca | gaa | 1536 |
| Ile | Pro | Pro | Ala | Pro | Gln | Ala | Ser | Ser | Pro | Thr | Phe | Cys | Lys | Thr | Glu | |

-continued

```
                        500                 505                 510
tta aat atg gcc tgc aat agt aca cag agt gac aca tgt ctg ggc aaa      1584
Leu Asn Met Ala Cys Asn Ser Thr Gln Ser Asp Thr Cys Leu Gly Lys
        515                 520                 525 gac aat cga ctt ctg gaa cat aac aga tca gtg tta tca ggt gac gac      1632
Asp Asn Arg Leu Leu Glu His Asn Arg Ser Val Leu Ser Gly Asp Asp
530                 535                 540 agt aca gga agt gag ccg cca cta tca ccc cca gaa agg ctc ccc atc      1680
Ser Thr Gly Ser Glu Pro Pro Leu Ser Pro Pro Glu Arg Leu Pro Ile
545                 550                 555                 560 aga cgc tct agt acc aga gac aaa aac aga aga ggg gaa aca tgt ttc      1728
Arg Arg Ser Ser Thr Arg Asp Lys Asn Arg Arg Gly Glu Thr Cys Phe
                565                 570                 575 cta ctg acg aca ggt gat tac acg tgt gct tct gat gga ggg atc agg      1776
Leu Leu Thr Thr Gly Asp Tyr Thr Cys Ala Ser Asp Gly Gly Ile Arg
            580                 585                 590 aaa gat aac tgc aaa gag gtt gtc att act ggt tac acg caa gcc gag      1824
Lys Asp Asn Cys Lys Glu Val Val Ile Thr Gly Tyr Thr Gln Ala Glu
                595                 600                 605 gcc aga tct ctt act taa                                              1842
Ala Arg Ser Leu Thr
    610
```

<210> SEQ ID NO 2
<211> LENGTH: 613
<212> TYPE: PRT
<213> ORGANISM: Homo sapiens

<400> SEQUENCE: 2

```
Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Pro Gly Asp Cys Leu Thr
        35                  40                  45

Thr Ala Gly Asp Lys Leu Gln Pro Ser Pro Pro Leu Ser Pro Pro
    50                  55                  60

Pro Arg Ala Pro Pro Leu Ser Pro Gly Pro Gly Cys Phe Glu Gly
65                  70                  75                  80

Gly Ala Gly Asn Cys Ser Ser Arg Gly Gly Arg Ala Ser Asp His Pro
                85                  90                  95

Gly Gly Gly Arg Glu Phe Phe Phe Asp Arg His Pro Gly Val Phe Ala
            100                 105                 110

Tyr Val Leu Asn Tyr Tyr Arg Thr Gly Lys Leu His Cys Pro Ala Asp
        115                 120                 125

Val Cys Gly Pro Leu Phe Glu Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
            180                 185                 190

Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
    210                 215                 220
```

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
            245                 250                 255

Val Lys Asn Lys Thr Glu Pro Val Ile Asn Gly Thr Ser Val Val Leu
        260                 265                 270

Gln Tyr Glu Ile Glu Thr Asp Pro Ala Leu Thr Tyr Val Glu Gly Val
    275                 280                 285

Cys Val Val Trp Phe Thr Phe Glu Phe Leu Val Arg Ile Val Phe Ser
290                 295                 300

Pro Asn Lys Leu Glu Phe Ile Lys Asn Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
        355                 360                 365

Arg Val Leu Gly His Thr Leu Arg Ala Ser Thr Asn Glu Phe Leu Leu
370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
        435                 440                 445

Ser Gly Met Leu Val Gly Ala Leu Cys Ala Leu Ala Gly Val Leu Thr
    450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
            500                 505                 510

Leu Asn Met Ala Cys Asn Ser Thr Gln Ser Asp Thr Cys Leu Gly Lys
        515                 520                 525

Asp Asn Arg Leu Leu Glu His Asn Arg Ser Val Leu Ser Gly Asp Asp
530                 535                 540

Ser Thr Gly Ser Glu Pro Pro Leu Ser Pro Pro Glu Arg Leu Pro Ile
545                 550                 555                 560

Arg Arg Ser Ser Thr Arg Asp Lys Asn Arg Arg Gly Glu Thr Cys Phe
                565                 570                 575

Leu Leu Thr Thr Gly Asp Tyr Thr Cys Ala Ser Asp Gly Gly Ile Arg
            580                 585                 590

Lys Asp Asn Cys Lys Glu Val Val Ile Thr Gly Tyr Thr Gln Ala Glu
        595                 600                 605

Ala Arg Ser Leu Thr
610

<210> SEQ ID NO 3
<211> LENGTH: 1917

<212> TYPE: DNA
<213> ORGANISM: Homo sapiens
<220> FEATURE:
<221> NAME/KEY: CDS
<222> LOCATION: (1)..(1914)

<400> SEQUENCE: 3

```
atg ggc aag atc gag aac aac gag agg gtg atc ctc aat gtc ggg ggc      48
Met Gly Lys Ile Glu Asn Asn Glu Arg Val Ile Leu Asn Val Gly Gly
1               5                  10                  15 acc cgg cac gaa acc tac cgc agc acc ctc aag acc ctg cct gga aca      96
Thr Arg His Glu Thr Tyr Arg Ser Thr Leu Lys Thr Leu Pro Gly Thr
            20                  25                  30 cgc ctg gcc ctt ctt gcc tcc tcc gag ccc cca ggc gac tgc ttg acc     144
Arg Leu Ala Leu Leu Ala Ser Ser Glu Pro Pro Gly Asp Cys Leu Thr
        35                  40                  45 acg gcg ggc gac aag ctg cag ccg tcg ccg cct cca ctg tcg ccg ccg     192
Thr Ala Gly Asp Lys Leu Gln Pro Ser Pro Pro Pro Leu Ser Pro Pro
    50                  55                  60 ccg aga gcg ccc ccg ctg tcc ccc ggg cca ggc ggc tgc ttc gag ggc     240
Pro Arg Ala Pro Pro Leu Ser Pro Gly Pro Gly Gly Cys Phe Glu Gly
65                  70                  75                  80 ggc gcg ggc aac tgc agt tcc cgc ggc ggc agg gcc agc gac cat ccc     288
Gly Ala Gly Asn Cys Ser Ser Arg Gly Gly Arg Ala Ser Asp His Pro
                85                  90                  95 ggt ggc ggc cgc gag ttc ttc ttc gac cgg cac ccg ggc gtc ttc gcc     336
Gly Gly Gly Arg Glu Phe Phe Phe Asp Arg His Pro Gly Val Phe Ala
            100                 105                 110 tat gtg ctc aat tac tac cgc acc ggc aag ctg cac tgc ccc gca gac     384
Tyr Val Leu Asn Tyr Tyr Arg Thr Gly Lys Leu His Cys Pro Ala Asp
        115                 120                 125 gtg tgc ggg ccg ctc ttc gag gag gag ctg gcc ttc tgg ggc atc gac     432
Val Cys Gly Pro Leu Phe Glu Glu Glu Leu Ala Phe Trp Gly Ile Asp
    130                 135                 140 gag acc gac gtg gag ccc tgc tgc tgg atg acc tac cgg cag cac cgc     480
Glu Thr Asp Val Glu Pro Cys Cys Trp Met Thr Tyr Arg Gln His Arg
145                 150                 155                 160 gac gcc gag gag gcg ctg gac atc ttc gag acc ccc gac ctc att ggc     528
Asp Ala Glu Glu Ala Leu Asp Ile Phe Glu Thr Pro Asp Leu Ile Gly
                165                 170                 175 ggc gac ccc ggc gac gac gag gac ctg gcg gcc aag agg ctg ggc atc     576
Gly Asp Pro Gly Asp Asp Glu Asp Leu Ala Ala Lys Arg Leu Gly Ile
            180                 185                 190 gag gac gcg gcg ggg ctc ggg ggc ccc gac ggc aaa tct ggc cgc tgg     624
Glu Asp Ala Ala Gly Leu Gly Gly Pro Asp Gly Lys Ser Gly Arg Trp
        195                 200                 205 agg agg ctg cag ccc cgc atg tgg gcc ctc ttc gaa gac ccc tac tcg     672
Arg Arg Leu Gln Pro Arg Met Trp Ala Leu Phe Glu Asp Pro Tyr Ser
    210                 215                 220 tcc aga gcc gcc agg ttt att gct ttt gct tct tta ttc ttc atc ctg     720
Ser Arg Ala Ala Arg Phe Ile Ala Phe Ala Ser Leu Phe Phe Ile Leu
225                 230                 235                 240 gtt tca att aca act ttt tgc ctg gaa aca cat gaa gct ttc aat att     768
Val Ser Ile Thr Thr Phe Cys Leu Glu Thr His Glu Ala Phe Asn Ile
                245                 250                 255 gtt aaa aac aag aca gaa cca gtc atc aat ggc aca agt gtt gtt cta     816
Val Lys Asn Lys Thr Glu Pro Val Ile Asn Gly Thr Ser Val Val Leu
            260                 265                 270 cag tat gaa att gaa acg gat cct gcc ttg acg tat gta gaa gga gtg     864
Gln Tyr Glu Ile Glu Thr Asp Pro Ala Leu Thr Tyr Val Glu Gly Val
        275                 280                 285
```

| | | |
|---|---|---|
| tgt gtg gtg tgg ttt act ttt gaa ttt tta gtc cgt att gtt ttt tca<br>Cys Val Val Trp Phe Thr Phe Glu Phe Leu Val Arg Ile Val Phe Ser<br>290                          295                           300 | | 912 |
| ccc aat aaa ctt gaa ttc atc aaa aat ctc ttg aat atc att gac ttt<br>Pro Asn Lys Leu Glu Phe Ile Lys Asn Leu Leu Asn Ile Ile Asp Phe<br>305                   310                      315                    320 | | 960 |
| gtg gcc atc cta cct ttc tac tta gag gtg gga ctc agt ggg ctg tca<br>Val Ala Ile Leu Pro Phe Tyr Leu Glu Val Gly Leu Ser Gly Leu Ser<br>                      325                      330                    335 | | 1008 |
| tcc aaa gct gct aaa gat gtg ctt ggc ttc ctc agg gtg gta agg ttt<br>Ser Lys Ala Ala Lys Asp Val Leu Gly Phe Leu Arg Val Val Arg Phe<br>                340                      345                    350 | | 1056 |
| gtg agg atc ctg aga att ttc aag ctc acc cgc cat ttt gta ggt ctg<br>Val Arg Ile Leu Arg Ile Phe Lys Leu Thr Arg His Phe Val Gly Leu<br>         355                      360                    365 | | 1104 |
| agg gtg ctt gga cat act ctt cga gct agt act aat gaa ttt ttg ctg<br>Arg Val Leu Gly His Thr Leu Arg Ala Ser Thr Asn Glu Phe Leu Leu<br>370                          375                      380 | | 1152 |
| ctg ata att ttc ctg gct cta gga gtt ttg ata ttt gct acc atg atc<br>Leu Ile Ile Phe Leu Ala Leu Gly Val Leu Ile Phe Ala Thr Met Ile<br>385                          390                      395                    400 | | 1200 |
| tac tat gcc gag aga gtg gga gct caa cct aac gac cct tca gct agt<br>Tyr Tyr Ala Glu Arg Val Gly Ala Gln Pro Asn Asp Pro Ser Ala Ser<br>                      405                      410                    415 | | 1248 |
| gag cac aca cag ttc aaa aac att ccc att ggg ttc tgg tgg gct gta<br>Glu His Thr Gln Phe Lys Asn Ile Pro Ile Gly Phe Trp Trp Ala Val<br>                420                      425                    430 | | 1296 |
| gtg acc atg act acc ctg ggt tat ggg gat atg tac ccc caa aca tgg<br>Val Thr Met Thr Thr Leu Gly Tyr Gly Asp Met Tyr Pro Gln Thr Trp<br>         435                      440                    445 | | 1344 |
| tca ggc atg ctg gtg gga gcc ctg tgt gct ctg gct gga gtg ctg aca<br>Ser Gly Met Leu Val Gly Ala Leu Cys Ala Leu Ala Gly Val Leu Thr<br>450                          455                      460 | | 1392 |
| ata gcc atg cca gtg cct gtc att gtc aat aat ttt gga atg tac tac<br>Ile Ala Met Pro Val Pro Val Ile Val Asn Asn Phe Gly Met Tyr Tyr<br>465                          470                      475                    480 | | 1440 |
| tcc ttg gca atg gca aag cag aaa ctt cca agg aaa aga aag aag cac<br>Ser Leu Ala Met Ala Lys Gln Lys Leu Pro Arg Lys Arg Lys Lys His<br>                      485                      490                    495 | | 1488 |
| atc cct cct gct cct cag gca agc tca cct act ttt tgc aag aca gaa<br>Ile Pro Pro Ala Pro Gln Ala Ser Ser Pro Thr Phe Cys Lys Thr Glu<br>                500                      505                    510 | | 1536 |
| tta aat atg gcc tgc aat agt aca cag agt gac aca tgt ctg ggc aaa<br>Leu Asn Met Ala Cys Asn Ser Thr Gln Ser Asp Thr Cys Leu Gly Lys<br>         515                      520                    525 | | 1584 |
| gac aat cga ctt ctg gaa cat aac aga tca gtg tta tca ggt gac gac<br>Asp Asn Arg Leu Leu Glu His Asn Arg Ser Val Leu Ser Gly Asp Asp<br>530                          535                      540 | | 1632 |
| agt aca gga agt gag ccg cca cta tca ccc cca gaa agg ctc ccc atc<br>Ser Thr Gly Ser Glu Pro Pro Leu Ser Pro Pro Glu Arg Leu Pro Ile<br>545                          550                      555                    560 | | 1680 |
| aga cgc tct agt acc aga gac aaa aac aga aga ggg gaa aca tgt ttc<br>Arg Arg Ser Ser Thr Arg Asp Lys Asn Arg Arg Gly Glu Thr Cys Phe<br>                      565                      570                    575 | | 1728 |
| cta ctg acg aca ggt gat tac acg tgt gct tct gat gga ggg atc agg<br>Leu Leu Thr Thr Gly Asp Tyr Thr Cys Ala Ser Asp Gly Gly Ile Arg<br>                      580                      585                    590 | | 1776 |
| aaa gga tat gaa aaa tcc cga agc tta aac aac ata gcg ggc ttg gca<br>Lys Gly Tyr Glu Lys Ser Arg Ser Leu Asn Asn Ile Ala Gly Leu Ala | | 1824 |

```
                595                 600                 605
ggc aat gct ctg agg ctc tct cca gta aca tca ccc tac aac tct cct    1872
Gly Asn Ala Leu Arg Leu Ser Pro Val Thr Ser Pro Tyr Asn Ser Pro
610                 615                 620 tgt cct ctg agg cgc tct cga tct ccc atc cca tct atc ttg taa        1917
Cys Pro Leu Arg Arg Ser Arg Ser Pro Ile Pro Ser Ile Leu
625                 630                 635

<210> SEQ ID NO 4
<211> LENGTH: 638
<212> TYPE: PRT
<213> ORGANISM: Homo sapiens

<400> SEQUENCE: 4

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Ala Ser Ser Glu Pro Pro Gly Asp Cys Leu Thr
        35                  40                  45

Thr Ala Gly Asp Lys Leu Gln Pro Ser Pro Pro Leu Ser Pro Pro
50                  55                  60

Pro Arg Ala Pro Pro Leu Ser Pro Gly Pro Gly Gly Cys Phe Glu Gly
65                  70                  75                  80

Gly Ala Gly Asn Cys Ser Ser Arg Gly Gly Arg Ala Ser Asp His Pro
                85                  90                  95

Gly Gly Gly Arg Glu Phe Phe Phe Asp Arg His Pro Gly Val Phe Ala
            100                 105                 110

Tyr Val Leu Asn Tyr Tyr Arg Thr Gly Lys Leu His Cys Pro Ala Asp
        115                 120                 125

Val Cys Gly Pro Leu Phe Glu Glu Glu Leu Ala Phe Trp Gly Ile Asp
130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
            180                 185                 190

Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
            260                 265                 270

Gln Tyr Glu Ile Glu Thr Asp Pro Ala Leu Thr Tyr Val Glu Gly Val
        275                 280                 285

Cys Val Val Trp Phe Thr Phe Glu Phe Leu Val Arg Ile Val Phe Ser
290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
```

```
                  325                 330                 335
Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
            355                 360                 365

Arg Val Leu Gly His Thr Leu Arg Ala Ser Thr Asn Glu Phe Leu Leu
            370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
            405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
            435                 440                 445

Ser Gly Met Leu Val Gly Ala Leu Cys Ala Leu Ala Gly Val Leu Thr
            450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
            485                 490                 495

Ile Pro Pro Ala Pro Gln Ala Ser Ser Pro Thr Phe Cys Lys Thr Glu
            500                 505                 510

Leu Asn Met Ala Cys Asn Ser Thr Gln Ser Asp Thr Cys Leu Gly Lys
            515                 520                 525

Asp Asn Arg Leu Leu Glu His Asn Arg Ser Val Leu Ser Gly Asp Asp
            530                 535                 540

Ser Thr Gly Ser Glu Pro Pro Leu Ser Pro Glu Arg Leu Pro Ile
545                 550                 555                 560

Arg Arg Ser Ser Thr Arg Asp Lys Asn Arg Arg Gly Glu Thr Cys Phe
            565                 570                 575

Leu Leu Thr Thr Gly Asp Tyr Thr Cys Ala Ser Asp Gly Gly Ile Arg
            580                 585                 590

Lys Gly Tyr Glu Lys Ser Arg Ser Leu Asn Asn Ile Ala Gly Leu Ala
            595                 600                 605

Gly Asn Ala Leu Arg Leu Ser Pro Val Thr Ser Pro Tyr Asn Ser Pro
            610                 615                 620

Cys Pro Leu Arg Arg Ser Arg Ser Pro Ile Pro Ser Ile Leu
625                 630                 635

<210> SEQ ID NO 5
<211> LENGTH: 1677
<212> TYPE: DNA
<213> ORGANISM: Homo sapiens
<220> FEATURE:
<221> NAME/KEY: CDS
<222> LOCATION: (1)..(1674)

<400> SEQUENCE: 5 atg ggc aag atc gag aac aac gag agg gtg atc ctc aat gtc ggg ggc        48
Met Gly Lys Ile Glu Asn Asn Glu Arg Val Ile Leu Asn Val Gly Gly
1               5                   10                  15 acc cgg cac gaa acc tac cgc agc acc ctc aag acc ctg cct gga aca        96
Thr Arg His Glu Thr Tyr Arg Ser Thr Leu Lys Thr Leu Pro Gly Thr
            20                  25                  30 cgc ctg gcc ctt ctt gcc tcc tcc gag ccc cca ggc gac tgc ttg acc       144
```

```
          Arg Leu Ala Leu Leu Ala Ser Ser Glu Pro Pro Gly Asp Cys Leu Thr
                   35                  40                  45 acg gcg ggc gac aag ctg cag ccg tcg ccg cct cca ctg tcg ccg ccg              192
Thr Ala Gly Asp Lys Leu Gln Pro Ser Pro Pro Pro Leu Ser Pro Pro
    50                  55                  60 ccg aga gcg ccc ccg ctg tcc ccc ggg cca ggc ggc tgc ttc gag ggc              240
Pro Arg Ala Pro Pro Leu Ser Pro Gly Pro Gly Gly Cys Phe Glu Gly
65                  70                  75                  80 ggc gcg ggc aac tgc agt tcc cgc ggc ggc agg gcc agc gac cat ccc              288
Gly Ala Gly Asn Cys Ser Ser Arg Gly Gly Arg Ala Ser Asp His Pro
                85                  90                  95 ggt ggc ggc cgc gag ttc ttc ttc gac cgg cac ccg ggc gtc ttc gcc              336
Gly Gly Gly Arg Glu Phe Phe Phe Asp Arg His Pro Gly Val Phe Ala
            100                 105                 110 tat gtg ctc aat tac tac cgc acc ggc aag ctg cac tgc ccc gca gac              384
Tyr Val Leu Asn Tyr Tyr Arg Thr Gly Lys Leu His Cys Pro Ala Asp
            115                 120                 125 gtg tgc ggg ccg ctc ttc gag gag gag ctg gcc ttc tgg ggc atc gac              432
Val Cys Gly Pro Leu Phe Glu Glu Glu Leu Ala Phe Trp Gly Ile Asp
        130                 135                 140 gag acc gac gtg gag ccc tgc tgc tgg atg acc tac cgg cag cac cgc              480
Glu Thr Asp Val Glu Pro Cys Cys Trp Met Thr Tyr Arg Gln His Arg
145                 150                 155                 160 gac gcc gag gag gcg ctg gac atc ttc gag acc ccc gac ctc att ggc              528
Asp Ala Glu Glu Ala Leu Asp Ile Phe Glu Thr Pro Asp Leu Ile Gly
                165                 170                 175 ggc gac ccc ggc gac gac gag gac ctg gcg gcc aag agg ctg ggc atc              576
Gly Asp Pro Gly Asp Asp Glu Asp Leu Ala Ala Lys Arg Leu Gly Ile
            180                 185                 190 gag gac gcg gcg ggg ctc ggg ggc ccc gac ggc aaa tct ggc cgc tgg              624
Glu Asp Ala Ala Gly Leu Gly Gly Pro Asp Gly Lys Ser Gly Arg Trp
        195                 200                 205 agg agg ctg cag ccc cgc atg tgg gcc ctc ttc gaa gac ccc tac tcg              672
Arg Arg Leu Gln Pro Arg Met Trp Ala Leu Phe Glu Asp Pro Tyr Ser
    210                 215                 220 tcc aga gcc gcc agg ttt att gct ttt gct tct tta ttc ttc atc ctg              720
Ser Arg Ala Ala Arg Phe Ile Ala Phe Ala Ser Leu Phe Phe Ile Leu
225                 230                 235                 240 gtt tca att aca act ttt tgc ctg gaa aca cat gaa gct ttc aat att              768
Val Ser Ile Thr Thr Phe Cys Leu Glu Thr His Glu Ala Phe Asn Ile
                245                 250                 255 gtt aaa aac aag aca gaa cca gtc atc aat ggc aca agt gtt gtt cta              816
Val Lys Asn Lys Thr Glu Pro Val Ile Asn Gly Thr Ser Val Val Leu
            260                 265                 270 cag tat gaa att gaa acg gat cct gcc ttg acg tat gta gaa gga gtg              864
Gln Tyr Glu Ile Glu Thr Asp Pro Ala Leu Thr Tyr Val Glu Gly Val
        275                 280                 285 tgt gtg gtg tgg ttt act ttt gaa ttt tta gtc cgt att gtt ttt tca              912
Cys Val Val Trp Phe Thr Phe Glu Phe Leu Val Arg Ile Val Phe Ser
    290                 295                 300 ccc aat aaa ctt gaa ttc atc aaa aat ctc ttg aat atc att gac ttt              960
Pro Asn Lys Leu Glu Phe Ile Lys Asn Leu Leu Asn Ile Ile Asp Phe
305                 310                 315                 320 gtg gcc atc cta cct ttc tac tta gag gtg gga ctc agt ggg ctg tca             1008
Val Ala Ile Leu Pro Phe Tyr Leu Glu Val Gly Leu Ser Gly Leu Ser
                325                 330                 335 tcc aaa gct gct aaa gat gtg ctt ggc ttc ctc agg gtg gta agg ttt             1056
Ser Lys Ala Ala Lys Asp Val Leu Gly Phe Leu Arg Val Val Arg Phe
            340                 345                 350
```

```
gtg agg atc ctg aga att ttc aag ctc acc cgc cat ttt gta ggt ctg    1104
Val Arg Ile Leu Arg Ile Phe Lys Leu Thr Arg His Phe Val Gly Leu
            355                 360                 365 agg gtg ctt gga cat act ctt cga gct agt act aat gaa ttt ttg ctg    1152
Arg Val Leu Gly His Thr Leu Arg Ala Ser Thr Asn Glu Phe Leu Leu
    370                 375                 380 ctg ata att ttc ctg gct cta gga gtt ttg ata ttt gct acc atg atc    1200
Leu Ile Ile Phe Leu Ala Leu Gly Val Leu Ile Phe Ala Thr Met Ile
385                 390                 395                 400 tac tat gcc gag aga gtg gga gct caa cct aac gac cct tca gct agt    1248
Tyr Tyr Ala Glu Arg Val Gly Ala Gln Pro Asn Asp Pro Ser Ala Ser
                405                 410                 415 gag cac aca cag ttc aaa aac att ccc att ggg ttc tgg tgg gct gta    1296
Glu His Thr Gln Phe Lys Asn Ile Pro Ile Gly Phe Trp Trp Ala Val
            420                 425                 430 gtg acc atg act acc ctg ggt tat ggg gat atg tac ccc caa aca tgg    1344
Val Thr Met Thr Thr Leu Gly Tyr Gly Asp Met Tyr Pro Gln Thr Trp
    435                 440                 445 tca ggc atg ctg gtg gga gcc ctg tgt gct ctg gct gga gtg ctg aca    1392
Ser Gly Met Leu Val Gly Ala Leu Cys Ala Leu Ala Gly Val Leu Thr
450                 455                 460 ata gcc atg cca gtg cct gtc att gtc aat aat ttt gga atg tac tac    1440
Ile Ala Met Pro Val Pro Val Ile Val Asn Asn Phe Gly Met Tyr Tyr
465                 470                 475                 480 tcc ttg gca atg gca aag cag aaa ctt cca agg aaa aga aag aag cac    1488
Ser Leu Ala Met Ala Lys Gln Lys Leu Pro Arg Lys Arg Lys Lys His
                485                 490                 495 atc cct cct gct cct cag gca agc tca cct act ttt tgc aag aca gaa    1536
Ile Pro Pro Ala Pro Gln Ala Ser Ser Pro Thr Phe Cys Lys Thr Glu
            500                 505                 510 tta aat atg gcc tgc aat agt aca cag agt gac aca tgt ctg ggc aaa    1584
Leu Asn Met Ala Cys Asn Ser Thr Gln Ser Asp Thr Cys Leu Gly Lys
    515                 520                 525 gac aat cga ctt ctg gaa cat aac aga tca gat aac tgc aaa gag gtt    1632
Asp Asn Arg Leu Leu Glu His Asn Arg Ser Asp Asn Cys Lys Glu Val
530                 535                 540 gtc att act ggt tac acg caa gcc gag gcc aga tct ctt act taa        1677
Val Ile Thr Gly Tyr Thr Gln Ala Glu Ala Arg Ser Leu Thr
545                 550                 555

<210> SEQ ID NO 6
<211> LENGTH: 558
<212> TYPE: PRT
<213> ORGANISM: Homo sapiens

<400> SEQUENCE: 6

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gly Asp Cys Leu Thr
        35                  40                  45

Thr Ala Gly Asp Lys Leu Gln Pro Ser Pro Pro Leu Ser Pro Pro
    50                  55                  60

Pro Arg Ala Pro Pro Leu Ser Pro Gly Pro Gly Cys Phe Glu Gly
65                  70                  75                  80

Gly Ala Gly Asn Cys Ser Ser Arg Gly Arg Ala Ser Asp His Pro
                85                  90                  95

Gly Gly Gly Arg Glu Phe Phe Asp Arg His Pro Gly Val Phe Ala
```

```
                    100                 105                 110
Tyr Val Leu Asn Tyr Tyr Arg Thr Gly Lys Leu His Cys Pro Ala Asp
            115                 120                 125

Val Cys Gly Pro Leu Phe Glu Glu Leu Ala Phe Trp Gly Ile Asp
130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
                180                 185                 190

Glu Asp Ala Ala Gly Leu Gly Gly Pro Asp Gly Lys Ser Gly Arg Trp
                195                 200                 205

Arg Arg Leu Gln Pro Arg Met Trp Ala Leu Phe Glu Asp Pro Tyr Ser
                210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
                260                 265                 270

Gln Tyr Glu Ile Glu Thr Asp Pro Ala Leu Thr Tyr Val Glu Gly Val
                275                 280                 285

Cys Val Val Trp Phe Thr Phe Glu Phe Leu Val Arg Ile Val Phe Ser
                290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
                340                 345                 350

Val Arg Ile Leu Arg Ile Phe Lys Leu Thr Arg His Phe Val Gly Leu
                355                 360                 365

Arg Val Leu Gly His Thr Leu Arg Ala Ser Thr Asn Glu Phe Leu Leu
                370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
                420                 425                 430

Val Thr Met Thr Thr Leu Gly Tyr Gly Asp Met Tyr Pro Gln Thr Trp
                435                 440                 445

Ser Gly Met Leu Val Gly Ala Leu Cys Ala Leu Ala Gly Val Leu Thr
                450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
                500                 505                 510

Leu Asn Met Ala Cys Asn Ser Thr Gln Ser Asp Thr Cys Leu Gly Lys
                515                 520                 525
```

| | | | | | | | | | | | | |
|---|---|---|---|---|---|---|---|---|---|---|---|---|
| Asp | Asn | Arg | Leu | Leu | Glu | His | Asn | Arg | Ser | Asp | Asn | Cys | Lys | Glu | Val |
| | 530 | | | | 535 | | | | 540 | | | |

Val Ile Thr Gly Tyr Thr Gln Ala Glu Ala Arg Ser Leu Thr
545           550              555

<210> SEQ ID NO 7
<211> LENGTH: 1890
<212> TYPE: DNA
<213> ORGANISM: Homo sapiens
<220> FEATURE:
<221> NAME/KEY: CDS
<222> LOCATION: (1)..(1887)

<400> SEQUENCE: 7

```
atg ggc aag atc gag aac aac gag agg gtg atc ctc aat gtc ggg ggc      48
Met Gly Lys Ile Glu Asn Asn Glu Arg Val Ile Leu Asn Val Gly Gly
1               5                   10                  15 acc cgg cac gaa acc tac cgc agc acc ctc aag acc ctg cct gga aca      96
Thr Arg His Glu Thr Tyr Arg Ser Thr Leu Lys Thr Leu Pro Gly Thr
            20                  25                  30 cgc ctg gcc ctt ctt gcc tcc tcc gag ccc cca ggc gac tgc ttg acc     144
Arg Leu Ala Leu Leu Ala Ser Ser Glu Pro Pro Gly Asp Cys Leu Thr
        35                  40                  45 acg gcg ggc gac aag ctg cag ccg tcg ccg cct cca ctg tcg ccg ccg     192
Thr Ala Gly Asp Lys Leu Gln Pro Ser Pro Pro Pro Leu Ser Pro Pro
50                  55                  60 ccg aga gcg ccc ccg ctg tcc ccc ggg cca ggc ggc tgc ttc gag ggc     240
Pro Arg Ala Pro Pro Leu Ser Pro Gly Pro Gly Gly Cys Phe Glu Gly
65                  70                  75                  80 ggc gcg ggc aac tgc agt tcc cgc ggc ggc agg gcc agc gac cat ccc     288
Gly Ala Gly Asn Cys Ser Ser Arg Gly Gly Arg Ala Ser Asp His Pro
                85                  90                  95 ggt ggc ggc cgc gag ttc ttc ttc gac cgg cac ccg ggc gtc ttc gcc     336
Gly Gly Gly Arg Glu Phe Phe Phe Asp Arg His Pro Gly Val Phe Ala
            100                 105                 110 tat gtg ctc aat tac tac cgc acc ggc aag ctg cac tgc ccc gca gac     384
Tyr Val Leu Asn Tyr Tyr Arg Thr Gly Lys Leu His Cys Pro Ala Asp
        115                 120                 125 gtg tgc ggg ccg ctc ttc gag gag gag ctg gcc ttc tgg ggc atc gac     432
Val Cys Gly Pro Leu Phe Glu Glu Glu Leu Ala Phe Trp Gly Ile Asp
130                 135                 140 gag acc gac gtg gag ccc tgc tgc tgg atg acc tac cgg cag cac cgc     480
Glu Thr Asp Val Glu Pro Cys Cys Trp Met Thr Tyr Arg Gln His Arg
145                 150                 155                 160 gac gcc gag gag gcg ctg gac atc ttc gag acc ccc gac ctc att ggc     528
Asp Ala Glu Glu Ala Leu Asp Ile Phe Glu Thr Pro Asp Leu Ile Gly
                165                 170                 175 ggc gac ccc ggc gac gac gag gac ctg gcg gcc aag agg ctg ggc atc     576
Gly Asp Pro Gly Asp Asp Glu Asp Leu Ala Ala Lys Arg Leu Gly Ile
            180                 185                 190 gag gac gcg gcg ggg ctc ggg ggc ccc gac ggc aaa tct ggc cgc tgg     624
Glu Asp Ala Ala Gly Leu Gly Gly Pro Asp Gly Lys Ser Gly Arg Trp
        195                 200                 205 agg agg ctg cag ccc cgc atg tgg gcc ctc ttc gaa gac ccc tac tcg     672
Arg Arg Leu Gln Pro Arg Met Trp Ala Leu Phe Glu Asp Pro Tyr Ser
210                 215                 220 tcc aga gcc gcc agg ttt att gct ttt gct tct tta ttc ttc atc ctg     720
Ser Arg Ala Ala Arg Phe Ile Ala Phe Ala Ser Leu Phe Phe Ile Leu
225                 230                 235                 240 gtt tca att aca act ttt tgc ctg gaa aca cat gaa gct ttc aat att     768
```

```
              Val Ser Ile Thr Thr Phe Cys Leu Glu Thr His Glu Ala Phe Asn Ile
                          245                 250                 255 gtt aaa aac aag aca gaa cca gtc atc aat ggc aca agt gtt gtt cta         816
Val Lys Asn Lys Thr Glu Pro Val Ile Asn Gly Thr Ser Val Val Leu
            260                 265                 270 cag tat gaa att gaa acg gat cct gcc ttg acg tat gta gaa gga gtg         864
Gln Tyr Glu Ile Glu Thr Asp Pro Ala Leu Thr Tyr Val Glu Gly Val
        275                 280                 285 tgt gtg gtg tgg ttt act ttt gaa ttt tta gtc cgt att gtt ttt tca         912
Cys Val Val Trp Phe Thr Phe Glu Phe Leu Val Arg Ile Val Phe Ser
    290                 295                 300 ccc aat aaa ctt gaa ttc atc aaa aat ctc ttg aat atc att gac ttt         960
Pro Asn Lys Leu Glu Phe Ile Lys Asn Leu Leu Asn Ile Ile Asp Phe
305                 310                 315                 320 gtg gcc atc cta cct ttc tac tta gag gtg gga ctc agt ggg ctg tca        1008
Val Ala Ile Leu Pro Phe Tyr Leu Glu Val Gly Leu Ser Gly Leu Ser
                325                 330                 335 tcc aaa gct gct aaa gat gtg ctt ggc ttc ctc agg gtg gta agg ttt        1056
Ser Lys Ala Ala Lys Asp Val Leu Gly Phe Leu Arg Val Val Arg Phe
            340                 345                 350 gtg agg atc ctg aga att ttc aag ctc acc cgc cat ttt gta ggt ctg        1104
Val Arg Ile Leu Arg Ile Phe Lys Leu Thr Arg His Phe Val Gly Leu
        355                 360                 365 agg gtg ctt gga cat act ctt cga gct agt act aat gaa ttt ttg ctg        1152
Arg Val Leu Gly His Thr Leu Arg Ala Ser Thr Asn Glu Phe Leu Leu
    370                 375                 380 ctg ata att ttc ctg gct cta gga gtt ttg ata ttt gct acc atg atc        1200
Leu Ile Ile Phe Leu Ala Leu Gly Val Leu Ile Phe Ala Thr Met Ile
385                 390                 395                 400 tac tat gcc gag aga gtg gga gct caa cct aac gac cct tca gct agt        1248
Tyr Tyr Ala Glu Arg Val Gly Ala Gln Pro Asn Asp Pro Ser Ala Ser
                405                 410                 415 gag cac aca cag ttc aaa aac att ccc att ggg ttc tgg tgg gct gta        1296
Glu His Thr Gln Phe Lys Asn Ile Pro Ile Gly Phe Trp Trp Ala Val
            420                 425                 430 gtg acc atg act acc ctg ggt tat ggg gat atg tac ccc caa aca tgg        1344
Val Thr Met Thr Thr Leu Gly Tyr Gly Asp Met Tyr Pro Gln Thr Trp
        435                 440                 445 tca ggc atg ctg gtg gga gcc ctg tgt gct ctg gct gga gtg ctg aca        1392
Ser Gly Met Leu Val Gly Ala Leu Cys Ala Leu Ala Gly Val Leu Thr
    450                 455                 460 ata gcc atg cca gtg cct gtc att gtc aat aat ttt gga atg tac tac        1440
Ile Ala Met Pro Val Pro Val Ile Val Asn Asn Phe Gly Met Tyr Tyr
465                 470                 475                 480 tcc ttg gca atg gca aag cag aaa ctt cca agg aaa aga aag aag cac        1488
Ser Leu Ala Met Ala Lys Gln Lys Leu Pro Arg Lys Arg Lys Lys His
                485                 490                 495 atc cct cct gct cct cag gca agc tca cct act ttt tgc aag aca gaa        1536
Ile Pro Pro Ala Pro Gln Ala Ser Ser Pro Thr Phe Cys Lys Thr Glu
            500                 505                 510 tta aat atg gcc tgc aat agt aca cag agt gac aca tgt ctg ggc aaa        1584
Leu Asn Met Ala Cys Asn Ser Thr Gln Ser Asp Thr Cys Leu Gly Lys
        515                 520                 525 gac aat cga ctt ctg gaa cat aac aga tca gtg tta tca ggt gac gac        1632
Asp Asn Arg Leu Leu Glu His Asn Arg Ser Val Leu Ser Gly Asp Asp
    530                 535                 540 agt aca gga agt gag ccg cca cta tca ccc cca gaa agg ctc ccc atc        1680
Ser Thr Gly Ser Glu Pro Pro Leu Ser Pro Pro Glu Arg Leu Pro Ile
545                 550                 555                 560
```

```
aga cgc tct agt acc aga gac aaa aac aga aga ggg gaa aca tgt ttc    1728
Arg Arg Ser Ser Thr Arg Asp Lys Asn Arg Arg Gly Glu Thr Cys Phe
                565                 570                 575 cta ctg acg aca ggt gat tac acg tgt gct tct gat gga ggg atc agg    1776
Leu Leu Thr Thr Gly Asp Tyr Thr Cys Ala Ser Asp Gly Gly Ile Arg
            580                 585                 590 aaa gtg ttg tac aga att tat cat gga tta ttg act gct gag aaa ggg    1824
Lys Val Leu Tyr Arg Ile Tyr His Gly Leu Leu Thr Ala Glu Lys Gly
        595                 600                 605 aca gtg gaa ttt agc cat acc aag gac tat act gga aac aga ctt ctg    1872
Thr Val Glu Phe Ser His Thr Lys Asp Tyr Thr Gly Asn Arg Leu Leu
    610                 615                 620 ctg ctg aat gtg ccc tga                                            1890
Leu Leu Asn Val Pro
625
```

<210> SEQ ID NO 8
<211> LENGTH: 629
<212> TYPE: PRT
<213> ORGANISM: Homo sapiens

<400> SEQUENCE: 8

```
Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Pro Gly Asp Cys Leu Thr
        35                  40                  45

Thr Ala Gly Asp Lys Leu Gln Pro Ser Pro Pro Leu Ser Pro Pro
    50                  55                  60

Pro Arg Ala Pro Pro Leu Ser Pro Gly Pro Gly Cys Phe Glu Gly
65                  70                  75                  80

Gly Ala Gly Asn Cys Ser Ser Arg Gly Gly Arg Ala Ser Asp His Pro
                85                  90                  95

Gly Gly Gly Arg Glu Phe Phe Phe Asp Arg His Pro Gly Val Phe Ala
            100                 105                 110

Tyr Val Leu Asn Tyr Tyr Arg Thr Gly Lys Leu His Cys Pro Ala Asp
        115                 120                 125

Val Cys Gly Pro Leu Phe Glu Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Ala Ala Lys Arg Leu Gly Ile
            180                 185                 190

Glu Asp Ala Ala Gly Leu Gly Gly Pro Asp Gly Lys Ser Gly Arg Trp
        195                 200                 205

Arg Arg Leu Gln Pro Arg Met Trp Ala Leu Phe Glu Asp Pro Tyr Ser
    210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Val Val Leu
            260                 265                 270
```

```
Gln Tyr Glu Ile Glu Thr Asp Pro Ala Leu Thr Tyr Val Glu Gly Val
            275                 280                 285

Cys Val Val Trp Phe Thr Phe Glu Phe Leu Val Arg Ile Val Phe Ser
290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
        355                 360                 365

Arg Val Leu Gly His Thr Leu Arg Ala Ser Thr Asn Glu Phe Leu Leu
370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
        435                 440                 445

Ser Gly Met Leu Val Gly Ala Leu Cys Ala Leu Ala Gly Val Leu Thr
450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Gln Ala Ser Ser Pro Thr Phe Cys Lys Thr Glu
            500                 505                 510

Leu Asn Met Ala Cys Asn Ser Thr Gln Ser Asp Thr Cys Leu Gly Lys
        515                 520                 525

Asp Asn Arg Leu Leu Glu His Asn Arg Ser Val Leu Ser Gly Asp Asp
530                 535                 540

Ser Thr Gly Ser Glu Pro Pro Leu Ser Pro Glu Arg Leu Pro Ile
545                 550                 555                 560

Arg Arg Ser Ser Thr Arg Asp Lys Asn Arg Arg Gly Glu Thr Cys Phe
                565                 570                 575

Leu Leu Thr Thr Gly Asp Tyr Thr Cys Ala Ser Asp Gly Gly Ile Arg
            580                 585                 590

Lys Val Leu Tyr Arg Ile Tyr His Gly Leu Leu Thr Ala Glu Lys Gly
        595                 600                 605

Thr Val Glu Phe Ser His Thr Lys Asp Tyr Thr Gly Asn Arg Leu Leu
610                 615                 620

Leu Leu Asn Val Pro
625

<210> SEQ ID NO 9
<211> LENGTH: 1920
<212> TYPE: DNA
<213> ORGANISM: Mus musculus
<220> FEATURE:
<221> NAME/KEY: CDS
<222> LOCATION: (1)..(1917)

<400> SEQUENCE: 9
```

| | | |
|---|---|---|
| atg ggc aag atc gag agc aac gag agg gtg atc ctc aat gtc ggg ggt<br>Met Gly Lys Ile Glu Ser Asn Glu Arg Val Ile Leu Asn Val Gly Gly<br>1               5                   10                  15 | | 48 |
| acc agg cac gaa acc tac cgc agc acc ctc aag acc ctg cct gga act<br>Thr Arg His Glu Thr Tyr Arg Ser Thr Leu Lys Thr Leu Pro Gly Thr<br>            20                  25                  30 | | 96 |
| cgc ctg gcc ctt ctt gcc tcc tct gaa cct cag ggc gac tgc ctg act<br>Arg Leu Ala Leu Leu Ala Ser Ser Glu Pro Gln Gly Asp Cys Leu Thr<br>        35                  40                  45 | | 144 |
| gcg gcc ggg gac aag ctg caa ccg ctg ccc cct ccg ctg tct ccg ccg<br>Ala Ala Gly Asp Lys Leu Gln Pro Leu Pro Pro Pro Leu Ser Pro Pro<br>    50                  55                  60 | | 192 |
| cca cga ccg cct ccc ttg tcc cct gtc ccc agc ggc tgc ttc gag ggc<br>Pro Arg Pro Pro Pro Leu Ser Pro Val Pro Ser Gly Cys Phe Glu Gly<br>65                  70                  75                  80 | | 240 |
| ggc gca ggc aac tgc agt tcg cac ggt ggc aac ggc ggc aac ggc ggc<br>Gly Ala Gly Asn Cys Ser Ser His Gly Gly Asn Gly Gly Asn Gly Gly<br>                85                  90                  95 | | 288 |
| agc gac cac cct ggg gga ggc cgc gaa ttc ttc ttc gat cgc cac cca<br>Ser Asp His Pro Gly Gly Gly Arg Glu Phe Phe Phe Asp Arg His Pro<br>            100                 105                 110 | | 336 |
| gga gta ttc gcc tat gtg ctc aat tac tac cgc acg ggc aag ctg cac<br>Gly Val Phe Ala Tyr Val Leu Asn Tyr Tyr Arg Thr Gly Lys Leu His<br>        115                 120                 125 | | 384 |
| tgc ccc gcc gac gtg tgc ggg ccg ctc ttc gag gaa gag ctg gct ttc<br>Cys Pro Ala Asp Val Cys Gly Pro Leu Phe Glu Glu Glu Leu Ala Phe<br>    130                 135                 140 | | 432 |
| tgg ggc atc gat gag acc gac gtg gag ccc tgc tgc tgg atg acc tac<br>Trp Gly Ile Asp Glu Thr Asp Val Glu Pro Cys Cys Trp Met Thr Tyr<br>145                 150                 155                 160 | | 480 |
| agg cag cac cgg gac gcg gag gag gcc ctg gac atc ttt gag aca ccc<br>Arg Gln His Arg Asp Ala Glu Glu Ala Leu Asp Ile Phe Glu Thr Pro<br>                165                 170                 175 | | 528 |
| gac ctc atc ggg ggc gac cct ggt gat gat gag gac cta gcg gcc aag<br>Asp Leu Ile Gly Gly Asp Pro Gly Asp Asp Glu Asp Leu Ala Ala Lys<br>            180                 185                 190 | | 576 |
| aga ttg ggc att gag gat gct gcg ggg ctg gga gga ccc gat ggc aag<br>Arg Leu Gly Ile Glu Asp Ala Ala Gly Leu Gly Gly Pro Asp Gly Lys<br>        195                 200                 205 | | 624 |
| tca ggc cgc tgg agg aag ctg cag cct cgc atg tgg gct ctt ttt gag<br>Ser Gly Arg Trp Arg Lys Leu Gln Pro Arg Met Trp Ala Leu Phe Glu<br>    210                 215                 220 | | 672 |
| gac ccc tac tca tct aga gcc gct agg ttt att gct ttt gct tct ttg<br>Asp Pro Tyr Ser Ser Arg Ala Ala Arg Phe Ile Ala Phe Ala Ser Leu<br>225                 230                 235                 240 | | 720 |
| ttc ttc att ttg gtt tcc atc aca acc ttt tgc ctg gag aca cat gaa<br>Phe Phe Ile Leu Val Ser Ile Thr Thr Phe Cys Leu Glu Thr His Glu<br>                245                 250                 255 | | 768 |
| gct ttc aat att gtt aaa aac aag acg gag ccc gtc atc aat ggc acc<br>Ala Phe Asn Ile Val Lys Asn Lys Thr Glu Pro Val Ile Asn Gly Thr<br>            260                 265                 270 | | 816 |
| agc ccg gtc ctc cag tac gaa atc gaa acg gat ccc gcc ctg acg tac<br>Ser Pro Val Leu Gln Tyr Glu Ile Glu Thr Asp Pro Ala Leu Thr Tyr<br>        275                 280                 285 | | 864 |
| gtg gaa gga gta tgt gtg gtg tgg ttt acg ttt gaa ttt tta gtc cga<br>Val Glu Gly Val Cys Val Val Trp Phe Thr Phe Glu Phe Leu Val Arg<br>    290                 295                 300 | | 912 |
| att gtt ttc tca ccc aat aaa ctt gaa ttc atc aaa aat ctc ttg aac<br>Ile Val Phe Ser Pro Asn Lys Leu Glu Phe Ile Lys Asn Leu Leu Asn | | 960 |

-continued

| | | | | | | | | | | | | | | |
|---|---|---|---|---|---|---|---|---|---|---|---|---|---|---|
| 305 | | | | | 310 | | | | | 315 | | | | 320 |
| atc | att | gac | ttt | gtg | gcc | atc | ctc | ccc | ttc | tac | cta | gag | gtg | gga | ctc | 1008 |
| Ile | Ile | Asp | Phe | Val | Ala | Ile | Leu | Pro | Phe | Tyr | Leu | Glu | Val | Gly | Leu |
| | | | | | 325 | | | | | 330 | | | | | 335 |
| agc | ggg | ctg | tcc | tcc | aaa | gcg | gcc | aaa | gat | gtg | ctc | ggc | ttt | ctc | agg | 1056 |
| Ser | Gly | Leu | Ser | Ser | Lys | Ala | Ala | Lys | Asp | Val | Leu | Gly | Phe | Leu | Arg |
| | | | 340 | | | | | 345 | | | | | 350 | | |
| gtg | gtt | agg | ttt | gtg | agg | atc | ctg | aga | atc | ttc | aag | ctc | acc | cgc | cat | 1104 |
| Val | Val | Arg | Phe | Val | Arg | Ile | Leu | Arg | Ile | Phe | Lys | Leu | Thr | Arg | His |
| | | 355 | | | | | 360 | | | | | 365 | | | |
| ttc | gta | ggt | ctg | agg | gtg | ctc | gga | cat | act | ctt | cgg | gcg | agc | acc | aac | 1152 |
| Phe | Val | Gly | Leu | Arg | Val | Leu | Gly | His | Thr | Leu | Arg | Ala | Ser | Thr | Asn |
| | 370 | | | | | 375 | | | | | 380 | | | | |
| gaa | ttt | ttg | ttg | ctg | atc | atc | ttc | ctg | gcg | ctg | gga | gtt | ttg | ata | ttc | 1200 |
| Glu | Phe | Leu | Leu | Leu | Ile | Ile | Phe | Leu | Ala | Leu | Gly | Val | Leu | Ile | Phe |
| 385 | | | | | 390 | | | | | 395 | | | | | 400 |
| gct | acg | atg | atc | tac | tac | gct | gag | aga | gta | ggg | gct | cag | ccc | aat | gac | 1248 |
| Ala | Thr | Met | Ile | Tyr | Tyr | Ala | Glu | Arg | Val | Gly | Ala | Gln | Pro | Asn | Asp |
| | | | | 405 | | | | | 410 | | | | | 415 | |
| cct | tca | gct | agt | gag | cac | acg | cag | ttc | aaa | aac | atc | ccc | att | ggt | ttc | 1296 |
| Pro | Ser | Ala | Ser | Glu | His | Thr | Gln | Phe | Lys | Asn | Ile | Pro | Ile | Gly | Phe |
| | | | 420 | | | | | 425 | | | | | 430 | | |
| tgg | tgg | gcc | gta | gtg | acc | atg | act | acc | tta | ggt | tac | ggg | gat | atg | tac | 1344 |
| Trp | Trp | Ala | Val | Val | Thr | Met | Thr | Thr | Leu | Gly | Tyr | Gly | Asp | Met | Tyr |
| | | 435 | | | | | 440 | | | | | 445 | | | |
| ccc | caa | aca | tgg | tca | ggg | atg | ttg | gtg | ggg | gcc | ttg | tgt | gcc | ctg | gcc | 1392 |
| Pro | Gln | Thr | Trp | Ser | Gly | Met | Leu | Val | Gly | Ala | Leu | Cys | Ala | Leu | Ala |
| | 450 | | | | | 455 | | | | | 460 | | | | |
| gga | gtg | ctg | aca | ata | gcc | atg | cct | gtg | cct | gtc | att | gtc | aac | aat | ttt | 1440 |
| Gly | Val | Leu | Thr | Ile | Ala | Met | Pro | Val | Pro | Val | Ile | Val | Asn | Asn | Phe |
| 465 | | | | | 470 | | | | | 475 | | | | | 480 |
| gga | atg | tac | tac | tcc | ttg | gca | atg | gcg | aag | cag | aaa | ctt | cca | aga | aag | 1488 |
| Gly | Met | Tyr | Tyr | Ser | Leu | Ala | Met | Ala | Lys | Gln | Lys | Leu | Pro | Arg | Lys |
| | | | | 485 | | | | | 490 | | | | | 495 | |
| aga | aag | aag | cat | att | cct | cct | gcc | cct | ctg | gca | agc | tcg | cct | aca | ttt | 1536 |
| Arg | Lys | Lys | His | Ile | Pro | Pro | Ala | Pro | Leu | Ala | Ser | Ser | Pro | Thr | Phe |
| | | | 500 | | | | | 505 | | | | | 510 | | |
| tgc | aag | aca | gaa | ttg | aac | atg | gct | tgc | aac | agt | acc | cag | agt | gac | aca | 1584 |
| Cys | Lys | Thr | Glu | Leu | Asn | Met | Ala | Cys | Asn | Ser | Thr | Gln | Ser | Asp | Thr |
| | | 515 | | | | | 520 | | | | | 525 | | | |
| tgt | ctg | ggc | aaa | gaa | aac | cgg | ctt | ctg | gaa | cat | aac | aga | tca | gtg | tta | 1632 |
| Cys | Leu | Gly | Lys | Glu | Asn | Arg | Leu | Leu | Glu | His | Asn | Arg | Ser | Val | Leu |
| | 530 | | | | | 535 | | | | | 540 | | | | |
| tca | ggt | gac | gac | agt | aca | gga | agt | gag | ccg | cca | tta | tca | cct | cca | gaa | 1680 |
| Ser | Gly | Asp | Asp | Ser | Thr | Gly | Ser | Glu | Pro | Pro | Leu | Ser | Pro | Pro | Glu |
| 545 | | | | | 550 | | | | | 555 | | | | | 560 |
| agg | ctc | cct | atc | aga | cgc | tct | agt | acc | aga | gac | aaa | aac | aga | aga | ggg | 1728 |
| Arg | Leu | Pro | Ile | Arg | Arg | Ser | Ser | Thr | Arg | Asp | Lys | Asn | Arg | Arg | Gly |
| | | | | 565 | | | | | 570 | | | | | 575 | |
| gaa | acg | tgt | ttc | ctg | ttg | acg | aca | ggt | gat | tac | acg | tgc | gct | tct | gat | 1776 |
| Glu | Thr | Cys | Phe | Leu | Leu | Thr | Thr | Gly | Asp | Tyr | Thr | Cys | Ala | Ser | Asp |
| | | | | | 580 | | | | | 585 | | | | | 590 |
| gga | gga | atc | agg | aaa | gca | agc | aca | cta | gag | ccc | atg | gag | agt | act | gca | 1824 |
| Gly | Gly | Ile | Arg | Lys | Ala | Ser | Thr | Leu | Glu | Pro | Met | Glu | Ser | Thr | Ala |
| | | | | 595 | | | | | 600 | | | | | 605 | |
| cag | act | aaa | gga | gac | aca | aga | cca | gaa | gct | cat | tgg | aat | tgt | gcg | cac | 1872 |
| Gln | Thr | Lys | Gly | Asp | Thr | Arg | Pro | Glu | Ala | His | Trp | Asn | Cys | Ala | His |
| | | 610 | | | | | 615 | | | | | 620 | | | |
| tta | ctc | aat | ttt | ggg | tgt | cct | aca | gga | agt | tca | ttt | ccc | acc | ctc | taa | 1920 |

```
Leu Leu Asn Phe Gly Cys Pro Thr Gly Ser Ser Phe Pro Thr Leu
625                 630                 635

<210> SEQ ID NO 10
<211> LENGTH: 639
<212> TYPE: PRT
<213> ORGANISM: Mus musculus

<400> SEQUENCE: 10

Met Gly Lys Ile Glu Ser Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
50                  55                  60

Pro Arg Pro Pro Leu Ser Pro Val Pro Ser Gly Cys Phe Glu Gly
65                  70                  75                  80

Gly Ala Gly Asn Cys Ser Ser His Gly Gly Asn Gly Gly Asn Gly Gly
                85                  90                  95

Ser Asp His Pro Gly Gly Gly Arg Glu Phe Phe Asp Arg His Pro
                100                 105                 110

Gly Val Phe Ala Tyr Val Leu Asn Tyr Tyr Arg Thr Gly Lys Leu His
            115                 120                 125

Cys Pro Ala Asp Val Cys Gly Pro Leu Phe Glu Glu Glu Leu Ala Phe
        130                 135                 140

Trp Gly Ile Asp Glu Thr Asp Val Glu Pro Cys Cys Trp Met Thr Tyr
145                 150                 155                 160

Arg Gln His Arg Asp Ala Glu Glu Ala Leu Asp Ile Phe Glu Thr Pro
                165                 170                 175

Asp Leu Ile Gly Gly Asp Pro Gly Asp Asp Glu Asp Leu Ala Ala Lys
            180                 185                 190

Arg Leu Gly Ile Glu Asp Ala Ala Gly Leu Gly Gly Pro Asp Gly Lys
        195                 200                 205

Ser Gly Arg Trp Arg Lys Leu Gln Pro Arg Met Trp Ala Leu Phe Glu
210                 215                 220

Asp Pro Tyr Ser Ser Arg Ala Ala Arg Phe Ile Ala Phe Ala Ser Leu
225                 230                 235                 240

Phe Phe Ile Leu Val Ser Ile Thr Thr Phe Cys Leu Glu Thr His Glu
                245                 250                 255

Ala Phe Asn Ile Val Lys Asn Lys Thr Glu Pro Val Ile Asn Gly Thr
            260                 265                 270

Ser Pro Val Leu Gln Tyr Glu Ile Glu Thr Asp Pro Ala Leu Thr Tyr
        275                 280                 285

Val Glu Gly Val Cys Val Val Trp Phe Thr Phe Glu Phe Leu Val Arg
    290                 295                 300

Ile Val Phe Ser Pro Asn Lys Leu Glu Phe Ile Lys Asn Leu Leu Asn
305                 310                 315                 320

Ile Ile Asp Phe Val Ala Ile Leu Pro Phe Tyr Leu Glu Val Gly Leu
                325                 330                 335

Ser Gly Leu Ser Ser Lys Ala Ala Lys Asp Val Leu Gly Phe Leu Arg
            340                 345                 350

Val Val Arg Phe Val Arg Ile Leu Arg Ile Phe Lys Leu Thr Arg His
        355                 360                 365
```

```
Phe Val Gly Leu Arg Val Leu Gly His Thr Leu Arg Ala Ser Thr Asn
    370                 375                 380

Glu Phe Leu Leu Leu Ile Ile Phe Leu Ala Leu Gly Val Leu Ile Phe
385                 390                 395                 400

Ala Thr Met Ile Tyr Tyr Ala Glu Arg Val Gly Ala Gln Pro Asn Asp
                405                 410                 415

Pro Ser Ala Ser Glu His Thr Gln Phe Lys Asn Ile Pro Ile Gly Phe
                420                 425                 430

Trp Trp Ala Val Val Thr Met Thr Thr Leu Gly Tyr Gly Asp Met Tyr
                435                 440                 445

Pro Gln Thr Trp Ser Gly Met Leu Val Gly Ala Leu Cys Ala Leu Ala
        450                 455                 460

Gly Val Leu Thr Ile Ala Met Pro Val Pro Val Ile Val Asn Asn Phe
465                 470                 475                 480

Gly Met Tyr Tyr Ser Leu Ala Met Ala Lys Gln Lys Leu Pro Arg Lys
                485                 490                 495

Arg Lys Lys His Ile Pro Pro Ala Pro Leu Ala Ser Ser Pro Thr Phe
            500                 505                 510

Cys Lys Thr Glu Leu Asn Met Ala Cys Asn Ser Thr Gln Ser Asp Thr
            515                 520                 525

Cys Leu Gly Lys Glu Asn Arg Leu Leu Glu His Asn Arg Ser Val Leu
        530                 535                 540

Ser Gly Asp Asp Ser Thr Gly Ser Glu Pro Pro Leu Ser Pro Pro Glu
545                 550                 555                 560

Arg Leu Pro Ile Arg Arg Ser Ser Thr Arg Asp Lys Asn Arg Arg Gly
                565                 570                 575

Glu Thr Cys Phe Leu Leu Thr Thr Gly Asp Tyr Thr Cys Ala Ser Asp
                580                 585                 590

Gly Gly Ile Arg Lys Ala Ser Thr Leu Glu Pro Met Glu Ser Thr Ala
            595                 600                 605

Gln Thr Lys Gly Asp Thr Arg Pro Glu Ala His Trp Asn Cys Ala His
            610                 615                 620

Leu Leu Asn Phe Gly Cys Pro Thr Gly Ser Ser Phe Pro Thr Leu
625                 630                 635

<210> SEQ ID NO 11
<211> LENGTH: 1842
<212> TYPE: DNA
<213> ORGANISM: Rattus norvegicus
<220> FEATURE:
<221> NAME/KEY: CDS
<222> LOCATION: (1)..(1839)

<400> SEQUENCE: 11 atg ggc aag atc gag aac aac gag agg gtg atc ctc aat gtc gga ggc     48
Met Gly Lys Ile Glu Asn Asn Glu Arg Val Ile Leu Asn Val Gly Gly
1               5                   10                  15 acc agg cac gaa acc tac cgc agc act ctc aag acc ctt cct gga act     96
Thr Arg His Glu Thr Tyr Arg Ser Thr Leu Lys Thr Leu Pro Gly Thr
            20                  25                  30 cgc ctg gcc ctt ctc gcc tcc tct gaa cct cag ggc gac tgc ctg act    144
Arg Leu Ala Leu Leu Ala Ser Ser Glu Pro Gln Gly Asp Cys Leu Thr
        35                  40                  45 gct gcg ggt gac aag ctg cag ccg ctg ccc cct ccg ctg tct cca ccg    192
Ala Ala Gly Asp Lys Leu Gln Pro Leu Pro Pro Pro Leu Ser Pro Pro
    50                  55                  60
```

```
ccg cga ccg cct ccc ttg tcc cct gtc ccc agc ggc tgc ttc gag ggc        240
Pro Arg Pro Pro Pro Leu Ser Pro Val Pro Ser Gly Cys Phe Glu Gly
 65              70                  75                  80 ggc gca ggc aac tgc agt tcg cac ggt ggc aat ggc agc gac cac cct        288
Gly Ala Gly Asn Cys Ser Ser His Gly Gly Asn Gly Ser Asp His Pro
                 85                  90                  95 ggg gga ggc cgc gaa ttc ttc ttc gat cgc cac cca gga gtc ttc gcc        336
Gly Gly Gly Arg Glu Phe Phe Phe Asp Arg His Pro Gly Val Phe Ala
                100                 105                 110 tat gtg ctc aac tac tac cgc acg ggc aag ctg cac tgc ccc gcc gac        384
Tyr Val Leu Asn Tyr Tyr Arg Thr Gly Lys Leu His Cys Pro Ala Asp
                115                 120                 125 gtg tgt gga ccg ctc ttc gag gaa gag ctg gca ttc tgg ggc atc gat        432
Val Cys Gly Pro Leu Phe Glu Glu Glu Leu Ala Phe Trp Gly Ile Asp
    130                 135                 140 gag acc gac gtg gag ccc tgc tgc tgg atg acc tac agg cag cac cgg        480
Glu Thr Asp Val Glu Pro Cys Cys Trp Met Thr Tyr Arg Gln His Arg
145                 150                 155                 160 gac gcg gag gag gcc ctg gat atc ttc gag aca ccc gac ctc atc gga        528
Asp Ala Glu Glu Ala Leu Asp Ile Phe Glu Thr Pro Asp Leu Ile Gly
                165                 170                 175 ggc gac cct ggt gat gat gag gac cta ggg ggc aag aga ctg ggc att        576
Gly Asp Pro Gly Asp Asp Glu Asp Leu Gly Gly Lys Arg Leu Gly Ile
                180                 185                 190 gag gat gct gcg ggg ctg gga gga ccc gat ggc aag tct ggc cgc tgg        624
Glu Asp Ala Ala Gly Leu Gly Gly Pro Asp Gly Lys Ser Gly Arg Trp
                195                 200                 205 agg aag ctg cag cct cgc atg tgg gct ctc ttt gag gac ccc tat tca        672
Arg Lys Leu Gln Pro Arg Met Trp Ala Leu Phe Glu Asp Pro Tyr Ser
    210                 215                 220 tcc aga gcc gct agg ttt att gct ttt gct tct ctg ttc ttc att ttg        720
Ser Arg Ala Ala Arg Phe Ile Ala Phe Ala Ser Leu Phe Phe Ile Leu
225                 230                 235                 240 gtt tcc atc aca acc ttt tgc ctg gag aca cac gaa gct ttc aat att        768
Val Ser Ile Thr Thr Phe Cys Leu Glu Thr His Glu Ala Phe Asn Ile
                245                 250                 255 gtt aaa aac aag aca gag cca gtc atc aac ggc acc agc gct gtt ctc        816
Val Lys Asn Lys Thr Glu Pro Val Ile Asn Gly Thr Ser Ala Val Leu
                260                 265                 270 cag tat gaa atc gaa acg gat cct gcc ttg aca tat gtg gaa gga gtg        864
Gln Tyr Glu Ile Glu Thr Asp Pro Ala Leu Thr Tyr Val Glu Gly Val
                275                 280                 285 tgt gtg gtg tgg ttt act ttt gaa ttt tta gtc cgt att gtt ttc tcg        912
Cys Val Val Trp Phe Thr Phe Glu Phe Leu Val Arg Ile Val Phe Ser
    290                 295                 300 ccc aat aaa ctt gag ttc atc aaa aat cta ttg aac atc att gac ttt        960
Pro Asn Lys Leu Glu Phe Ile Lys Asn Leu Leu Asn Ile Ile Asp Phe
305                 310                 315                 320 gtg gcc atc ctc ccc ttc tac tta gag gtg gga ctc agc ggg ctg tct       1008
Val Ala Ile Leu Pro Phe Tyr Leu Glu Val Gly Leu Ser Gly Leu Ser
                325                 330                 335 tcc aaa gcg gct aaa gat gtg ctc ggc ttt ctc agg gtg gtt agg ttt       1056
Ser Lys Ala Ala Lys Asp Val Leu Gly Phe Leu Arg Val Val Arg Phe
                340                 345                 350 gtg agg atc ctg aga atc ttc aag ctt acc cgc cat ttc gta ggt ctg       1104
Val Arg Ile Leu Arg Ile Phe Lys Leu Thr Arg His Phe Val Gly Leu
    355                 360                 365 aga gtg ctc gga cac act ctt cgt gcg agc acc aat gaa ttt ttg ttg       1152
Arg Val Leu Gly His Thr Leu Arg Ala Ser Thr Asn Glu Phe Leu Leu
                370                 375                 380
```

-continued

```
ctg atc atc ttt ctg gct ctg gga gtt ttg ata ttc gct acg atg atc     1200
Leu Ile Ile Phe Leu Ala Leu Gly Val Leu Ile Phe Ala Thr Met Ile
385                 390                 395                 400 tac tac gct gag cga gta ggg gct caa cct aat gat ccc tca gcg agt     1248
Tyr Tyr Ala Glu Arg Val Gly Ala Gln Pro Asn Asp Pro Ser Ala Ser
            405                 410                 415 gag cac aca cag ttc aaa aac atc ccc att ggt ttc tgg tgg gct gtg     1296
Glu His Thr Gln Phe Lys Asn Ile Pro Ile Gly Phe Trp Trp Ala Val
420                 425                 430 gtg acc atg act acc tta ggc tat ggg gat atg tac ccc caa aca tgg     1344
Val Thr Met Thr Thr Leu Gly Tyr Gly Asp Met Tyr Pro Gln Thr Trp
        435                 440                 445 tca ggg atg ttg gtg ggg gcc ttg tgt gct ctg gct gga gtg ctg acc     1392
Ser Gly Met Leu Val Gly Ala Leu Cys Ala Leu Ala Gly Val Leu Thr
    450                 455                 460 ata gct atg cct gtg ccc gtc att gtc aac aat ttt ggg atg tac tac     1440
Ile Ala Met Pro Val Pro Val Ile Val Asn Asn Phe Gly Met Tyr Tyr
465                 470                 475                 480 tcc ttg gca atg gcg aag cag aaa ctt cca aga aaa aga aag aag cac     1488
Ser Leu Ala Met Ala Lys Gln Lys Leu Pro Arg Lys Arg Lys Lys His
            485                 490                 495 att cct cct gcc cct ctg gca agc tca cct aca ttt tgc aag aca gaa     1536
Ile Pro Pro Ala Pro Leu Ala Ser Ser Pro Thr Phe Cys Lys Thr Glu
        500                 505                 510 tta aac atg gct tgt aac agt acc cag agt gac aca tgt ctg ggc aaa     1584
Leu Asn Met Ala Cys Asn Ser Thr Gln Ser Asp Thr Cys Leu Gly Lys
    515                 520                 525 gaa aac cgg ctt ctg gaa cat aac aga tca gtg tta tca ggt gac gac     1632
Glu Asn Arg Leu Leu Glu His Asn Arg Ser Val Leu Ser Gly Asp Asp
530                 535                 540 agt aca gga agt gag ccg cca tta tca cct ccg gaa agg ctc ccc atc     1680
Ser Thr Gly Ser Glu Pro Pro Leu Ser Pro Pro Glu Arg Leu Pro Ile
545                 550                 555                 560 aga cgc tct agt acc aga gac aaa aac aga aga ggg gaa aca tgt ttc     1728
Arg Arg Ser Ser Thr Arg Asp Lys Asn Arg Arg Gly Glu Thr Cys Phe
            565                 570                 575 ctg ttg acg aca ggt gat tac acg tgc gct tct gat gga gga atc agg     1776
Leu Leu Thr Thr Gly Asp Tyr Thr Cys Ala Ser Asp Gly Gly Ile Arg
        580                 585                 590 aaa gat aac tgc aaa gat gtt gtc att act ggt tac acg caa gcc gag     1824
Lys Asp Asn Cys Lys Asp Val Val Ile Thr Gly Tyr Thr Gln Ala Glu
    595                 600                 605 gcc aga tct ctt act taa                                              1842
Ala Arg Ser Leu Thr
    610

<210> SEQ ID NO 12
<211> LENGTH: 613
<212> TYPE: PRT
<213> ORGANISM: Rattus norvegicus

<400> SEQUENCE: 12

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Pro Leu Ser Pro Pro
```

```
                50                  55                  60
Pro Arg Pro Pro Leu Ser Pro Val Pro Ser Gly Cys Phe Glu Gly
 65                  70                  75                  80

Gly Ala Gly Asn Cys Ser Ser His Gly Gly Asn Gly Ser Asp His Pro
                 85                  90                  95

Gly Gly Gly Arg Glu Phe Phe Phe Asp Arg His Pro Gly Val Phe Ala
                100                 105                 110

Tyr Val Leu Asn Tyr Tyr Arg Thr Gly Lys Leu His Cys Pro Ala Asp
                115                 120                 125

Val Cys Gly Pro Leu Phe Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Gly Gly Lys Arg Leu Gly Ile
                180                 185                 190

Glu Asp Ala Ala Gly Leu Gly Gly Pro Asp Gly Lys Ser Gly Arg Trp
                195                 200                 205

Arg Lys Leu Gln Pro Arg Met Trp Ala Leu Phe Glu Asp Pro Tyr Ser
210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Ala Val Leu
                260                 265                 270

Gln Tyr Glu Ile Glu Thr Asp Pro Ala Leu Thr Tyr Val Glu Gly Val
                275                 280                 285

Cys Val Val Trp Phe Thr Phe Glu Phe Leu Val Arg Ile Val Phe Ser
                290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
                340                 345                 350

Val Arg Ile Leu Arg Ile Phe Lys Leu Thr Arg His Phe Val Gly Leu
                355                 360                 365

Arg Val Leu Gly His Thr Leu Arg Ala Ser Thr Asn Glu Phe Leu Leu
                370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
                420                 425                 430

Val Thr Met Thr Thr Leu Gly Tyr Gly Asp Met Tyr Pro Gln Thr Trp
                435                 440                 445

Ser Gly Met Leu Val Gly Ala Leu Cys Ala Leu Ala Gly Val Leu Thr
                450                 455                 460

Ile Ala Met Pro Val Pro Val Ile Val Asn Asn Phe Gly Met Tyr Tyr
465                 470                 475                 480
```

-continued

```
Ser Leu Ala Met Ala Lys Gln Lys Leu Pro Arg Lys Arg Lys Lys His
            485                 490                 495
Ile Pro Pro Ala Pro Leu Ala Ser Ser Pro Thr Phe Cys Lys Thr Glu
            500                 505                 510
Leu Asn Met Ala Cys Asn Ser Thr Gln Ser Asp Thr Cys Leu Gly Lys
            515                 520                 525
Glu Asn Arg Leu Leu Glu His Asn Arg Ser Val Leu Ser Gly Asp Asp
            530                 535                 540
Ser Thr Gly Ser Glu Pro Pro Leu Ser Pro Pro Glu Arg Leu Pro Ile
545                 550                 555                 560
Arg Arg Ser Ser Thr Arg Asp Lys Asn Arg Arg Gly Glu Thr Cys Phe
                565                 570                 575
Leu Leu Thr Thr Gly Asp Tyr Thr Cys Ala Ser Asp Gly Gly Ile Arg
            580                 585                 590
Lys Asp Asn Cys Lys Asp Val Val Ile Thr Gly Tyr Thr Gln Ala Glu
            595                 600                 605
Ala Arg Ser Leu Thr
        610
```

<210> SEQ ID NO 13
<211> LENGTH: 1917
<212> TYPE: DNA
<213> ORGANISM: Rattus norvegicus
<220> FEATURE:
<221> NAME/KEY: CDS
<222> LOCATION: (1)..(1914)

<400> SEQUENCE: 13

```
atg ggc aag atc gag aac aac gag agg gtg atc ctc aat gtc gga ggc      48
Met Gly Lys Ile Glu Asn Asn Glu Arg Val Ile Leu Asn Val Gly Gly
1               5                   10                  15 acc agg cac gaa acc tac cgc agc act ctc aag acc ctt cct gga act      96
Thr Arg His Glu Thr Tyr Arg Ser Thr Leu Lys Thr Leu Pro Gly Thr
                20                  25                  30 cgc ctg gcc ctt ctc gcc tcc tct gaa cct cag ggc gac tgc ctg act     144
Arg Leu Ala Leu Leu Ala Ser Ser Glu Pro Gln Gly Asp Cys Leu Thr
            35                  40                  45 gct gcg ggt gac aag ctg cag ccg ctg ccc cct ccg ctg tct cca ccg     192
Ala Ala Gly Asp Lys Leu Gln Pro Leu Pro Pro Pro Leu Ser Pro Pro
        50                  55                  60 ccg cga ccg cct ccc ttg tcc cct gtc ccc agc ggc tgc ttc gag ggc     240
Pro Arg Pro Pro Pro Leu Ser Pro Val Pro Ser Gly Cys Phe Glu Gly
65                  70                  75                  80 ggc gca ggc aac tgc agt tcg cac ggt ggc aat ggc agc gac cac cct     288
Gly Ala Gly Asn Cys Ser Ser His Gly Gly Asn Gly Ser Asp His Pro
                85                  90                  95 ggg gga ggc cgc gaa ttc ttc ttc gat cgc cac cca gga gtc ttc gcc     336
Gly Gly Gly Arg Glu Phe Phe Phe Asp Arg His Pro Gly Val Phe Ala
            100                 105                 110 tat gtg ctc aac tac tac cgc acg ggc aag ctg cac tgc ccc gcc gac     384
Tyr Val Leu Asn Tyr Tyr Arg Thr Gly Lys Leu His Cys Pro Ala Asp
        115                 120                 125 gtg tgt gga ccg ctc ttc gag gaa gag ctg gca ttc tgg ggc atc gat     432
Val Cys Gly Pro Leu Phe Glu Glu Glu Leu Ala Phe Trp Gly Ile Asp
    130                 135                 140 gag acc gac gtg gag ccc tgc tgc tgg atg acc tac agg cag cac cgg     480
Glu Thr Asp Val Glu Pro Cys Cys Trp Met Thr Tyr Arg Gln His Arg
145                 150                 155                 160
```

```
gac gcg gag gag gcc ctg gat atc ttc gag aca ccc gac ctc atc gga        528
Asp Ala Glu Glu Ala Leu Asp Ile Phe Glu Thr Pro Asp Leu Ile Gly
            165                 170                 175 ggc gac cct ggt gat gat gag gac cta ggg ggc aag aga ctg ggc att        576
Gly Asp Pro Gly Asp Asp Glu Asp Leu Gly Gly Lys Arg Leu Gly Ile
            180                 185                 190 gag gat gct gcg ggg ctg gga gga ccc gat ggc aag tct ggc cgc tgg        624
Glu Asp Ala Ala Gly Leu Gly Gly Pro Asp Gly Lys Ser Gly Arg Trp
            195                 200                 205 agg aag ctg cag cct cgc atg tgg gct ctc ttt gag gac ccc tat tca        672
Arg Lys Leu Gln Pro Arg Met Trp Ala Leu Phe Glu Asp Pro Tyr Ser
            210                 215                 220 tcc aga gcc gct agg ttt att gct ttt gct tct ctg ttc ttc att ttg        720
Ser Arg Ala Ala Arg Phe Ile Ala Phe Ala Ser Leu Phe Phe Ile Leu
225                 230                 235                 240 gtt tcc atc aca acc ttt tgc ctg gag aca cac gaa gct ttc aat att        768
Val Ser Ile Thr Thr Phe Cys Leu Glu Thr His Glu Ala Phe Asn Ile
                245                 250                 255 gtt aaa aac aag aca gag cca gtc atc aac ggc acc agc gct gtt ctc        816
Val Lys Asn Lys Thr Glu Pro Val Ile Asn Gly Thr Ser Ala Val Leu
            260                 265                 270 cag tat gaa atc gaa acg gat cct gcc ttg aca tat gtg gaa gga gtg        864
Gln Tyr Glu Ile Glu Thr Asp Pro Ala Leu Thr Tyr Val Glu Gly Val
            275                 280                 285 tgt gtg gtg tgg ttt act ttt gaa ttt tta gtc cgt att gtt ttc tcg        912
Cys Val Val Trp Phe Thr Phe Glu Phe Leu Val Arg Ile Val Phe Ser
            290                 295                 300 ccc aat aaa ctt gag ttc atc aaa aat cta ttg aac atc att gac ttt        960
Pro Asn Lys Leu Glu Phe Ile Lys Asn Leu Leu Asn Ile Ile Asp Phe
305                 310                 315                 320 gtg gcc atc ctc ccc ttc tac tta gag gtg gga ctc agc ggg ctg tct       1008
Val Ala Ile Leu Pro Phe Tyr Leu Glu Val Gly Leu Ser Gly Leu Ser
                325                 330                 335 tcc aaa gcg gct aaa gat gtg ctc ggc ttt ctc agg gtg gtt agg ttt       1056
Ser Lys Ala Ala Lys Asp Val Leu Gly Phe Leu Arg Val Val Arg Phe
            340                 345                 350 gtg agg atc ctg aga atc ttc aag ctt acc cgc cat ttc gta ggt ctg       1104
Val Arg Ile Leu Arg Ile Phe Lys Leu Thr Arg His Phe Val Gly Leu
            355                 360                 365 aga gtg ctc gga cac act ctt cgt gcg agc acc aat gaa ttt ttg ttg       1152
Arg Val Leu Gly His Thr Leu Arg Ala Ser Thr Asn Glu Phe Leu Leu
            370                 375                 380 ctg atc atc ttt ctg gct ctg gga gtt ttg ata ttc gct acg atg atc       1200
Leu Ile Ile Phe Leu Ala Leu Gly Val Leu Ile Phe Ala Thr Met Ile
385                 390                 395                 400 tac tac gct gag cga gta ggg gct caa cct aat gat ccc tca gcg agt       1248
Tyr Tyr Ala Glu Arg Val Gly Ala Gln Pro Asn Asp Pro Ser Ala Ser
                405                 410                 415 gag cac aca cag ttc aaa aac atc ccc att ggt ttc tgg tgg gct gtg       1296
Glu His Thr Gln Phe Lys Asn Ile Pro Ile Gly Phe Trp Trp Ala Val
            420                 425                 430 gtg acc atg act acc tta ggc tat ggg gat atg tac ccc caa aca tgg       1344
Val Thr Met Thr Thr Leu Gly Tyr Gly Asp Met Tyr Pro Gln Thr Trp
            435                 440                 445 tca ggg atg ttg gtg ggg gcc ttg tgt gct ctg gct gga gtg ctg acc       1392
Ser Gly Met Leu Val Gly Ala Leu Cys Ala Leu Ala Gly Val Leu Thr
450                 455                 460 ata gct atg cct gtg ccc gtc att gtc aac aat ttt ggg atg tac tac       1440
Ile Ala Met Pro Val Pro Val Ile Val Asn Asn Phe Gly Met Tyr Tyr
465                 470                 475                 480
```

```
tcc ttg gca atg gcg aag cag aaa ctt cca aga aaa aga aag aag cac    1488
Ser Leu Ala Met Ala Lys Gln Lys Leu Pro Arg Lys Arg Lys Lys His
            485                 490                 495 att cct cct gcc cct ctg gca agc tca cct aca ttt tgc aag aca gaa    1536
Ile Pro Pro Ala Pro Leu Ala Ser Ser Pro Thr Phe Cys Lys Thr Glu
        500                 505                 510 tta aac atg gct tgt aac agt acc cag agt gac aca tgt ctg ggc aaa    1584
Leu Asn Met Ala Cys Asn Ser Thr Gln Ser Asp Thr Cys Leu Gly Lys
            515                 520                 525 gaa aac cgg ctt ctg gaa cat aac aga tca gtg tta tca ggt gac gac    1632
Glu Asn Arg Leu Leu Glu His Asn Arg Ser Val Leu Ser Gly Asp Asp
530                 535                 540 agt aca gga agt gag ccg cca tta tca cct ccg gaa agg ctc ccc atc    1680
Ser Thr Gly Ser Glu Pro Pro Leu Ser Pro Pro Glu Arg Leu Pro Ile
545                 550                 555                 560 aga cgc tct agt acc aga gac aaa aac aga aga ggg gaa aca tgt ttc    1728
Arg Arg Ser Ser Thr Arg Asp Lys Asn Arg Arg Gly Glu Thr Cys Phe
                565                 570                 575 ctg ttg acg aca ggt gat tac acg tgc gct tct gat gga gga atc agg    1776
Leu Leu Thr Thr Gly Asp Tyr Thr Cys Ala Ser Asp Gly Gly Ile Arg
            580                 585                 590 aaa gga tat gaa aaa tcc cga agc tta aac aac ata gcg ggc ttg gca    1824
Lys Gly Tyr Glu Lys Ser Arg Ser Leu Asn Asn Ile Ala Gly Leu Ala
        595                 600                 605 ggc aat gct ctg aga ctc tct cca gta aca tcc ccc tac aac tct ccg    1872
Gly Asn Ala Leu Arg Leu Ser Pro Val Thr Ser Pro Tyr Asn Ser Pro
            610                 615                 620 tgt cct ctg agg cgc tct cgg tct ccc atc cca tct atc ttg taa        1917
Cys Pro Leu Arg Arg Ser Arg Ser Pro Ile Pro Ser Ile Leu
625                 630                 635

<210> SEQ ID NO 14
<211> LENGTH: 638
<212> TYPE: PRT
<213> ORGANISM: Rattus norvegicus

<400> SEQUENCE: 14

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
    50                  55                  60

Pro Arg Pro Pro Leu Ser Pro Val Pro Ser Gly Cys Phe Glu Gly
65                  70                  75                  80

Gly Ala Gly Asn Cys Ser Ser His Gly Gly Asn Gly Ser Asp His Pro
                85                  90                  95

Gly Gly Gly Arg Glu Phe Phe Asp Arg His Pro Gly Val Phe Ala
            100                 105                 110

Tyr Val Leu Asn Tyr Tyr Arg Thr Gly Lys Leu His Cys Pro Ala Asp
        115                 120                 125

Val Cys Gly Pro Leu Phe Glu Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160
```

```
Asp Ala Glu Glu Ala Leu Asp Ile Phe Glu Thr Pro Asp Leu Ile Gly
                165                 170                 175
Gly Asp Pro Gly Asp Glu Asp Leu Gly Gly Lys Arg Leu Gly Ile
        180                 185                 190
Glu Asp Ala Ala Gly Leu Gly Gly Pro Asp Gly Lys Ser Gly Arg Trp
        195                 200                 205
Arg Lys Leu Gln Pro Arg Met Trp Ala Leu Phe Glu Asp Pro Tyr Ser
    210                 215                 220
Ser Arg Ala Ala Arg Phe Ile Ala Phe Ala Ser Leu Phe Phe Ile Leu
225                 230                 235                 240
Val Ser Ile Thr Thr Phe Cys Leu Glu Thr His Glu Ala Phe Asn Ile
                245                 250                 255
Val Lys Asn Lys Thr Glu Pro Val Ile Asn Gly Thr Ser Ala Val Leu
        260                 265                 270
Gln Tyr Glu Ile Glu Thr Asp Pro Ala Leu Thr Tyr Val Glu Gly Val
    275                 280                 285
Cys Val Val Trp Phe Thr Phe Glu Phe Leu Val Arg Ile Val Phe Ser
    290                 295                 300
Pro Asn Lys Leu Glu Phe Ile Lys Asn Leu Leu Asn Ile Ile Asp Phe
305                 310                 315                 320
Val Ala Ile Leu Pro Phe Tyr Leu Glu Val Gly Leu Ser Gly Leu Ser
                325                 330                 335
Ser Lys Ala Ala Lys Asp Val Leu Gly Phe Leu Arg Val Val Arg Phe
        340                 345                 350
Val Arg Ile Leu Arg Ile Phe Lys Leu Thr Arg His Phe Val Gly Leu
        355                 360                 365
Arg Val Leu Gly His Thr Leu Arg Ala Ser Thr Asn Glu Phe Leu Leu
    370                 375                 380
Leu Ile Ile Phe Leu Ala Leu Gly Val Leu Ile Phe Ala Thr Met Ile
385                 390                 395                 400
Tyr Tyr Ala Glu Arg Val Gly Ala Gln Pro Asn Asp Pro Ser Ala Ser
                405                 410                 415
Glu His Thr Gln Phe Lys Asn Ile Pro Ile Gly Phe Trp Trp Ala Val
        420                 425                 430
Val Thr Met Thr Thr Leu Gly Tyr Gly Asp Met Tyr Pro Gln Thr Trp
        435                 440                 445
Ser Gly Met Leu Val Gly Ala Leu Cys Ala Leu Ala Gly Val Leu Thr
    450                 455                 460
Ile Ala Met Pro Val Pro Val Ile Val Asn Asn Phe Gly Met Tyr Tyr
465                 470                 475                 480
Ser Leu Ala Met Ala Lys Gln Lys Leu Pro Arg Lys Arg Lys Lys His
                485                 490                 495
Ile Pro Pro Ala Pro Leu Ala Ser Ser Pro Thr Phe Cys Lys Thr Glu
        500                 505                 510
Leu Asn Met Ala Cys Asn Ser Thr Gln Ser Asp Thr Cys Leu Gly Lys
        515                 520                 525
Glu Asn Arg Leu Leu Glu His Asn Arg Ser Val Leu Ser Gly Asp Asp
    530                 535                 540
Ser Thr Gly Ser Glu Pro Leu Ser Pro Glu Arg Leu Pro Ile
545                 550                 555                 560
Arg Arg Ser Ser Thr Arg Asp Lys Asn Arg Arg Gly Glu Thr Cys Phe
                565                 570                 575
Leu Leu Thr Thr Gly Asp Tyr Thr Cys Ala Ser Asp Gly Gly Ile Arg
```

-continued

```
                580                 585                 590
Lys Gly Tyr Glu Lys Ser Arg Ser Leu Asn Asn Ile Ala Gly Leu Ala
            595                 600                 605

Gly Asn Ala Leu Arg Leu Ser Pro Val Thr Ser Pro Tyr Asn Ser Pro
        610                 615                 620

Cys Pro Leu Arg Arg Ser Arg Ser Pro Ile Pro Ser Ile Leu
625                 630                 635

<210> SEQ ID NO 15
<211> LENGTH: 1908
<212> TYPE: DNA
<213> ORGANISM: Rattus norvegicus
<220> FEATURE:
<221> NAME/KEY: CDS
<222> LOCATION: (1)..(1905)

<400> SEQUENCE: 15 atg ggc aag atc gag aac aac gag agg gtg atc ctc aat gtc gga ggc      48
Met Gly Lys Ile Glu Asn Asn Glu Arg Val Ile Leu Asn Val Gly Gly
1               5                   10                  15 acc agg cac gaa acc tac cgc agc act ctc aag acc ctt cct gga act      96
Thr Arg His Glu Thr Tyr Arg Ser Thr Leu Lys Thr Leu Pro Gly Thr
            20                  25                  30 cgc ctg gcc ctt ctc gcc tcc tct gaa cct cag ggc gac tgc ctg act     144
Arg Leu Ala Leu Leu Ala Ser Ser Glu Pro Gln Gly Asp Cys Leu Thr
        35                  40                  45 gct gcg ggt gac aag ctg cag ccg ctg ccc cct ccg ctg tct cca ccg     192
Ala Ala Gly Asp Lys Leu Gln Pro Leu Pro Pro Pro Leu Ser Pro Pro
    50                  55                  60 ccg cga ccg cct ccc ttg tcc cct gtc ccc agc ggc tgc ttc gag ggc     240
Pro Arg Pro Pro Pro Leu Ser Pro Val Pro Ser Gly Cys Phe Glu Gly
65                  70                  75                  80 ggc gca ggc aac tgc agt tcg cac ggt ggc aat ggc agc gac cac cct     288
Gly Ala Gly Asn Cys Ser Ser His Gly Gly Asn Gly Ser Asp His Pro
                85                  90                  95 ggg gga ggc cgc gaa ttc ttc ttc gat cgc cac cca gga gtc ttc gcc     336
Gly Gly Gly Arg Glu Phe Phe Phe Asp Arg His Pro Gly Val Phe Ala
            100                 105                 110 tat gtg ctc aac tac tac cgc acg ggc aag ctg cac tgc ccc gcc gac     384
Tyr Val Leu Asn Tyr Tyr Arg Thr Gly Lys Leu His Cys Pro Ala Asp
        115                 120                 125 gtg tgt gga ccg ctc ttc gag gaa gag ctg gca ttc tgg ggc atc gat     432
Val Cys Gly Pro Leu Phe Glu Glu Glu Leu Ala Phe Trp Gly Ile Asp
    130                 135                 140 gag acc gac gtg gag ccc tgc tgc tgg atg acc tac agg cag cac cgg     480
Glu Thr Asp Val Glu Pro Cys Cys Trp Met Thr Tyr Arg Gln His Arg
145                 150                 155                 160 gac gcg gag gag gcc ctg gat atc ttc gag aca ccc gac ctc atc gga     528
Asp Ala Glu Glu Ala Leu Asp Ile Phe Glu Thr Pro Asp Leu Ile Gly
                165                 170                 175 ggc gac cct ggt gat gat gag gac cta ggg ggc aag aga ctg ggc att     576
Gly Asp Pro Gly Asp Asp Glu Asp Leu Gly Gly Lys Arg Leu Gly Ile
            180                 185                 190 gag gat gct gcg ggg ctg gga gga ccc gat ggc aag tct ggc cgc tgg     624
Glu Asp Ala Ala Gly Leu Gly Gly Pro Asp Gly Lys Ser Gly Arg Trp
        195                 200                 205 agg aag ctg cag cct cgc atg tgg gct ctc ttt gag gac ccc tat tca     672
Arg Lys Leu Gln Pro Arg Met Trp Ala Leu Phe Glu Asp Pro Tyr Ser
    210                 215                 220 tcc aga gcc gct agg ttt att gct ttt gct tct ctg ttc ttc att tg      720
```

```
            Ser Arg Ala Ala Arg Phe Ile Ala Phe Ala Ser Leu Phe Phe Ile Leu
            225                 230                 235                 240 gtt tcc atc aca acc ttt tgc ctg gag aca cac gaa gct ttc aat att            768
Val Ser Ile Thr Thr Phe Cys Leu Glu Thr His Glu Ala Phe Asn Ile
                    245                 250                 255 gtt aaa aac aag aca gag cca gtc atc aac ggc acc agc gct gtt ctc            816
Val Lys Asn Lys Thr Glu Pro Val Ile Asn Gly Thr Ser Ala Val Leu
                260                 265                 270 cag tat gaa atc gaa acg gat cct gcc ttg aca tat gtg gaa gga gtg            864
Gln Tyr Glu Ile Glu Thr Asp Pro Ala Leu Thr Tyr Val Glu Gly Val
            275                 280                 285 tgt gtg gtg tgg ttt act ttt gaa ttt tta gtc cgt att gtt ttc tcg            912
Cys Val Val Trp Phe Thr Phe Glu Phe Leu Val Arg Ile Val Phe Ser
        290                 295                 300 ccc aat aaa ctt gag ttc atc aaa aat cta ttg aac atc att gac ttt            960
Pro Asn Lys Leu Glu Phe Ile Lys Asn Leu Leu Asn Ile Ile Asp Phe
305                 310                 315                 320 gtg gcc atc ctc ccc ttc tac tta gag gtg gga ctc agc ggg ctg tct           1008
Val Ala Ile Leu Pro Phe Tyr Leu Glu Val Gly Leu Ser Gly Leu Ser
                325                 330                 335 tcc aaa gcg gct aaa gat gtg ctc ggc ttt ctc agg gtg gtt agg ttt           1056
Ser Lys Ala Ala Lys Asp Val Leu Gly Phe Leu Arg Val Val Arg Phe
            340                 345                 350 gtg agg atc ctg aga atc ttc aag ctt acc cgc cat ttc gta ggt ctg           1104
Val Arg Ile Leu Arg Ile Phe Lys Leu Thr Arg His Phe Val Gly Leu
        355                 360                 365 aga gtg ctc gga cac act ctt cgt gcg agc acc aat gaa ttt ttg ttg           1152
Arg Val Leu Gly His Thr Leu Arg Ala Ser Thr Asn Glu Phe Leu Leu
370                 375                 380 ctg atc atc ttt ctg gct ctg gga gtt ttg ata ttc gct acg atg atc           1200
Leu Ile Ile Phe Leu Ala Leu Gly Val Leu Ile Phe Ala Thr Met Ile
385                 390                 395                 400 tac tac gct gag cga gta ggg gct caa cct aat gat ccc tca gcg agt           1248
Tyr Tyr Ala Glu Arg Val Gly Ala Gln Pro Asn Asp Pro Ser Ala Ser
                405                 410                 415 gag cac aca cag ttc aaa aac atc ccc att ggt ttc tgg tgg gct gtg           1296
Glu His Thr Gln Phe Lys Asn Ile Pro Ile Gly Phe Trp Trp Ala Val
            420                 425                 430 gtg acc atg act acc tta ggc tat ggg gat atg tac ccc caa aca tgg           1344
Val Thr Met Thr Thr Leu Gly Tyr Gly Asp Met Tyr Pro Gln Thr Trp
        435                 440                 445 tca ggg atg ttg gtg ggg gcc ttg tgt gct ctg gct gga gtg ctg acc           1392
Ser Gly Met Leu Val Gly Ala Leu Cys Ala Leu Ala Gly Val Leu Thr
450                 455                 460 ata gct atg cct gtg ccc gtc att gtc aac aat ttt ggg atg tac tac           1440
Ile Ala Met Pro Val Pro Val Ile Val Asn Asn Phe Gly Met Tyr Tyr
465                 470                 475                 480 tcc ttg gca atg gcg aag cag aaa ctt cca aga aaa aga aag aag cac           1488
Ser Leu Ala Met Ala Lys Gln Lys Leu Pro Arg Lys Arg Lys Lys His
                485                 490                 495 att cct cct gcc cct ctg gca agc tca cct aca ttt gca aag aca gaa           1536
Ile Pro Pro Ala Pro Leu Ala Ser Ser Pro Thr Phe Cys Lys Thr Glu
            500                 505                 510 tta aac atg gct tgt aac agt acc cag agt gac aca tgt ctg ggc aaa           1584
Leu Asn Met Ala Cys Asn Ser Thr Gln Ser Asp Thr Cys Leu Gly Lys
        515                 520                 525 gaa aac cgg ctt ctg gaa cat aac aga tca gtg tta tca ggt gac gac           1632
Glu Asn Arg Leu Leu Glu His Asn Arg Ser Val Leu Ser Gly Asp Asp
530                 535                 540
```

```
agt aca gga agt gag ccg cca tta tca cct ccg gaa agg ctc ccc atc      1680
Ser Thr Gly Ser Glu Pro Pro Leu Ser Pro Pro Glu Arg Leu Pro Ile
545                 550                 555                 560 aga cgc tct agt acc aga gac aaa aac aga aga ggg gaa aca tgt ttc      1728
Arg Arg Ser Ser Thr Arg Asp Lys Asn Arg Arg Gly Glu Thr Cys Phe
            565                 570                 575 ctg ttg acg aca ggt gat tac acg tgc gct tct gat gga gga atc agg      1776
Leu Leu Thr Thr Gly Asp Tyr Thr Cys Ala Ser Asp Gly Gly Ile Arg
        580                 585                 590 aaa gca agc aca cta gag ccc atg gag agt act tca cag act aaa gga      1824
Lys Ala Ser Thr Leu Glu Pro Met Glu Ser Thr Ser Gln Thr Lys Gly
    595                 600                 605 gac acg aga cca gaa gct cac tgg aat tgt gcg cat tta ctc aat ttt      1872
Asp Thr Arg Pro Glu Ala His Trp Asn Cys Ala His Leu Leu Asn Phe
610                 615                 620 ggc tgt cct acg gga agt tca ttt ccc acc ctc taa                      1908
Gly Cys Pro Thr Gly Ser Ser Phe Pro Thr Leu
625                 630                 635

<210> SEQ ID NO 16
<211> LENGTH: 635
<212> TYPE: PRT
<213> ORGANISM: Rattus norvegicus

<400> SEQUENCE: 16

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
    50                  55                  60

Pro Arg Pro Pro Leu Ser Pro Val Pro Ser Gly Cys Phe Glu Gly
65                  70                  75                  80

Gly Ala Gly Asn Cys Ser Ser His Gly Gly Asn Gly Ser Asp His Pro
            85                  90                  95

Gly Gly Gly Arg Glu Phe Phe Phe Asp Arg His Pro Gly Val Phe Ala
        100                 105                 110

Tyr Val Leu Asn Tyr Tyr Arg Thr Gly Lys Leu His Cys Pro Ala Asp
    115                 120                 125

Val Cys Gly Pro Leu Phe Glu Glu Glu Leu Ala Phe Trp Gly Ile Asp
130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
            165                 170                 175

Gly Asp Pro Gly Asp Asp Glu Asp Leu Gly Gly Lys Arg Leu Gly Ile
        180                 185                 190

Glu Asp Ala Ala Gly Leu Gly Gly Pro Asp Gly Lys Ser Gly Arg Trp
    195                 200                 205

Arg Lys Leu Gln Pro Arg Met Trp Ala Leu Phe Glu Asp Pro Tyr Ser
210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
            245                 250                 255
```

```
Val Lys Asn Lys Thr Glu Pro Val Ile Asn Gly Thr Ser Ala Val Leu
            260                 265                 270

Gln Tyr Glu Ile Glu Thr Asp Pro Ala Leu Thr Tyr Val Glu Gly Val
            275                 280                 285

Cys Val Val Trp Phe Thr Phe Glu Phe Leu Val Arg Ile Val Phe Ser
290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Val Arg Phe
            340                 345                 350

Val Arg Ile Leu Arg Ile Phe Lys Leu Thr Arg His Phe Val Gly Leu
            355                 360                 365

Arg Val Leu Gly His Thr Leu Arg Ala Ser Thr Asn Glu Phe Leu Leu
            370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
            420                 425                 430

Val Thr Met Thr Thr Leu Gly Tyr Gly Asp Met Tyr Pro Gln Thr Trp
            435                 440                 445

Ser Gly Met Leu Val Gly Ala Leu Cys Ala Leu Ala Gly Val Leu Thr
            450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Leu Ala Ser Ser Pro Thr Phe Cys Lys Thr Glu
            500                 505                 510

Leu Asn Met Ala Cys Asn Ser Thr Gln Ser Asp Thr Cys Leu Gly Lys
            515                 520                 525

Glu Asn Arg Leu Leu Glu His Asn Arg Ser Val Leu Ser Gly Asp Asp
            530                 535                 540

Ser Thr Gly Ser Glu Pro Pro Leu Ser Pro Glu Arg Leu Pro Ile
545                 550                 555                 560

Arg Arg Ser Ser Thr Arg Asp Lys Asn Arg Arg Gly Glu Thr Cys Phe
            565                 570                 575

Leu Leu Thr Thr Gly Asp Tyr Thr Cys Ala Ser Asp Gly Gly Ile Arg
            580                 585                 590

Lys Ala Ser Thr Leu Glu Pro Met Glu Ser Thr Ser Gln Thr Lys Gly
            595                 600                 605

Asp Thr Arg Pro Glu Ala His Trp Asn Cys Ala His Leu Leu Asn Phe
            610                 615                 620

Gly Cys Pro Thr Gly Ser Ser Phe Pro Thr Leu
625                 630                 635

<210> SEQ ID NO 17
<211> LENGTH: 1875
<212> TYPE: DNA
<213> ORGANISM: Rattus norvegicus
<220> FEATURE:
```

<220> NAME/KEY: CDS
<222> LOCATION: (1)..(1872)

<400> SEQUENCE: 17

```
atg ggc aag atc gag aac aac gag agg gtg atc ctc aat gtc gga ggc      48
Met Gly Lys Ile Glu Asn Asn Glu Arg Val Ile Leu Asn Val Gly Gly
1               5                   10                  15 acc agg cac gaa acc tac cgc agc act ctc aag acc ctt cct gga act      96
Thr Arg His Glu Thr Tyr Arg Ser Thr Leu Lys Thr Leu Pro Gly Thr
            20                  25                  30 cgc ctg gcc ctt ctc gcc tcc tct gaa cct cag ggc gac tgc ctg act     144
Arg Leu Ala Leu Leu Ala Ser Ser Glu Pro Gln Gly Asp Cys Leu Thr
        35                  40                  45 gct gcg ggt gac aag ctg cag ccg ctg ccc cct ccg ctg tct cca ccg     192
Ala Ala Gly Asp Lys Leu Gln Pro Leu Pro Pro Pro Leu Ser Pro Pro
    50                  55                  60 ccg cga ccg cct ccc ttg tcc cct gtc ccc agc ggc tgc ttc gag ggc     240
Pro Arg Pro Pro Pro Leu Ser Pro Val Pro Ser Gly Cys Phe Glu Gly
65                  70                  75                  80 ggc gca ggc aac tgc agt tcg cac ggt ggc aat ggc agc gac cac cct     288
Gly Ala Gly Asn Cys Ser Ser His Gly Gly Asn Gly Ser Asp His Pro
                85                  90                  95 ggg gga ggc cgc gaa ttc ttc ttc gat cgc cac cca gga gtc ttc gcc     336
Gly Gly Gly Arg Glu Phe Phe Phe Asp Arg His Pro Gly Val Phe Ala
            100                 105                 110 tat gtg ctc aac tac tac cgc acg ggc aag ctg cac tgc ccc gcc gac     384
Tyr Val Leu Asn Tyr Tyr Arg Thr Gly Lys Leu His Cys Pro Ala Asp
        115                 120                 125 gtg tgt gga ccg ctc ttc gag gaa gag ctg gca ttc tgg ggc atc gat     432
Val Cys Gly Pro Leu Phe Glu Glu Glu Leu Ala Phe Trp Gly Ile Asp
    130                 135                 140 gag acc gac gtg gag ccc tgc tgc tgg atg acc tac agg cag cac cgg     480
Glu Thr Asp Val Glu Pro Cys Cys Trp Met Thr Tyr Arg Gln His Arg
145                 150                 155                 160 gac gcg gag gag gcc ctg gat atc ttc gag aca ccc gac ctc atc gga     528
Asp Ala Glu Glu Ala Leu Asp Ile Phe Glu Thr Pro Asp Leu Ile Gly
                165                 170                 175 ggc gac cct ggt gat gat gag gac cta ggg ggc aag aga ctg ggc att     576
Gly Asp Pro Gly Asp Asp Glu Asp Leu Gly Gly Lys Arg Leu Gly Ile
            180                 185                 190 gag gat gct gcg ggg ctg gga gga ccc gat ggc aag tct ggc cgc tgg     624
Glu Asp Ala Ala Gly Leu Gly Gly Pro Asp Gly Lys Ser Gly Arg Trp
        195                 200                 205 agg aag ctg cag cct cgc atg tgg gct ctc ttt gag gac ccc tat tca     672
Arg Lys Leu Gln Pro Arg Met Trp Ala Leu Phe Glu Asp Pro Tyr Ser
    210                 215                 220 tcc aga gcc gct agg ttt att gct ttt gct tct ctg ttc ttc att ttg     720
Ser Arg Ala Ala Arg Phe Ile Ala Phe Ala Ser Leu Phe Phe Ile Leu
225                 230                 235                 240 gtt tcc atc aca acc ttt tgc ctg gag aca cac gaa gct ttc aat att     768
Val Ser Ile Thr Thr Phe Cys Leu Glu Thr His Glu Ala Phe Asn Ile
                245                 250                 255 gtt aaa aac aag aca gag cca gtc atc aac ggc acc agc gct gtt ctc     816
Val Lys Asn Lys Thr Glu Pro Val Ile Asn Gly Thr Ser Ala Val Leu
            260                 265                 270 cag tat gaa atc gaa acg gat cct gcc ttg aca tat gtg gaa gga gtg     864
Gln Tyr Glu Ile Glu Thr Asp Pro Ala Leu Thr Tyr Val Glu Gly Val
        275                 280                 285 tgt gtg gtg tgg ttt act ttt gaa ttt tta gtc cgt att gtt ttc tcg     912
Cys Val Val Trp Phe Thr Phe Glu Phe Leu Val Arg Ile Val Phe Ser
    290                 295                 300
```

-continued

```
                290                 295                 300
ccc aat aaa ctt gag ttc atc aaa aat cta ttg aac atc att gac ttt    960
Pro Asn Lys Leu Glu Phe Ile Lys Asn Leu Leu Asn Ile Ile Asp Phe
305                 310                 315                 320 gtg gcc atc ctc ccc ttc tac tta gag gtg gga ctc agc ggg ctg tct   1008
Val Ala Ile Leu Pro Phe Tyr Leu Glu Val Gly Leu Ser Gly Leu Ser
                325                 330                 335 tcc aaa gcg gct aaa gat gtg ctc ggc ttt ctc agg gtg gtt agg ttt   1056
Ser Lys Ala Ala Lys Asp Val Leu Gly Phe Leu Arg Val Val Arg Phe
            340                 345                 350 gtg agg atc ctg aga atc ttc aag ctt acc cgc cat ttc gta ggt ctg   1104
Val Arg Ile Leu Arg Ile Phe Lys Leu Thr Arg His Phe Val Gly Leu
        355                 360                 365 aga gtc ctc gga cac act ctt cgt gcg agc acc aat gaa ttt ttg ttg   1152
Arg Val Leu Gly His Thr Leu Arg Ala Ser Thr Asn Glu Phe Leu Leu
    370                 375                 380 ctg atc atc ttt ctg gct ctg gga gtt ttg ata ttc gct acg atg atc   1200
Leu Ile Ile Phe Leu Ala Leu Gly Val Leu Ile Phe Ala Thr Met Ile
385                 390                 395                 400 tac tac gct gag cga gta ggg gct caa cct aat gat ccc tca gcg agt   1248
Tyr Tyr Ala Glu Arg Val Gly Ala Gln Pro Asn Asp Pro Ser Ala Ser
                405                 410                 415 gag cac aca cag ttc aaa aac atc ccc att ggt ttc tgg tgg gct gtg   1296
Glu His Thr Gln Phe Lys Asn Ile Pro Ile Gly Phe Trp Trp Ala Val
            420                 425                 430 gtg acc atg act acc tta ggc tat ggg gat atg tac ccc caa aca tgg   1344
Val Thr Met Thr Thr Leu Gly Tyr Gly Asp Met Tyr Pro Gln Thr Trp
        435                 440                 445 tca ggg atg ttg gtg ggg gcc ttg tgt gct ctg gct gga gtg ctg acc   1392
Ser Gly Met Leu Val Gly Ala Leu Cys Ala Leu Ala Gly Val Leu Thr
    450                 455                 460 ata gct atg cct gtg ccc gtc att gtc aac aat ttt ggg atg tac tac   1440
Ile Ala Met Pro Val Pro Val Ile Val Asn Asn Phe Gly Met Tyr Tyr
465                 470                 475                 480 tcc ttg gca atg gcg aag cag aaa ctt cca aga aaa aga aag aag cac   1488
Ser Leu Ala Met Ala Lys Gln Lys Leu Pro Arg Lys Arg Lys Lys His
                485                 490                 495 att cct cct gcc cct ctg gca agc tca cct aca ttt tgc aag aca gaa   1536
Ile Pro Pro Ala Pro Leu Ala Ser Ser Pro Thr Phe Cys Lys Thr Glu
            500                 505                 510 tta aac atg gct tgt aac agt acc cag agt gac aca tgt ctg ggc aaa   1584
Leu Asn Met Ala Cys Asn Ser Thr Gln Ser Asp Thr Cys Leu Gly Lys
        515                 520                 525 gaa aac cgg ctt ctg gaa cat aac aga tca gtg tta tca ggt gac gac   1632
Glu Asn Arg Leu Leu Glu His Asn Arg Ser Val Leu Ser Gly Asp Asp
    530                 535                 540 agt aca gga agt gag ccg cca tta tca cct ccg gaa agg ctc ccc atc   1680
Ser Thr Gly Ser Glu Pro Pro Leu Ser Pro Pro Glu Arg Leu Pro Ile
545                 550                 555                 560 aga cgc tct agt acc aga gac aaa aac aga aga ggg gaa aca tgt ttc   1728
Arg Arg Ser Ser Thr Arg Asp Lys Asn Arg Arg Gly Glu Thr Cys Phe
                565                 570                 575 ctg ttg acg aca ggt gat tac acg tgc gct tct gat gga gga atc agg   1776
Leu Leu Thr Thr Gly Asp Tyr Thr Cys Ala Ser Asp Gly Gly Ile Arg
            580                 585                 590 aaa gtg ttg tac aga att tat cat gga ttt ttg cct gct gaa aat ggg   1824
Lys Val Leu Tyr Arg Ile Tyr His Gly Phe Leu Pro Ala Glu Asn Gly
        595                 600                 605 aca ttg aga ttt agc cat tcc aag gat tgt act gga aac ttc tgc tac   1872
```

-continued

```
Thr Leu Arg Phe Ser His Ser Lys Asp Cys Thr Gly Asn Phe Cys Tyr
    610                 615                 620 tga                                                                    1875

<210> SEQ ID NO 18
<211> LENGTH: 624
<212> TYPE: PRT
<213> ORGANISM: Rattus norvegicus

<400> SEQUENCE: 18

Met Gly Lys Ile Glu Asn Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
    50                  55                  60

Pro Arg Pro Pro Leu Ser Pro Val Pro Ser Gly Cys Phe Glu Gly
65                  70                  75                  80

Gly Ala Gly Asn Cys Ser Ser Gly Gly Asn Gly Ser Asp His Pro
                85                  90                  95

Gly Gly Gly Arg Glu Phe Phe Phe Asp Arg His Pro Gly Val Phe Ala
            100                 105                 110

Tyr Val Leu Asn Tyr Tyr Arg Thr Gly Lys Leu His Cys Pro Ala Asp
            115                 120                 125

Val Cys Gly Pro Leu Phe Glu Glu Glu Leu Ala Phe Trp Gly Ile Asp
    130                 135                 140

Glu Thr Asp Val Glu Pro Cys Cys Trp Met Thr Tyr Arg Gln His Arg
145                 150                 155                 160

Asp Ala Glu Glu Ala Leu Asp Ile Phe Glu Thr Pro Asp Leu Ile Gly
                165                 170                 175

Gly Asp Pro Gly Asp Asp Glu Asp Leu Gly Gly Lys Arg Leu Gly Ile
            180                 185                 190

Glu Asp Ala Ala Gly Leu Gly Gly Pro Asp Gly Lys Ser Gly Arg Trp
        195                 200                 205

Arg Lys Leu Gln Pro Arg Met Trp Ala Leu Phe Glu Asp Pro Tyr Ser
    210                 215                 220

Ser Arg Ala Ala Arg Phe Ile Ala Phe Ala Ser Leu Phe Phe Ile Leu
225                 230                 235                 240

Val Ser Ile Thr Thr Phe Cys Leu Glu Thr His Glu Ala Phe Asn Ile
                245                 250                 255

Val Lys Asn Lys Thr Glu Pro Val Ile Asn Gly Thr Ser Ala Val Leu
            260                 265                 270

Gln Tyr Glu Ile Glu Thr Asp Pro Ala Leu Thr Tyr Val Glu Gly Val
        275                 280                 285

Cys Val Val Trp Phe Thr Phe Glu Phe Leu Val Arg Ile Val Phe Ser
    290                 295                 300

Pro Asn Lys Leu Glu Phe Ile Lys Asn Leu Leu Asn Ile Ile Asp Phe
305                 310                 315                 320

Val Ala Ile Leu Pro Phe Tyr Leu Glu Val Gly Leu Ser Gly Leu Ser
                325                 330                 335

Ser Lys Ala Ala Lys Asp Val Leu Gly Phe Leu Arg Val Arg Phe
            340                 345                 350
```

```
Val Arg Ile Leu Arg Ile Phe Lys Leu Thr Arg His Phe Val Gly Leu
        355                 360                 365

Arg Val Leu Gly His Thr Leu Arg Ala Ser Thr Asn Glu Phe Leu Leu
    370                 375                 380

Leu Ile Ile Phe Leu Ala Leu Gly Val Leu Ile Phe Ala Thr Met Ile
385                 390                 395                 400

Tyr Tyr Ala Glu Arg Val Gly Ala Gln Pro Asn Asp Pro Ser Ala Ser
                405                 410                 415

Glu His Thr Gln Phe Lys Asn Ile Pro Ile Gly Phe Trp Trp Ala Val
                420                 425                 430

Val Thr Met Thr Thr Leu Gly Tyr Gly Asp Met Tyr Pro Gln Thr Trp
            435                 440                 445

Ser Gly Met Leu Val Gly Ala Leu Cys Ala Leu Ala Gly Val Leu Thr
        450                 455                 460

Ile Ala Met Pro Val Pro Val Ile Val Asn Asn Phe Gly Met Tyr Tyr
465                 470                 475                 480

Ser Leu Ala Met Ala Lys Gln Lys Leu Pro Arg Lys Arg Lys Lys His
                485                 490                 495

Ile Pro Pro Ala Pro Leu Ala Ser Ser Pro Thr Phe Cys Lys Thr Glu
            500                 505                 510

Leu Asn Met Ala Cys Asn Ser Thr Gln Ser Asp Thr Cys Leu Gly Lys
        515                 520                 525

Glu Asn Arg Leu Leu Glu His Asn Arg Ser Val Leu Ser Gly Asp Asp
        530                 535                 540

Ser Thr Gly Ser Glu Pro Pro Leu Ser Pro Pro Glu Arg Leu Pro Ile
545                 550                 555                 560

Arg Arg Ser Ser Thr Arg Asp Lys Asn Arg Arg Gly Glu Thr Cys Phe
                565                 570                 575

Leu Leu Thr Thr Gly Asp Tyr Thr Cys Ala Ser Asp Gly Gly Ile Arg
                580                 585                 590

Lys Val Leu Tyr Arg Ile Tyr His Gly Phe Leu Pro Ala Glu Asn Gly
            595                 600                 605

Thr Leu Arg Phe Ser His Ser Lys Asp Cys Thr Gly Asn Phe Cys Tyr
        610                 615                 620

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaggtaccac catgggcaag atcgagaaca acga                             34

<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aactcgagca tgttttgtgc cttccccaag t                                31

<210> SEQ ID NO 21
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gctggcccag gaagaaattt taga                                            24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
agaggaagca gggtccgtat ctct                                            24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gaacatggct tgcaacagta ccc                                             23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
acttcagtca ggaccccatc ctc                                             23

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccattggctc aagaagaggt gatt                                            24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcatagtct gtgacaagga agca                                            24

<210> SEQ ID NO 27
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aagagggtgt ggtcgagagg aaac                                           24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aagagcacag gtgtgagaca ctgg                                           24

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aatctagagc cgccatgggc caagggacg agagcg                               36

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aactcgagac tggatctgga atcatcgcta ca                                  32

<210> SEQ ID NO 31
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aagctagcca ccatgctgag ctcagtctgc gtctcgtcct tc                       42

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aagaattcag ggggatatcc aggccgcggc gttgg                               35

<210> SEQ ID NO 33
<211> LENGTH: 38
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 33
aaagctagcc gccatgatca gctcggtgtg tgtctcct                              38

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aactcgagcc tcaacacttt gccctcataa ag                                   32

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggagacccaa gcagatccac ttta                                            24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ggagagcaag acacgtgaat gaaa                                            24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ctgttcgcga catgtcgcat acag                                            24

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cacatgtatt gtgccttccc aagcc                                           25

<210> SEQ ID NO 39
<211> LENGTH: 1716
<212> TYPE: DNA
<213> ORGANISM: Xenopus laevis
```

```
<220> FEATURE:
<221> NAME/KEY: CDS
<222> LOCATION: (1)..(1713)

<400> SEQUENCE: 39 atg ggt aag atc gac gag aac gag aaa ata atc ctg aac gtc ggg ggt      48
Met Gly Lys Ile Asp Glu Asn Glu Lys Ile Ile Leu Asn Val Gly Gly
1               5                  10                  15 acg aga cac gag act tac cga agc acc tta aag aca gtg ccc ggg act      96
Thr Arg His Glu Thr Tyr Arg Ser Thr Leu Lys Thr Val Pro Gly Thr
            20                  25                  30 cgc ttg gct cta ctt gcc tgt gat gct ccc agt gac cag agg ctg gac     144
Arg Leu Ala Leu Leu Ala Cys Asp Ala Pro Ser Asp Gln Arg Leu Asp
        35                  40                  45 cag cag aca gtg tcg ggc tcc ttc aac atc acc tcc aga ggc aat gaa     192
Gln Gln Thr Val Ser Gly Ser Phe Asn Ile Thr Ser Arg Gly Asn Glu
    50                  55                  60 ttc ttc ttc gac aga cac ccc gga gta ttt gcc tat gta ctc aac tac     240
Phe Phe Phe Asp Arg His Pro Gly Val Phe Ala Tyr Val Leu Asn Tyr
65                  70                  75                  80 tac cgc acc ggc aag ctg cac tgc ccc gct gat gtg tgc ggg ccc ctc     288
Tyr Arg Thr Gly Lys Leu His Cys Pro Ala Asp Val Cys Gly Pro Leu
                85                  90                  95 ttt gaa gag gag ttg gca ttt tgg ggc att gat gag acg gac gtg gag     336
Phe Glu Glu Glu Leu Ala Phe Trp Gly Ile Asp Glu Thr Asp Val Glu
            100                 105                 110 ccc tgt tgc tgg atg acc tat cgc caa cac cgg gat gca gaa gaa gct     384
Pro Cys Cys Trp Met Thr Tyr Arg Gln His Arg Asp Ala Glu Glu Ala
        115                 120                 125 ttg gac agc ttt gaa aat ccc gac ctg atc aca ggg gaa cct cta gat     432
Leu Asp Ser Phe Glu Asn Pro Asp Leu Ile Thr Gly Glu Pro Leu Asp
    130                 135                 140 gaa tat gag gag gag ttg ggg aag aga ctg gca att gag gac gtg gtg     480
Glu Tyr Glu Glu Glu Leu Gly Lys Arg Leu Ala Ile Glu Asp Val Val
145                 150                 155                 160 tgt ccc gat ggc aag gtt ggg cgt tgg aga aga cta agg cct cgc ata     528
Cys Pro Asp Gly Lys Val Gly Arg Trp Arg Arg Leu Arg Pro Arg Ile
                165                 170                 175 tgg gct tta ttt gaa gat ccc tat tct tcc aga gcc gcc cgg ttc atc     576
Trp Ala Leu Phe Glu Asp Pro Tyr Ser Ser Arg Ala Ala Arg Phe Ile
            180                 185                 190 gcc ttt gct tcc ctg ttc ttc att ctg gta tct ata aca acc ttt tgc     624
Ala Phe Ala Ser Leu Phe Phe Ile Leu Val Ser Ile Thr Thr Phe Cys
        195                 200                 205 ttg gag act cat gaa gca ttt aat acc atc att aac aaa acg gaa act     672
Leu Glu Thr His Glu Ala Phe Asn Thr Ile Ile Asn Lys Thr Glu Thr
    210                 215                 220 gta aac aat ggt aca gaa tta atc tca ttg att gaa ata gaa act gat     720
Val Asn Asn Gly Thr Glu Leu Ile Ser Leu Ile Glu Ile Glu Thr Asp
225                 230                 235                 240 cca gcc ttg acg tat gtg gaa gga gta tgc gtg gtt tgg ttc aca ttt     768
Pro Ala Leu Thr Tyr Val Glu Gly Val Cys Val Val Trp Phe Thr Phe
                245                 250                 255 gag ttt tta gta cgt gtc att ttc tgc cct gac aaa ctt gaa ttc atc     816
Glu Phe Leu Val Arg Val Ile Phe Cys Pro Asp Lys Leu Glu Phe Ile
            260                 265                 270 aga aat ctt tta aat ata ata gat ttt gtg gca att ctg ccc ttt tat     864
Arg Asn Leu Leu Asn Ile Ile Asp Phe Val Ala Ile Leu Pro Phe Tyr
        275                 280                 285 ttg gaa gtt gga cta agt ggg ctt tcc tcc aaa gct gct aag gat gtt     912
```

| | | | | | | | | | | | | | | | | |
|---|---|---|---|---|---|---|---|---|---|---|---|---|---|---|---|---|
| | Leu | Glu | Val | Gly | Leu | Ser | Gly | Leu | Ser | Ser | Lys | Ala | Ala | Lys | Asp | Val |
| | | 290 | | | | 295 | | | | 300 | | | | | | |
| ctc | ggg | ttc | ctc | agg | gtt | gta | aga | ttt | gtt | cgc | atc | ctt | cga | att | ttt | 960 |
| Leu | Gly | Phe | Leu | Arg | Val | Val | Arg | Phe | Val | Arg | Ile | Leu | Arg | Ile | Phe | |
| 305 | | | | | 310 | | | | | 315 | | | | | 320 | |
| aaa | ctg | acc | cgc | cat | ttt | gta | gga | ctt | aga | gtg | ctg | ggg | cac | aca | ctt | 1008 |
| Lys | Leu | Thr | Arg | His | Phe | Val | Gly | Leu | Arg | Val | Leu | Gly | His | Thr | Leu | |
| | | | | 325 | | | | | 330 | | | | | 335 | | |
| cgt | gcg | agc | act | aat | gaa | ttt | ttg | ctc | ctt | att | att | ttt | ttg | gct | ctg | 1056 |
| Arg | Ala | Ser | Thr | Asn | Glu | Phe | Leu | Leu | Leu | Ile | Ile | Phe | Leu | Ala | Leu | |
| | | | 340 | | | | | 345 | | | | | 350 | | | |
| gga | gtc | ttg | ata | ttt | gcc | aca | atg | atc | tat | tac | gct | gaa | aga | ata | ggt | 1104 |
| Gly | Val | Leu | Ile | Phe | Ala | Thr | Met | Ile | Tyr | Tyr | Ala | Glu | Arg | Ile | Gly | |
| | | 355 | | | | | 360 | | | | | 365 | | | | |
| gcc | agt | cca | agt | gat | cca | tcg | gca | agt | aaa | cat | aca | caa | ttc | aaa | aac | 1152 |
| Ala | Ser | Pro | Ser | Asp | Pro | Ser | Ala | Ser | Lys | His | Thr | Gln | Phe | Lys | Asn | |
| | 370 | | | | | 375 | | | | | 380 | | | | | |
| att | cca | att | gga | ttc | tgg | tgg | gct | gtg | gta | act | atg | act | acc | ctg | gga | 1200 |
| Ile | Pro | Ile | Gly | Phe | Trp | Trp | Ala | Val | Val | Thr | Met | Thr | Thr | Leu | Gly | |
| 385 | | | | | 390 | | | | | 395 | | | | | 400 | |
| tat | ggg | gat | atg | tac | cct | cag | act | tgg | tca | ggg | atg | ttg | gta | gga | gca | 1248 |
| Tyr | Gly | Asp | Met | Tyr | Pro | Gln | Thr | Trp | Ser | Gly | Met | Leu | Val | Gly | Ala | |
| | | | | 405 | | | | | 410 | | | | | 415 | | |
| tta | tgt | gct | ttg | gct | ggt | gta | ctt | aca | ata | gca | atg | cct | gtc | cca | gtc | 1296 |
| Leu | Cys | Ala | Leu | Ala | Gly | Val | Leu | Thr | Ile | Ala | Met | Pro | Val | Pro | Val | |
| | | | 420 | | | | | 425 | | | | | 430 | | | |
| att | gtt | aac | aac | ttt | gga | atg | tat | tac | tca | ctt | gct | atg | gca | aaa | cag | 1344 |
| Ile | Val | Asn | Asn | Phe | Gly | Met | Tyr | Tyr | Ser | Leu | Ala | Met | Ala | Lys | Gln | |
| | | 435 | | | | | 440 | | | | | 445 | | | | |
| aag | ctt | cca | agg | aaa | aga | aag | aaa | tac | att | cct | cat | gct | cct | cag | gct | 1392 |
| Lys | Leu | Pro | Arg | Lys | Arg | Lys | Lys | Tyr | Ile | Pro | His | Ala | Pro | Gln | Ala | |
| | 450 | | | | | 455 | | | | | 460 | | | | | |
| gga | tcc | cct | act | ttc | tgc | aag | atg | gac | cta | agt | att | gga | tgc | aat | agc | 1440 |
| Gly | Ser | Pro | Thr | Phe | Cys | Lys | Met | Asp | Leu | Ser | Ile | Gly | Cys | Asn | Ser | |
| 465 | | | | | 470 | | | | | 475 | | | | | 480 | |
| aca | cag | gta | gac | aca | tgt | ctt | gga | aaa | gac | aac | aga | ctg | atg | gaa | cac | 1488 |
| Thr | Gln | Val | Asp | Thr | Cys | Leu | Gly | Lys | Asp | Asn | Arg | Leu | Met | Glu | His | |
| | | | | 485 | | | | | 490 | | | | | 495 | | |
| aac | atg | tca | ggt | gaa | gac | agt | tca | gga | agt | gac | cag | cca | ctt | tcc | cct | 1536 |
| Asn | Met | Ser | Gly | Glu | Asp | Ser | Ser | Gly | Ser | Asp | Gln | Pro | Leu | Ser | Pro | |
| | | | 500 | | | | | 505 | | | | | 510 | | | |
| ggt | gaa | aga | tat | cct | ata | aga | cgt | tct | agt | acc | cgc | gat | aaa | aac | aga | 1584 |
| Gly | Glu | Arg | Tyr | Pro | Ile | Arg | Arg | Ser | Ser | Thr | Arg | Asp | Lys | Asn | Arg | |
| | | 515 | | | | | 520 | | | | | 525 | | | | |
| agg | acg | gga | act | tgt | ttc | cta | ctg | acc | aca | ggt | gaa | tac | acg | tgc | aat | 1632 |
| Arg | Thr | Gly | Thr | Cys | Phe | Leu | Leu | Thr | Thr | Gly | Glu | Tyr | Thr | Cys | Asn | |
| | 530 | | | | | 535 | | | | | 540 | | | | | |
| aca | gat | gga | ggt | ata | cgg | aaa | gat | aac | tgc | aaa | gag | gtt | gtc | att | act | 1680 |
| Thr | Asp | Gly | Gly | Ile | Arg | Lys | Asp | Asn | Cys | Lys | Glu | Val | Val | Ile | Thr | |
| 545 | | | | | 550 | | | | | 555 | | | | | 560 | |
| ggt | tac | acg | caa | gca | gag | gcc | aga | tct | ctt | tca | taa | | | | | 1716 |
| Gly | Tyr | Thr | Gln | Ala | Glu | Ala | Arg | Ser | Leu | Ser | | | | | | |
| | | | 565 | | | | | 570 | | | | | | | | |

<210> SEQ ID NO 40
<211> LENGTH: 571
<212> TYPE: PRT
<213> ORGANISM: Xenopus laevis

<400> SEQUENCE: 40

```
Met Gly Lys Ile Asp Glu Asn Glu Lys Ile Ile Leu Asn Val Gly Gly
1               5                   10                  15

Thr Arg His Glu Thr Tyr Arg Ser Thr Leu Lys Thr Val Pro Gly Thr
            20                  25                  30

Arg Leu Ala Leu Leu Ala Cys Asp Ala Pro Ser Asp Gln Arg Leu Asp
        35                  40                  45

Gln Gln Thr Val Ser Gly Ser Phe Asn Ile Thr Ser Arg Gly Asn Glu
50                      55                  60

Phe Phe Phe Asp Arg His Pro Gly Val Phe Ala Tyr Val Leu Asn Tyr
65                      70                  75                  80

Tyr Arg Thr Gly Lys Leu His Cys Pro Ala Asp Val Cys Gly Pro Leu
                85                  90                  95

Phe Glu Glu Glu Leu Ala Phe Trp Gly Ile Asp Glu Thr Asp Val Glu
            100                 105                 110

Pro Cys Cys Trp Met Thr Tyr Arg Gln His Arg Asp Ala Glu Glu Ala
        115                 120                 125

Leu Asp Ser Phe Glu Asn Pro Asp Leu Ile Thr Gly Glu Pro Leu Asp
    130                 135                 140

Glu Tyr Glu Glu Glu Leu Gly Lys Arg Leu Ala Ile Glu Asp Val Val
145                 150                 155                 160

Cys Pro Asp Gly Lys Val Gly Arg Trp Arg Leu Arg Pro Arg Ile
                165                 170                 175

Trp Ala Leu Phe Glu Asp Pro Tyr Ser Ser Arg Ala Ala Arg Phe Ile
                180                 185                 190

Ala Phe Ala Ser Leu Phe Phe Ile Leu Val Ser Ile Thr Thr Phe Cys
            195                 200                 205

Leu Glu Thr His Glu Ala Phe Asn Thr Ile Ile Asn Lys Thr Glu Thr
        210                 215                 220

Val Asn Asn Gly Thr Glu Leu Ile Ser Leu Ile Glu Ile Glu Thr Asp
225                 230                 235                 240

Pro Ala Leu Thr Tyr Val Glu Gly Val Cys Val Val Trp Phe Thr Phe
                245                 250                 255

Glu Phe Leu Val Arg Val Ile Phe Cys Pro Asp Lys Leu Glu Phe Ile
            260                 265                 270

Arg Asn Leu Leu Asn Ile Ile Asp Phe Val Ala Ile Leu Pro Phe Tyr
        275                 280                 285

Leu Glu Val Gly Leu Ser Gly Leu Ser Ser Lys Ala Ala Lys Asp Val
    290                 295                 300

Leu Gly Phe Leu Arg Val Val Arg Phe Val Arg Ile Leu Arg Ile Phe
305                 310                 315                 320

Lys Leu Thr Arg His Phe Val Gly Leu Arg Val Leu Gly His Thr Leu
                325                 330                 335

Arg Ala Ser Thr Asn Glu Phe Leu Leu Leu Ile Ile Phe Leu Ala Leu
            340                 345                 350

Gly Val Leu Ile Phe Ala Thr Met Ile Tyr Tyr Ala Glu Arg Ile Gly
        355                 360                 365

Ala Ser Pro Ser Asp Pro Ser Ala Ser Lys His Thr Gln Phe Lys Asn
    370                 375                 380

Ile Pro Ile Gly Phe Trp Trp Ala Val Val Thr Met Thr Thr Leu Gly
385                 390                 395                 400

Tyr Gly Asp Met Tyr Pro Gln Thr Trp Ser Gly Met Leu Val Gly Ala
                405                 410                 415

Leu Cys Ala Leu Ala Gly Val Leu Thr Ile Ala Met Pro Val Pro Val
```

-continued

```
                        420                 425                 430
Ile Val Asn Asn Phe Gly Met Tyr Tyr Ser Leu Ala Met Ala Lys Gln
                435                 440                 445
Lys Leu Pro Arg Lys Arg Lys Lys Tyr Ile Pro His Ala Pro Gln Ala
            450                 455                 460
Gly Ser Pro Thr Phe Cys Lys Met Asp Leu Ser Ile Gly Cys Asn Ser
465                 470                 475                 480
Thr Gln Val Asp Thr Cys Leu Gly Lys Asp Asn Arg Leu Met Glu His
                485                 490                 495
Asn Met Ser Gly Glu Asp Ser Ser Gly Ser Asp Gln Pro Leu Ser Pro
            500                 505                 510
Gly Glu Arg Tyr Pro Ile Arg Arg Ser Ser Thr Arg Asp Lys Asn Arg
            515                 520                 525
Arg Thr Gly Thr Cys Phe Leu Leu Thr Thr Gly Glu Tyr Thr Cys Asn
        530                 535                 540
Thr Asp Gly Gly Ile Arg Lys Asp Asn Cys Lys Glu Val Val Ile Thr
545                 550                 555                 560
Gly Tyr Thr Gln Ala Glu Ala Arg Ser Leu Ser
                565                 570
```

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
aaagctagcc gccatgggta agatcgacga gaacga                                36

<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
aaactcgagc acatgtattg tgccttccca agccatt                               37

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atgcattagt gcactggcca atatc                                            25

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

<210> SEQ ID NO 45
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
cacagacgct gaccatgaat gtg          23

<210> SEQ ID NO 46
<211> LENGTH: 1929
<212> TYPE: DNA
<213> ORGANISM: Mus musculus
<220> FEATURE:
<221> NAME/KEY: CDS
<222> LOCATION: (1)..(1926)

<400> SEQUENCE: 46

| | | | | | | | | | | | | | | | | |
|---|---|---|---|---|---|---|---|---|---|---|---|---|---|---|---|---|
| atg | ggc | aag | atc | gag | agc | aac | gag | agg | gtg | atc | ctc | aat | gtc | ggg | ggt | 48 |
| Met | Gly | Lys | Ile | Glu | Ser | Asn | Glu | Arg | Val | Ile | Leu | Asn | Val | Gly | Gly | |
| 1 | | | | 5 | | | | | 10 | | | | | 15 | | |
| acc | agg | cac | gaa | acc | tac | cgc | agc | acc | ctc | aag | acc | ctg | cct | gga | act | 96 |
| Thr | Arg | His | Glu | Thr | Tyr | Arg | Ser | Thr | Leu | Lys | Thr | Leu | Pro | Gly | Thr | |
| | | | 20 | | | | | 25 | | | | | 30 | | | |
| cgc | ctg | gcc | ctt | ctt | gcc | tcc | tct | gaa | cct | cag | ggc | gac | tgc | ctg | act | 144 |
| Arg | Leu | Ala | Leu | Leu | Ala | Ser | Ser | Glu | Pro | Gln | Gly | Asp | Cys | Leu | Thr | |
| | 35 | | | | | 40 | | | | | 45 | | | | | |
| gcg | gcc | ggg | gac | aag | ctg | caa | ccg | ctg | ccc | cct | ccg | ctg | tct | ccg | ccg | 192 |
| Ala | Ala | Gly | Asp | Lys | Leu | Gln | Pro | Leu | Pro | Pro | Pro | Leu | Ser | Pro | Pro | |
| 50 | | | | | 55 | | | | | 60 | | | | | | |
| cca | cga | ccg | cct | ccc | ttg | tcc | cct | gtc | ccc | agc | ggc | tgc | ttc | gag | ggc | 240 |
| Pro | Arg | Pro | Pro | Pro | Leu | Ser | Pro | Val | Pro | Ser | Gly | Cys | Phe | Glu | Gly | |
| 65 | | | | | 70 | | | | | 75 | | | | | 80 | |
| ggc | gca | ggc | aac | tgc | agt | tcg | cac | ggt | ggc | aac | ggc | ggc | aac | ggc | ggc | 288 |
| Gly | Ala | Gly | Asn | Cys | Ser | Ser | His | Gly | Gly | Asn | Gly | Gly | Asn | Gly | Gly | |
| | | | | 85 | | | | | 90 | | | | | 95 | | |
| agc | gac | cac | cct | ggg | gga | ggc | cgc | gaa | ttc | ttc | ttc | gat | cgc | cac | cca | 336 |
| Ser | Asp | His | Pro | Gly | Gly | Gly | Arg | Glu | Phe | Phe | Phe | Asp | Arg | His | Pro | |
| | | | 100 | | | | | 105 | | | | | 110 | | | |
| gga | gta | ttc | gcc | tat | gtg | ctc | aat | tac | tac | cgc | acg | ggc | aag | ctg | cac | 384 |
| Gly | Val | Phe | Ala | Tyr | Val | Leu | Asn | Tyr | Tyr | Arg | Thr | Gly | Lys | Leu | His | |
| | 115 | | | | | 120 | | | | | 125 | | | | | |
| tgc | ccc | gcc | gac | gtg | tgc | ggg | ccg | ctc | ttc | gag | gaa | gag | ctg | gct | ttc | 432 |
| Cys | Pro | Ala | Asp | Val | Cys | Gly | Pro | Leu | Phe | Glu | Glu | Glu | Leu | Ala | Phe | |
| 130 | | | | | 135 | | | | | 140 | | | | | | |
| tgg | ggc | atc | gat | gag | acc | gac | gtg | gag | ccc | tgc | tgc | tgg | atg | acc | tac | 480 |
| Trp | Gly | Ile | Asp | Glu | Thr | Asp | Val | Glu | Pro | Cys | Cys | Trp | Met | Thr | Tyr | |
| 145 | | | | | 150 | | | | | 155 | | | | | 160 | |
| agg | cag | cac | cgg | gac | gcg | gag | gag | gcc | ctg | gac | atc | ttt | gag | aca | ccc | 528 |
| Arg | Gln | His | Arg | Asp | Ala | Glu | Glu | Ala | Leu | Asp | Ile | Phe | Glu | Thr | Pro | |
| | | | | 165 | | | | | 170 | | | | | 175 | | |
| gac | ctc | atc | ggg | ggc | gac | cct | ggt | gat | gat | gag | gac | cta | gcg | gcc | aag | 576 |
| Asp | Leu | Ile | Gly | Gly | Asp | Pro | Gly | Asp | Asp | Glu | Asp | Leu | Ala | Ala | Lys | |
| | | | 180 | | | | | 185 | | | | | 190 | | | |
| aga | ttg | ggc | att | gag | gat | gct | gcg | ggg | ctg | gga | gga | ccc | gat | ggc | aag | 624 |
| Arg | Leu | Gly | Ile | Glu | Asp | Ala | Ala | Gly | Leu | Gly | Gly | Pro | Asp | Gly | Lys | |
| | 195 | | | | | 200 | | | | | 205 | | | | | |
| tca | ggc | cgc | tgg | agg | aag | ctg | cag | cct | cgc | atg | tgg | gct | ctt | ttt | gag | 672 |

```
                                                     -continued

Ser Gly Arg Trp Arg Lys Leu Gln Pro Arg Met Trp Ala Leu Phe Glu
    210             215                 220 gac ccc tac tca tct aga gcc gct agg ttt att gct ttt gct tct ttg    720
Asp Pro Tyr Ser Ser Arg Ala Ala Arg Phe Ile Ala Phe Ala Ser Leu
225                 230                 235                 240 ttc ttc att ttg gtt tcc atc aca acc ttt tgc ctg gag aca cat gaa    768
Phe Phe Ile Leu Val Ser Ile Thr Thr Phe Cys Leu Glu Thr His Glu
                    245                 250                 255 gct ttc aat att gtt aaa aac aag acg gag ccc gtc atc aat ggc acc    816
Ala Phe Asn Ile Val Lys Asn Lys Thr Glu Pro Val Ile Asn Gly Thr
            260                 265                 270 agc ccg gtc ctc cag tac gaa atc gaa acg gat ccc gcc ctg acg tac    864
Ser Pro Val Leu Gln Tyr Glu Ile Glu Thr Asp Pro Ala Leu Thr Tyr
        275                 280                 285 gtg gaa gga gta tgt gtg gtg tgg ttt acg ttt gaa ttt tta gtc cga    912
Val Glu Gly Val Cys Val Val Trp Phe Thr Phe Glu Phe Leu Val Arg
290                 295                 300 att gtt ttc tca ccc aat aaa ctt gaa ttc atc aaa aat ctc ttg aac    960
Ile Val Phe Ser Pro Asn Lys Leu Glu Phe Ile Lys Asn Leu Leu Asn
305                 310                 315                 320 atc att gac ttt gtg gcc atc ctc ccc ttc tac cta gag gtg gga ctc   1008
Ile Ile Asp Phe Val Ala Ile Leu Pro Phe Tyr Leu Glu Val Gly Leu
                    325                 330                 335 agc ggg ctg tcc tcc aaa gcg gcc aaa gat gtg ctc ggc ttt ctc agg   1056
Ser Gly Leu Ser Ser Lys Ala Ala Lys Asp Val Leu Gly Phe Leu Arg
            340                 345                 350 gtg gtt agg ttt gtg agg atc ctg aga atc ttc aag ctc acc cgc cat   1104
Val Val Arg Phe Val Arg Ile Leu Arg Ile Phe Lys Leu Thr Arg His
        355                 360                 365 ttc gta ggt ctg agg gtg ctc gga cat act ctt cgg gcg agc acc aac   1152
Phe Val Gly Leu Arg Val Leu Gly His Thr Leu Arg Ala Ser Thr Asn
370                 375                 380 gaa ttt ttg ttg ctg atc atc ttc ctg gcg ctg gga gtt ttg ata ttc   1200
Glu Phe Leu Leu Leu Ile Ile Phe Leu Ala Leu Gly Val Leu Ile Phe
385                 390                 395                 400 gct acg atg atc tac tac gct gag aga gta ggg gct cag ccc aat gac   1248
Ala Thr Met Ile Tyr Tyr Ala Glu Arg Val Gly Ala Gln Pro Asn Asp
                    405                 410                 415 cct tca gct agt gag cac acg cag ttc aaa aac atc ccc att ggt ttc   1296
Pro Ser Ala Ser Glu His Thr Gln Phe Lys Asn Ile Pro Ile Gly Phe
            420                 425                 430 tgg tgg gcc gta gtg acc atg act acc tta ggt tac ggg gat atg tac   1344
Trp Trp Ala Val Val Thr Met Thr Thr Leu Gly Tyr Gly Asp Met Tyr
        435                 440                 445 ccc caa aca tgg tca ggg atg ttg gtg ggg gcc ttg tgt gcc ctg gcc   1392
Pro Gln Thr Trp Ser Gly Met Leu Val Gly Ala Leu Cys Ala Leu Ala
450                 455                 460 gga gtg ctg aca ata gcc atg cct gtg cct gtc att gtc aac aat ttt   1440
Gly Val Leu Thr Ile Ala Met Pro Val Pro Val Ile Val Asn Asn Phe
465                 470                 475                 480 gga atg tac tac tcc ttg gca atg gcg aag cag aaa ctt cca aga aag   1488
Gly Met Tyr Tyr Ser Leu Ala Met Ala Lys Gln Lys Leu Pro Arg Lys
                    485                 490                 495 aga aag aag cat att cct cct gcc cct ctg gca agc tcg cct aca ttt   1536
Arg Lys Lys His Ile Pro Pro Ala Pro Leu Ala Ser Ser Pro Thr Phe
            500                 505                 510 tgc aag aca gaa ttg aac atg gct tgc aac agt acc cag agt gac aca   1584
Cys Lys Thr Glu Leu Asn Met Ala Cys Asn Ser Thr Gln Ser Asp Thr
        515                 520                 525
```

```
tgt ctg ggc aaa gaa aac cgg ctt ctg gaa cat aac aga tca gtg tta    1632
Cys Leu Gly Lys Glu Asn Arg Leu Leu Glu His Asn Arg Ser Val Leu
530                 535                 540 tca ggt gac gac agt aca gga agt gag ccg cca tta tca cct cca gaa    1680
Ser Gly Asp Asp Ser Thr Gly Ser Glu Pro Pro Leu Ser Pro Pro Glu
545                 550                 555                 560 agg ctc cct atc aga cgc tct agt acc aga gac aaa aac aga aga ggg    1728
Arg Leu Pro Ile Arg Arg Ser Ser Thr Arg Asp Lys Asn Arg Arg Gly
                565                 570                 575 gaa acg tgt ttc ctg ttg acg aca ggt gat tac acg tgc gct tct gat    1776
Glu Thr Cys Phe Leu Leu Thr Thr Gly Asp Tyr Thr Cys Ala Ser Asp
                580                 585                 590 gga gga atc agg aaa gga tat gaa aaa tcc cga agc tta aac aac ata    1824
Gly Gly Ile Arg Lys Gly Tyr Glu Lys Ser Arg Ser Leu Asn Asn Ile
                595                 600                 605 gcg ggc ttg gca ggc aat gct ctg aga ctc tct cca gta acg tcc ccc    1872
Ala Gly Leu Ala Gly Asn Ala Leu Arg Leu Ser Pro Val Thr Ser Pro
610                 615                 620 tac aac tct ccg tgt cct ctg agg cgc tct cgg tct ccc atc cca tct    1920
Tyr Asn Ser Pro Cys Pro Leu Arg Arg Ser Arg Ser Pro Ile Pro Ser
625                 630                 635                 640 atc ttg taa                                                         1929
Ile Leu <210> SEQ ID NO 47
<211> LENGTH: 642
<212> TYPE: PRT
<213> ORGANISM: Mus musculus

<400> SEQUENCE: 47

Met Gly Lys Ile Glu Ser Asn Glu Arg Val Ile Leu Asn Val Gly Gly
1               5                   10                  15

Thr Arg His Glu Thr Tyr Arg Ser Thr Leu Lys Thr Leu Pro Gly Thr
                20                  25                  30

Arg Leu Ala Leu Leu Ala Ser Ser Glu Pro Gln Gly Asp Cys Leu Thr
            35                  40                  45

Ala Ala Gly Asp Lys Leu Gln Pro Leu Pro Pro Leu Ser Pro Pro
50                  55                  60

Pro Arg Pro Pro Leu Ser Pro Val Pro Ser Gly Cys Phe Glu Gly
65                  70                  75                  80

Gly Ala Gly Asn Cys Ser Ser His Gly Gly Asn Gly Gly Asn Gly Gly
                85                  90                  95

Ser Asp His Pro Gly Gly Gly Arg Glu Phe Phe Phe Arg His Pro
                100                 105                 110

Gly Val Phe Ala Tyr Val Leu Asn Tyr Tyr Arg Thr Gly Lys Leu His
            115                 120                 125

Cys Pro Ala Asp Val Cys Gly Pro Leu Phe Glu Glu Glu Leu Ala Phe
130                 135                 140

Trp Gly Ile Asp Glu Thr Asp Val Glu Pro Cys Cys Trp Met Thr Tyr
145                 150                 155                 160

Arg Gln His Arg Asp Ala Glu Glu Ala Leu Asp Ile Phe Glu Thr Pro
                165                 170                 175

Asp Leu Ile Gly Gly Asp Pro Gly Asp Asp Glu Asp Leu Ala Ala Lys
            180                 185                 190

Arg Leu Gly Ile Glu Asp Ala Ala Gly Leu Gly Gly Pro Asp Gly Lys
            195                 200                 205

Ser Gly Arg Trp Arg Lys Leu Gln Pro Arg Met Trp Ala Leu Phe Glu
```

```
              210                 215                 220

Asp Pro Tyr Ser Ser Arg Ala Arg Phe Ile Ala Phe Ala Ser Leu
225                 230                 235                 240

Phe Phe Ile Leu Val Ser Ile Thr Thr Phe Cys Leu Glu Thr His Glu
                245                 250                 255

Ala Phe Asn Ile Val Lys Asn Lys Thr Glu Pro Val Ile Asn Gly Thr
                260                 265                 270

Ser Pro Val Leu Gln Tyr Glu Ile Glu Thr Asp Pro Ala Leu Thr Tyr
                275                 280                 285

Val Glu Gly Val Cys Val Val Trp Phe Thr Phe Glu Phe Leu Val Arg
                290                 295                 300

Ile Val Phe Ser Pro Asn Lys Leu Glu Phe Ile Lys Asn Leu Leu Asn
305                 310                 315                 320

Ile Ile Asp Phe Val Ala Ile Leu Pro Phe Tyr Leu Glu Val Gly Leu
                325                 330                 335

Ser Gly Leu Ser Ser Lys Ala Ala Lys Asp Val Leu Gly Phe Leu Arg
                340                 345                 350

Val Val Arg Phe Val Arg Ile Leu Arg Ile Phe Lys Leu Thr Arg His
                355                 360                 365

Phe Val Gly Leu Arg Val Leu Gly His Thr Leu Arg Ala Ser Thr Asn
                370                 375                 380

Glu Phe Leu Leu Leu Ile Ile Phe Leu Ala Leu Gly Val Leu Ile Phe
385                 390                 395                 400

Ala Thr Met Ile Tyr Tyr Ala Glu Arg Val Gly Ala Gln Pro Asn Asp
                405                 410                 415

Pro Ser Ala Ser Glu His Thr Gln Phe Lys Asn Ile Pro Ile Gly Phe
                420                 425                 430

Trp Trp Ala Val Val Thr Met Thr Thr Leu Gly Tyr Gly Asp Met Tyr
                435                 440                 445

Pro Gln Thr Trp Ser Gly Met Leu Val Gly Ala Leu Cys Ala Leu Ala
                450                 455                 460

Gly Val Leu Thr Ile Ala Met Pro Val Pro Val Ile Val Asn Asn Phe
465                 470                 475                 480

Gly Met Tyr Tyr Ser Leu Ala Met Ala Lys Gln Lys Leu Pro Arg Lys
                485                 490                 495

Arg Lys Lys His Ile Pro Pro Ala Pro Leu Ala Ser Ser Pro Thr Phe
                500                 505                 510

Cys Lys Thr Glu Leu Asn Met Ala Cys Asn Ser Thr Gln Ser Asp Thr
                515                 520                 525

Cys Leu Gly Lys Glu Asn Arg Leu Leu Glu His Asn Arg Ser Val Leu
                530                 535                 540

Ser Gly Asp Asp Ser Thr Gly Ser Glu Pro Pro Leu Ser Pro Pro Glu
545                 550                 555                 560

Arg Leu Pro Ile Arg Arg Ser Ser Thr Arg Asp Lys Asn Arg Arg Gly
                565                 570                 575

Glu Thr Cys Phe Leu Leu Thr Thr Gly Asp Tyr Thr Cys Ala Ser Asp
                580                 585                 590

Gly Gly Ile Arg Lys Gly Tyr Glu Lys Ser Arg Ser Leu Asn Asn Ile
                595                 600                 605

Ala Gly Leu Ala Gly Asn Ala Leu Arg Leu Ser Pro Val Thr Ser Pro
                610                 615                 620

Tyr Asn Ser Pro Cys Pro Leu Arg Arg Ser Arg Ser Pro Ile Pro Ser
625                 630                 635                 640
```

Ile Leu

<210> SEQ ID NO 48
<211> LENGTH: 1854
<212> TYPE: DNA
<213> ORGANISM: Mus musculus
<220> FEATURE:
<221> NAME/KEY: CDS
<222> LOCATION: (1)..(1851)

<400> SEQUENCE: 48

| | | | | | | | | | | | | | | | | |
|---|---|---|---|---|---|---|---|---|---|---|---|---|---|---|---|---|
| atg | ggc | aag | atc | gag | agc | aac | gag | agg | gtg | atc | ctc | aat | gtc | ggg | ggt | 48 |
| Met | Gly | Lys | Ile | Glu | Ser | Asn | Glu | Arg | Val | Ile | Leu | Asn | Val | Gly | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| acc | agg | cac | gaa | acc | tac | cgc | agc | acc | ctc | aag | acc | ctg | cct | gga | act | 96 |
| Thr | Arg | His | Glu | Thr | Tyr | Arg | Ser | Thr | Leu | Lys | Thr | Leu | Pro | Gly | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| cgc | ctg | gcc | ctt | ctt | gcc | tcc | tct | gaa | cct | cag | ggc | gac | tgc | ctg | act | 144 |
| Arg | Leu | Ala | Leu | Leu | Ala | Ser | Ser | Glu | Pro | Gln | Gly | Asp | Cys | Leu | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| gcg | gcc | ggg | gac | aag | ctg | caa | ccg | ctg | ccc | cct | ccg | ctg | tct | ccg | ccg | 192 |
| Ala | Ala | Gly | Asp | Lys | Leu | Gln | Pro | Leu | Pro | Pro | Pro | Leu | Ser | Pro | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| cca | cga | ccg | cct | ccc | ttg | tcc | cct | gtc | ccc | agc | ggc | tgc | ttc | gag | ggc | 240 |
| Pro | Arg | Pro | Pro | Pro | Leu | Ser | Pro | Val | Pro | Ser | Gly | Cys | Phe | Glu | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ggc | gca | ggc | aac | tgc | agt | tcg | cac | ggt | ggc | aac | ggc | ggc | aac | ggc | ggc | 288 |
| Gly | Ala | Gly | Asn | Cys | Ser | Ser | His | Gly | Gly | Asn | Gly | Gly | Asn | Gly | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| agc | gac | cac | cct | ggg | gga | ggc | cgc | gaa | ttc | ttc | ttc | gat | cgc | cac | cca | 336 |
| Ser | Asp | His | Pro | Gly | Gly | Gly | Arg | Glu | Phe | Phe | Phe | Asp | Arg | His | Pro | |
| | | 100 | | | | | 105 | | | | | 110 | | | | |

| | | | | | | | | | | | | | | | | |
|---|---|---|---|---|---|---|---|---|---|---|---|---|---|---|---|---|
| gga | gta | ttc | gcc | tat | gtg | ctc | aat | tac | tac | cgc | acg | ggc | aag | ctg | cac | 384 |
| Gly | Val | Phe | Ala | Tyr | Val | Leu | Asn | Tyr | Tyr | Arg | Thr | Gly | Lys | Leu | His | |
| | 115 | | | | | 120 | | | | | 125 | | | | | |

| | | | | | | | | | | | | | | | | |
|---|---|---|---|---|---|---|---|---|---|---|---|---|---|---|---|---|
| tgc | ccc | gcc | gac | gtg | tgc | ggg | ccg | ctc | ttc | gag | gaa | gag | ctg | gct | ttc | 432 |
| Cys | Pro | Ala | Asp | Val | Cys | Gly | Pro | Leu | Phe | Glu | Glu | Glu | Leu | Ala | Phe | |
| 130 | | | | | 135 | | | | | 140 | | | | | | |

| | | | | | | | | | | | | | | | | |
|---|---|---|---|---|---|---|---|---|---|---|---|---|---|---|---|---|
| tgg | ggc | atc | gat | gag | acc | gac | gtg | gag | ccc | tgc | tgc | tgg | atg | acc | tac | 480 |
| Trp | Gly | Ile | Asp | Glu | Thr | Asp | Val | Glu | Pro | Cys | Cys | Trp | Met | Thr | Tyr | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agg | cag | cac | cgg | gac | gcg | gag | gag | gcc | ctg | gac | atc | ttt | gag | aca | ccc | 528 |
| Arg | Gln | His | Arg | Asp | Ala | Glu | Glu | Ala | Leu | Asp | Ile | Phe | Glu | Thr | Pro | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | ctc | atc | ggg | ggc | gac | cct | ggt | gat | gat | gag | gac | cta | gcg | gcc | aag | 576 |
| Asp | Leu | Ile | Gly | Gly | Asp | Pro | Gly | Asp | Asp | Glu | Asp | Leu | Ala | Ala | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| aga | ttg | ggc | att | gag | gat | gct | gcg | ggg | ctg | gga | gga | ccc | gat | ggc | aag | 624 |
| Arg | Leu | Gly | Ile | Glu | Asp | Ala | Ala | Gly | Leu | Gly | Gly | Pro | Asp | Gly | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| tca | ggc | cgc | tgg | agg | aag | ctg | cag | cct | cgc | atg | tgg | gct | ctt | ttt | gag | 672 |
| Ser | Gly | Arg | Trp | Arg | Lys | Leu | Gln | Pro | Arg | Met | Trp | Ala | Leu | Phe | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| gac | ccc | tac | tca | tct | aga | gcc | gct | agg | ttt | att | gct | ttt | gct | tct | ttg | 720 |
| Asp | Pro | Tyr | Ser | Ser | Arg | Ala | Ala | Arg | Phe | Ile | Ala | Phe | Ala | Ser | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ttc | ttc | att | ttg | gtt | tcc | atc | aca | acc | ttt | tgc | ctg | gag | aca | cat | gaa | 768 |
| Phe | Phe | Ile | Leu | Val | Ser | Ile | Thr | Thr | Phe | Cys | Leu | Glu | Thr | His | Glu | |
| | | | | 245 | | | | | 250 | | | | | 255 | | |

| | | | | | | | | | | | | | | | | |
|---|---|---|---|---|---|---|---|---|---|---|---|---|---|---|---|---|
| gct | ttc | aat | att | gtt | aaa | aac | aag | acg | gag | ccc | gtc | atc | aat | ggc | acc | 816 |

```
                Ala Phe Asn Ile Val Lys Asn Lys Thr Glu Pro Val Ile Asn Gly Thr
                                260                 265                 270 agc ccg gtc ctc cag tac gaa atc gaa acg gat ccc gcc ctg acg tac              864
Ser Pro Val Leu Gln Tyr Glu Ile Glu Thr Asp Pro Ala Leu Thr Tyr
            275                 280                 285 gtg gaa gga gta tgt gtg gtg tgg ttt acg ttt gaa ttt tta gtc cga              912
Val Glu Gly Val Cys Val Val Trp Phe Thr Phe Glu Phe Leu Val Arg
        290                 295                 300 att gtt ttc tca ccc aat aaa ctt gaa ttc atc aaa aat ctc ttg aac              960
Ile Val Phe Ser Pro Asn Lys Leu Glu Phe Ile Lys Asn Leu Leu Asn
305                 310                 315                 320 atc att gac ttt gtg gcc atc ctc ccc ttc tac cta gag gtg gga ctc             1008
Ile Ile Asp Phe Val Ala Ile Leu Pro Phe Tyr Leu Glu Val Gly Leu
                325                 330                 335 agc ggg ctg tcc tcc aaa gcg gcc aaa gat gtg ctc ggc ttt ctc agg             1056
Ser Gly Leu Ser Ser Lys Ala Ala Lys Asp Val Leu Gly Phe Leu Arg
            340                 345                 350 gtg gtt agg ttt gtg agg atc ctg aga atc ttc aag ctc acc cgc cat             1104
Val Val Arg Phe Val Arg Ile Leu Arg Ile Phe Lys Leu Thr Arg His
        355                 360                 365 ttc gta ggt ctg agg gtg ctc gga cat act ctt cgg gcg agc acc aac             1152
Phe Val Gly Leu Arg Val Leu Gly His Thr Leu Arg Ala Ser Thr Asn
370                 375                 380 gaa ttt ttg ttg ctg atc atc ttc ctg gcg ctg gga gtt ttg ata ttc             1200
Glu Phe Leu Leu Leu Ile Ile Phe Leu Ala Leu Gly Val Leu Ile Phe
385                 390                 395                 400 gct acg atg atc tac tac gct gag aga gta ggg gct cag ccc aat gac             1248
Ala Thr Met Ile Tyr Tyr Ala Glu Arg Val Gly Ala Gln Pro Asn Asp
                405                 410                 415 cct tca gct agt gag cac acg cag ttc aaa aac atc ccc att ggt ttc             1296
Pro Ser Ala Ser Glu His Thr Gln Phe Lys Asn Ile Pro Ile Gly Phe
            420                 425                 430 tgg tgg gcc gta gtg acc atg act acc tta ggt tac ggg gat atg tac             1344
Trp Trp Ala Val Val Thr Met Thr Thr Leu Gly Tyr Gly Asp Met Tyr
        435                 440                 445 ccc caa aca tgg tca ggg atg ttg gtg ggg gcc ttg tgt gcc ctg gcc             1392
Pro Gln Thr Trp Ser Gly Met Leu Val Gly Ala Leu Cys Ala Leu Ala
450                 455                 460 gga gtg ctg aca ata gcc atg cct gtg cct gtc att gtc aac aat ttt             1440
Gly Val Leu Thr Ile Ala Met Pro Val Pro Val Ile Val Asn Asn Phe
465                 470                 475                 480 gga atg tac tac tcc ttg gca atg gcg aag cag aaa ctt cca aga aag             1488
Gly Met Tyr Tyr Ser Leu Ala Met Ala Lys Gln Lys Leu Pro Arg Lys
                485                 490                 495 aga aag aag cat att cct cct gcc cct ctg gca agc tcg cct aca ttt             1536
Arg Lys Lys His Ile Pro Pro Ala Pro Leu Ala Ser Ser Pro Thr Phe
            500                 505                 510 tgc aag aca gaa ttg aac atg gct tgc aac agt acc cag agt gac aca             1584
Cys Lys Thr Glu Leu Asn Met Ala Cys Asn Ser Thr Gln Ser Asp Thr
        515                 520                 525 tgt ctg ggc aaa gaa aac cgg ctt ctg gaa cat aac aga tca gtg tta             1632
Cys Leu Gly Lys Glu Asn Arg Leu Leu Glu His Asn Arg Ser Val Leu
530                 535                 540 tca ggt gac gac agt aca gga agt gag ccg cca tta tca cct cca gaa             1680
Ser Gly Asp Asp Ser Thr Gly Ser Glu Pro Pro Leu Ser Pro Pro Glu
545                 550                 555                 560 agg ctc cct atc aga cgc tct agt acc aga gac aaa aac aga aga ggg             1728
Arg Leu Pro Ile Arg Arg Ser Ser Thr Arg Asp Lys Asn Arg Arg Gly
                565                 570                 575
```

| | | | | | | | | | | | | | | | |
|---|---|---|---|---|---|---|---|---|---|---|---|---|---|---|---|
| gaa | acg | tgt | ttc | ctg | ttg | acg | aca | ggt | gat | tac | acg | tgc | gct | tct | gat | 1776 |
| Glu | Thr | Cys | Phe | Leu | Leu | Thr | Thr | Gly | Asp | Tyr | Thr | Cys | Ala | Ser | Asp | |
| | | | 580 | | | | | 585 | | | | | 590 | | | |

| | | | | | | | | | | | | | | | |
|---|---|---|---|---|---|---|---|---|---|---|---|---|---|---|---|
| gga | gga | atc | agg | aaa | gat | aac | tgc | aaa | gag | gtt | gtc | att | act | ggt | tac | 1824 |
| Gly | Gly | Ile | Arg | Lys | Asp | Asn | Cys | Lys | Glu | Val | Val | Ile | Thr | Gly | Tyr | |
| 595 | | | | | 600 | | | | | 605 | | | | | | |

| | | | | | | | | |
|---|---|---|---|---|---|---|---|---|
| acg | caa | gcc | gag | gcc | aga | tct | ctt | act | taa | 1854 |
| Thr | Gln | Ala | Glu | Ala | Arg | Ser | Leu | Thr | | |
| 610 | | | | | 615 | | | | | |

<210> SEQ ID NO 49
<211> LENGTH: 617
<212> TYPE: PRT
<213> ORGANISM: Mus musculus

<400> SEQUENCE: 49

Met Gly Lys Ile Glu Ser Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
    50                  55                  60

Pro Arg Pro Pro Leu Ser Pro Val Pro Ser Gly Cys Phe Glu Gly
65                  70                  75                  80

Gly Ala Gly Asn Cys Ser Ser His Gly Gly Asn Gly Asn Gly Gly
                85                  90                  95

Ser Asp His Pro Gly Gly Arg Glu Phe Phe Asp Arg His Pro
            100                 105                 110

Gly Val Phe Ala Tyr Val Leu Asn Tyr Tyr Arg Thr Gly Lys Leu His
        115                 120                 125

Cys Pro Ala Asp Val Cys Gly Pro Leu Phe Glu Glu Leu Ala Phe
    130                 135                 140

Trp Gly Ile Asp Glu Thr Asp Val Glu Pro Cys Cys Trp Met Thr Tyr
145                 150                 155                 160

Arg Gln His Arg Asp Ala Glu Glu Ala Leu Asp Ile Phe Glu Thr Pro
                165                 170                 175

Asp Leu Ile Gly Gly Asp Pro Gly Asp Asp Glu Asp Leu Ala Ala Lys
            180                 185                 190

Arg Leu Gly Ile Glu Asp Ala Ala Gly Leu Gly Gly Pro Asp Gly Lys
        195                 200                 205

Ser Gly Arg Trp Arg Lys Leu Gln Pro Arg Met Trp Ala Leu Phe Glu
    210                 215                 220

Asp Pro Tyr Ser Ser Arg Ala Ala Arg Phe Ile Ala Phe Ala Ser Leu
225                 230                 235                 240

Phe Phe Ile Leu Val Ser Ile Thr Thr Phe Cys Leu Glu Thr His Glu
                245                 250                 255

Ala Phe Asn Ile Val Lys Asn Lys Thr Glu Pro Val Ile Asn Gly Thr
            260                 265                 270

Ser Pro Val Leu Gln Tyr Glu Ile Glu Thr Asp Pro Ala Leu Thr Tyr
        275                 280                 285

Val Glu Gly Val Cys Val Val Trp Phe Thr Phe Glu Phe Leu Val Arg
    290                 295                 300

Ile Val Phe Ser Pro Asn Lys Leu Glu Phe Ile Lys Asn Leu Leu Asn
305                 310                 315                 320

| | | | | | | | | | | | |
|---|---|---|---|---|---|---|---|---|---|---|---|
|Ile|Ile|Asp|Phe|Val|Ala|Ile|Leu|Pro|Phe|Tyr|Leu|Glu|Val|Gly|Leu|
| | | |325| | | |330| | | |335|

Ser Gly Leu Ser Ser Lys Ala Ala Lys Asp Val Leu Gly Phe Leu Arg
              340                 345                 350

Val Val Arg Phe Val Arg Ile Leu Arg Ile Phe Lys Leu Thr Arg His
              355                 360                 365

Phe Val Gly Leu Arg Val Leu Gly His Thr Leu Arg Ala Ser Thr Asn
          370                 375                 380

Glu Phe Leu Leu Leu Ile Ile Phe Leu Ala Leu Gly Val Leu Ile Phe
385                 390                 395                 400

Ala Thr Met Ile Tyr Tyr Ala Glu Arg Val Gly Ala Gln Pro Asn Asp
                  405                 410                 415

Pro Ser Ala Ser Glu His Thr Gln Phe Lys Asn Ile Pro Ile Gly Phe
              420                 425                 430

Trp Trp Ala Val Val Thr Met Thr Thr Leu Gly Tyr Gly Asp Met Tyr
              435                 440                 445

Pro Gln Thr Trp Ser Gly Met Leu Val Gly Ala Leu Cys Ala Leu Ala
          450                 455                 460

Gly Val Leu Thr Ile Ala Met Pro Val Pro Val Ile Val Asn Asn Phe
465                 470                 475                 480

Gly Met Tyr Tyr Ser Leu Ala Met Ala Lys Gln Lys Leu Pro Arg Lys
                  485                 490                 495

Arg Lys Lys His Ile Pro Pro Ala Pro Leu Ala Ser Ser Pro Thr Phe
              500                 505                 510

Cys Lys Thr Glu Leu Asn Met Ala Cys Asn Ser Thr Gln Ser Asp Thr
              515                 520                 525

Cys Leu Gly Lys Glu Asn Arg Leu Leu Glu His Asn Arg Ser Val Leu
530                 535                 540

Ser Gly Asp Asp Ser Thr Gly Ser Glu Pro Pro Leu Ser Pro Pro Glu
545                 550                 555                 560

Arg Leu Pro Ile Arg Arg Ser Ser Thr Arg Asp Lys Asn Arg Arg Gly
              565                 570                 575

Glu Thr Cys Phe Leu Leu Thr Thr Gly Asp Tyr Thr Cys Ala Ser Asp
              580                 585                 590

Gly Gly Ile Arg Lys Asp Asn Cys Lys Glu Val Val Ile Thr Gly Tyr
              595                 600                 605

Thr Gln Ala Glu Ala Arg Ser Leu Thr
              610                 615

<210> SEQ ID NO 50
<211> LENGTH: 1845
<212> TYPE: DNA
<213> ORGANISM: Mus musculus
<220> FEATURE:
<221> NAME/KEY: CDS
<222> LOCATION: (1)..(1842)

<400> SEQUENCE: 50

```
atg ggc aag atc gag agc aac gag agg gtg atc ctc aat gtc ggg ggt      48
Met Gly Lys Ile Glu Ser Asn Glu Arg Val Ile Leu Asn Val Gly Gly
1               5                  10                  15 acc agg cac gaa acc tac cgc agc acc ctc aag acc ctg cct gga act      96
Thr Arg His Glu Thr Tyr Arg Ser Thr Leu Lys Thr Leu Pro Gly Thr
            20                  25                  30 cgc ctg gcc ctt ctt gcc tcc tct gaa cct cag ggc gac tgc ctg act     144
Arg Leu Ala Leu Leu Ala Ser Ser Glu Pro Gln Gly Asp Cys Leu Thr
```

-continued

|  |  |  |  | 35 |  |  |  | 40 |  |  |  | 45 |  |  |  |  |
|---|---|---|---|---|---|---|---|---|---|---|---|---|---|---|---|---|
| gcg | gcc | ggg | gac | aag | ctg | caa | ccg | ctg | ccc | cct | ccg | ctg | tct | ccg | ccg | 192 |
| Ala | Ala | Gly | Asp | Lys | Leu | Gln | Pro | Leu | Pro | Pro | Pro | Leu | Ser | Pro | Pro |  |
|  |  | 50 |  |  |  | 55 |  |  |  | 60 |  |  |  |  |  |  |

| cca | cga | ccg | cct | ccc | ttg | tcc | cct | gtc | ccc | agc | ggc | tgc | ttc | gag | ggc | 240 |
|---|---|---|---|---|---|---|---|---|---|---|---|---|---|---|---|---|
| Pro | Arg | Pro | Pro | Leu | Ser | Pro | Val | Pro | Ser | Gly | Cys | Phe | Glu | Gly |  |  |
| 65 |  |  |  | 70 |  |  |  | 75 |  |  |  |  | 80 |  |  |  |

| ggc | gca | ggc | aac | tgc | agt | tcg | cac | ggt | ggc | aac | ggc | ggc | aac | ggc | ggc | 288 |
|---|---|---|---|---|---|---|---|---|---|---|---|---|---|---|---|---|
| Gly | Ala | Gly | Asn | Cys | Ser | Ser | His | Gly | Gly | Asn | Gly | Gly | Asn | Gly | Gly |  |
|  |  |  |  | 85 |  |  |  |  | 90 |  |  |  | 95 |  |  |  |

| agc | gac | cac | cct | ggg | gga | ggc | cgc | gaa | ttc | ttc | ttc | gat | cgc | cac | cca | 336 |
|---|---|---|---|---|---|---|---|---|---|---|---|---|---|---|---|---|
| Ser | Asp | His | Pro | Gly | Gly | Gly | Arg | Glu | Phe | Phe | Phe | Asp | Arg | His | Pro |  |
|  |  |  | 100 |  |  |  |  | 105 |  |  |  |  | 110 |  |  |  |

| gga | gta | ttc | gcc | tat | gtg | ctc | aat | tac | tac | cgc | acg | ggc | aag | ctg | cac | 384 |
|---|---|---|---|---|---|---|---|---|---|---|---|---|---|---|---|---|
| Gly | Val | Phe | Ala | Tyr | Val | Leu | Asn | Tyr | Tyr | Arg | Thr | Gly | Lys | Leu | His |  |
|  |  | 115 |  |  |  |  | 120 |  |  |  |  | 125 |  |  |  |  |

| tgc | ccc | gcc | gac | gtg | tgc | ggg | ccg | ctc | ttc | gag | gaa | gag | ctg | gct | ttc | 432 |
|---|---|---|---|---|---|---|---|---|---|---|---|---|---|---|---|---|
| Cys | Pro | Ala | Asp | Val | Cys | Gly | Pro | Leu | Phe | Glu | Glu | Glu | Leu | Ala | Phe |  |
| 130 |  |  |  |  | 135 |  |  |  |  | 140 |  |  |  |  |  |  |

| tgg | ggc | atc | gat | gag | acc | gac | gtg | gag | ccc | tgc | tgc | tgg | atg | acc | tac | 480 |
|---|---|---|---|---|---|---|---|---|---|---|---|---|---|---|---|---|
| Trp | Gly | Ile | Asp | Glu | Thr | Asp | Val | Glu | Pro | Cys | Cys | Trp | Met | Thr | Tyr |  |
| 145 |  |  |  | 150 |  |  |  |  | 155 |  |  |  |  | 160 |  |  |

| agg | cag | cac | cgg | gac | gcg | gag | gag | gcc | ctg | gac | atc | ttt | gag | aca | ccc | 528 |
|---|---|---|---|---|---|---|---|---|---|---|---|---|---|---|---|---|
| Arg | Gln | His | Arg | Asp | Ala | Glu | Glu | Ala | Leu | Asp | Ile | Phe | Glu | Thr | Pro |  |
|  |  |  | 165 |  |  |  |  | 170 |  |  |  |  | 175 |  |  |  |

| gac | ctc | atc | ggg | ggc | gac | cct | ggt | gat | gat | gag | gac | cta | gcg | gcc | aag | 576 |
|---|---|---|---|---|---|---|---|---|---|---|---|---|---|---|---|---|
| Asp | Leu | Ile | Gly | Gly | Asp | Pro | Gly | Asp | Asp | Glu | Asp | Leu | Ala | Ala | Lys |  |
|  |  |  | 180 |  |  |  |  | 185 |  |  |  |  | 190 |  |  |  |

| aga | ttg | ggc | att | gag | gat | gct | gcg | ggg | ctg | gga | gga | ccc | gat | ggc | aag | 624 |
|---|---|---|---|---|---|---|---|---|---|---|---|---|---|---|---|---|
| Arg | Leu | Gly | Ile | Glu | Asp | Ala | Ala | Gly | Leu | Gly | Gly | Pro | Asp | Gly | Lys |  |
|  |  | 195 |  |  |  |  | 200 |  |  |  |  | 205 |  |  |  |  |

| tca | ggc | cgc | tgg | agg | aag | ctg | cag | cct | cgc | atg | tgg | gct | ctt | ttt | gag | 672 |
|---|---|---|---|---|---|---|---|---|---|---|---|---|---|---|---|---|
| Ser | Gly | Arg | Trp | Arg | Lys | Leu | Gln | Pro | Arg | Met | Trp | Ala | Leu | Phe | Glu |  |
|  | 210 |  |  |  |  | 215 |  |  |  |  | 220 |  |  |  |  |  |

| gac | ccc | tac | tca | tct | aga | gcc | gct | agg | ttt | att | gct | ttt | gct | tct | ttg | 720 |
|---|---|---|---|---|---|---|---|---|---|---|---|---|---|---|---|---|
| Asp | Pro | Tyr | Ser | Ser | Arg | Ala | Ala | Arg | Phe | Ile | Ala | Phe | Ala | Ser | Leu |  |
| 225 |  |  |  | 230 |  |  |  |  | 235 |  |  |  |  | 240 |  |  |

| ttc | ttc | att | ttg | gtt | tcc | atc | aca | acc | ttt | tgc | ctg | gag | aca | cat | gaa | 768 |
|---|---|---|---|---|---|---|---|---|---|---|---|---|---|---|---|---|
| Phe | Phe | Ile | Leu | Val | Ser | Ile | Thr | Thr | Phe | Cys | Leu | Glu | Thr | His | Glu |  |
|  |  |  | 245 |  |  |  |  | 250 |  |  |  |  | 255 |  |  |  |

| gct | ttc | aat | att | gtt | aaa | aac | aag | acg | gag | ccc | gtc | atc | aat | ggc | acc | 816 |
|---|---|---|---|---|---|---|---|---|---|---|---|---|---|---|---|---|
| Ala | Phe | Asn | Ile | Val | Lys | Asn | Lys | Thr | Glu | Pro | Val | Ile | Asn | Gly | Thr |  |
|  |  |  | 260 |  |  |  |  | 265 |  |  |  |  | 270 |  |  |  |

| agc | ccg | gtc | ctc | cag | tac | gaa | atc | gaa | acg | gat | ccc | gcc | ctg | acg | tac | 864 |
|---|---|---|---|---|---|---|---|---|---|---|---|---|---|---|---|---|
| Ser | Pro | Val | Leu | Gln | Tyr | Glu | Ile | Glu | Thr | Asp | Pro | Ala | Leu | Thr | Tyr |  |
|  |  | 275 |  |  |  |  | 280 |  |  |  |  | 285 |  |  |  |  |

| gtg | gaa | gga | gta | tgt | gtg | gtg | tgg | ttt | acg | ttt | gaa | ttt | tta | gtc | cga | 912 |
|---|---|---|---|---|---|---|---|---|---|---|---|---|---|---|---|---|
| Val | Glu | Gly | Val | Cys | Val | Val | Trp | Phe | Thr | Phe | Glu | Phe | Leu | Val | Arg |  |
|  | 290 |  |  |  |  | 295 |  |  |  |  | 300 |  |  |  |  |  |

| att | gtt | ttc | tca | ccc | aat | aaa | ctt | gaa | ttc | atc | aaa | aat | ctc | ttg | aac | 960 |
|---|---|---|---|---|---|---|---|---|---|---|---|---|---|---|---|---|
| Ile | Val | Phe | Ser | Pro | Asn | Lys | Leu | Glu | Phe | Ile | Lys | Asn | Leu | Leu | Asn |  |
| 305 |  |  |  | 310 |  |  |  |  | 315 |  |  |  |  | 320 |  |  |

| atc | att | gac | ttt | gtg | gcc | atc | ctc | ccc | ttc | tac | cta | gag | gtg | gga | ctc | 1008 |
|---|---|---|---|---|---|---|---|---|---|---|---|---|---|---|---|---|
| Ile | Ile | Asp | Phe | Val | Ala | Ile | Leu | Pro | Phe | Tyr | Leu | Glu | Val | Gly | Leu |  |
|  |  |  | 325 |  |  |  |  | 330 |  |  |  |  | 335 |  |  |  |

| agc | ggg | ctg | tcc | tcc | aaa | gcg | gcc | aaa | gat | gtg | ctc | ggc | ttt | ctc | agg | 1056 |
|---|---|---|---|---|---|---|---|---|---|---|---|---|---|---|---|---|
| Ser | Gly | Leu | Ser | Ser | Lys | Ala | Ala | Lys | Asp | Val | Leu | Gly | Phe | Leu | Arg |  |
|  | 340 |  |  |  |  | 345 |  |  |  |  | 350 |  |  |  |  |  |

| gtg | gtt | agg | ttt | gtg | agg | atc | ctg | aga | atc | ttc | aag | ctc | acc | cgc | cat | 1104 |

```

Val Val Arg Phe Val Arg Ile Leu Arg Ile Phe Lys Leu Thr Arg His
        355                 360                 365 ttc gta ggt ctg agg gtg ctc gga cat act ctt cgg gcg agc acc aac    1152
Phe Val Gly Leu Arg Val Leu Gly His Thr Leu Arg Ala Ser Thr Asn
        370                 375                 380 gaa ttt ttg ttg ctg atc atc ttc ctg gcg ctg gga gtt ttg ata ttc    1200
Glu Phe Leu Leu Leu Ile Ile Phe Leu Ala Leu Gly Val Leu Ile Phe
385                 390                 395                 400 gct acg atg atc tac tac gct gag aga gta ggg gct cag ccc aat gac    1248
Ala Thr Met Ile Tyr Tyr Ala Glu Arg Val Gly Ala Gln Pro Asn Asp
                405                 410                 415 cct tca gct agt gag cac acg cag ttc aaa aac atc ccc att ggt ttc    1296
Pro Ser Ala Ser Glu His Thr Gln Phe Lys Asn Ile Pro Ile Gly Phe
        420                 425                 430 tgg tgg gcc gta gtg acc atg act acc tta ggt tac ggg gat atg tac    1344
Trp Trp Ala Val Val Thr Met Thr Thr Leu Gly Tyr Gly Asp Met Tyr
        435                 440                 445 ccc caa aca tgg tca ggg atg ttg gtg ggg gcc ttg tgt gcc ctg gcc    1392
Pro Gln Thr Trp Ser Gly Met Leu Val Gly Ala Leu Cys Ala Leu Ala
        450                 455                 460 gga gtg ctg aca ata gcc atg cct gtg cct gtc att gtc aac aat ttt    1440
Gly Val Leu Thr Ile Ala Met Pro Val Pro Val Ile Val Asn Asn Phe
465                 470                 475                 480 gga atg tac tac tcc ttg gca atg gcg aag cag aaa ctt cca aga aag    1488
Gly Met Tyr Tyr Ser Leu Ala Met Ala Lys Gln Lys Leu Pro Arg Lys
                485                 490                 495 aga aag aag cat att cct cct gcc cct ctg gca agc tcg cct aca ttt    1536
Arg Lys Lys His Ile Pro Pro Ala Pro Leu Ala Ser Ser Pro Thr Phe
                500                 505                 510 tgc aag aca gaa ttg aac atg gct tgc aac agt acc cag agt gac aca    1584
Cys Lys Thr Glu Leu Asn Met Ala Cys Asn Ser Thr Gln Ser Asp Thr
        515                 520                 525 tgt ctg ggc aaa gaa aac cgg ctt ctg gaa cat aac aga tca gtg tta    1632
Cys Leu Gly Lys Glu Asn Arg Leu Leu Glu His Asn Arg Ser Val Leu
530                 535                 540 tca ggt gac gac agt aca gga agt gag ccg cca tta tca cct cca gaa    1680
Ser Gly Asp Asp Ser Thr Gly Ser Glu Pro Pro Leu Ser Pro Pro Glu
545                 550                 555                 560 agg ctc cct atc aga cgc tct agt acc aga gac aaa aac aga aga ggg    1728
Arg Leu Pro Ile Arg Arg Ser Ser Thr Arg Asp Lys Asn Arg Arg Gly
                565                 570                 575 gaa acg tgt ttc ctg ttg acg aca ggt gat tac acg tgc gct tct gat    1776
Glu Thr Cys Phe Leu Leu Thr Thr Gly Asp Tyr Thr Cys Ala Ser Asp
                580                 585                 590 gga gga atc agg aaa gtg ttg tac aga att tat cat gga ttt ttg act    1824
Gly Gly Ile Arg Lys Val Leu Tyr Arg Ile Tyr His Gly Phe Leu Thr
                595                 600                 605 gct gaa aaa aaa gga cat tga                                        1845
Ala Glu Lys Lys Gly His
        610

<210> SEQ ID NO 51
<211> LENGTH: 614
<212> TYPE: PRT
<213> ORGANISM: Mus musculus

<400> SEQUENCE: 51

Met Gly Lys Ile Glu Ser Asn Glu Arg Val Ile Leu Asn Val Gly Gly
1               5                   10                  15

Thr Arg His Glu Thr Tyr Arg Ser Thr Leu Lys Thr Leu Pro Gly Thr
```

```
                    20                  25                  30
Arg Leu Ala Leu Leu Ala Ser Ser Glu Pro Gln Gly Asp Cys Leu Thr
                35                  40                  45
Ala Ala Gly Asp Lys Leu Gln Pro Leu Pro Pro Leu Ser Pro Pro
        50                  55                  60
Pro Arg Pro Pro Pro Leu Ser Pro Val Pro Ser Gly Cys Phe Glu Gly
 65                  70                  75                  80
Gly Ala Gly Asn Cys Ser Ser His Gly Gly Asn Gly Gly Asn Gly Gly
                    85                  90                  95
Ser Asp His Pro Gly Gly Gly Arg Glu Phe Phe Asp Arg His Pro
                100                 105                 110
Gly Val Phe Ala Tyr Val Leu Asn Tyr Tyr Arg Thr Gly Lys Leu His
                115                 120                 125
Cys Pro Ala Asp Val Cys Gly Pro Leu Phe Glu Glu Leu Ala Phe
                130                 135                 140
Trp Gly Ile Asp Glu Thr Asp Val Glu Pro Cys Cys Trp Met Thr Tyr
145                 150                 155                 160
Arg Gln His Arg Asp Ala Glu Glu Ala Leu Asp Ile Phe Glu Thr Pro
                165                 170                 175
Asp Leu Ile Gly Gly Asp Pro Gly Asp Asp Glu Asp Leu Ala Ala Lys
                180                 185                 190
Arg Leu Gly Ile Glu Asp Ala Ala Gly Leu Gly Gly Pro Asp Gly Lys
                195                 200                 205
Ser Gly Arg Trp Arg Lys Leu Gln Pro Arg Met Trp Ala Leu Phe Glu
                210                 215                 220
Asp Pro Tyr Ser Ser Arg Ala Ala Arg Phe Ile Ala Phe Ala Ser Leu
225                 230                 235                 240
Phe Phe Ile Leu Val Ser Ile Thr Thr Phe Cys Leu Glu Thr His Glu
                245                 250                 255
Ala Phe Asn Ile Val Lys Asn Lys Thr Glu Pro Val Ile Asn Gly Thr
                260                 265                 270
Ser Pro Val Leu Gln Tyr Glu Ile Glu Thr Asp Pro Ala Leu Thr Tyr
                275                 280                 285
Val Glu Gly Val Cys Val Val Trp Phe Thr Phe Glu Phe Leu Val Arg
                290                 295                 300
Ile Val Phe Ser Pro Asn Lys Leu Glu Phe Ile Lys Asn Leu Leu Asn
305                 310                 315                 320
Ile Ile Asp Phe Val Ala Ile Leu Pro Phe Tyr Leu Glu Val Gly Leu
                325                 330                 335
Ser Gly Leu Ser Ser Lys Ala Ala Lys Asp Val Leu Gly Phe Leu Arg
                340                 345                 350
Val Val Arg Phe Val Arg Ile Leu Arg Ile Phe Lys Leu Thr Arg His
                355                 360                 365
Phe Val Gly Leu Arg Val Leu Gly His Thr Leu Arg Ala Ser Thr Asn
                370                 375                 380
Glu Phe Leu Leu Leu Ile Ile Phe Leu Ala Leu Gly Val Leu Ile Phe
385                 390                 395                 400
Ala Thr Met Ile Tyr Tyr Ala Glu Arg Val Gly Ala Gln Pro Asn Asp
                405                 410                 415
Pro Ser Ala Ser Glu His Thr Gln Phe Lys Asn Ile Pro Ile Gly Phe
                420                 425                 430
Trp Trp Ala Val Val Thr Met Thr Thr Leu Gly Tyr Gly Asp Met Tyr
                435                 440                 445
```

```
Pro Gln Thr Trp Ser Gly Met Leu Val Gly Ala Leu Cys Ala Leu Ala
    450                 455                 460

Gly Val Leu Thr Ile Ala Met Pro Val Pro Val Ile Val Asn Asn Phe
465                 470                 475                 480

Gly Met Tyr Tyr Ser Leu Ala Met Ala Lys Gln Lys Leu Pro Arg Lys
                485                 490                 495

Arg Lys Lys His Ile Pro Pro Ala Pro Leu Ala Ser Ser Pro Thr Phe
            500                 505                 510

Cys Lys Thr Glu Leu Asn Met Ala Cys Asn Ser Thr Gln Ser Asp Thr
        515                 520                 525

Cys Leu Gly Lys Glu Asn Arg Leu Leu Glu His Asn Arg Ser Val Leu
    530                 535                 540

Ser Gly Asp Asp Ser Thr Gly Ser Glu Pro Pro Leu Ser Pro Pro Glu
545                 550                 555                 560

Arg Leu Pro Ile Arg Arg Ser Ser Thr Arg Asp Lys Asn Arg Arg Gly
                565                 570                 575

Glu Thr Cys Phe Leu Leu Thr Thr Gly Asp Tyr Thr Cys Ala Ser Asp
            580                 585                 590

Gly Gly Ile Arg Lys Val Leu Tyr Arg Ile Tyr His Gly Phe Leu Thr
        595                 600                 605

Ala Glu Lys Lys Gly His
    610

<210> SEQ ID NO 52
<211> LENGTH: 1968
<212> TYPE: DNA
<213> ORGANISM: Mus musculus
<220> FEATURE:
<221> NAME/KEY: CDS
<222> LOCATION: (1)..(1965)

<400> SEQUENCE: 52 atg ggc aag atc gag agc aac gag agg gtg atc ctc aat gtc ggg ggt      48
Met Gly Lys Ile Glu Ser Asn Glu Arg Val Ile Leu Asn Val Gly Gly
1               5                   10                  15 acc agg cac gaa acc tac cgc agc acc ctc aag acc ctg cct gga act      96
Thr Arg His Glu Thr Tyr Arg Ser Thr Leu Lys Thr Leu Pro Gly Thr
            20                  25                  30 cgc ctg gcc ctt ctt gcc tcc tct gaa cct cag ggc gac tgc ctg act     144
Arg Leu Ala Leu Leu Ala Ser Ser Glu Pro Gln Gly Asp Cys Leu Thr
        35                  40                  45 gcg gcc ggg gac aag ctg caa ccg ctg ccc cct ccg ctg tct ccg ccg     192
Ala Ala Gly Asp Lys Leu Gln Pro Leu Pro Pro Pro Leu Ser Pro Pro
    50                  55                  60 cca cga ccg cct ccc ttg tcc cct gtc ccc agc ggc tgc ttc gag ggc     240
Pro Arg Pro Pro Pro Leu Ser Pro Val Pro Ser Gly Cys Phe Glu Gly
65                  70                  75                  80 ggc gca ggc aac tgc agt tcg cac ggt ggc aac ggc ggc aac ggc ggc     288
Gly Ala Gly Asn Cys Ser Ser His Gly Gly Asn Gly Gly Asn Gly Gly
                85                  90                  95 agc gac cac cct ggg gga ggc cgc gaa ttc ttc ttt gat cgc cac cca     336
Ser Asp His Pro Gly Gly Gly Arg Glu Phe Phe Phe Asp Arg His Pro
            100                 105                 110 gga gta ttc gcc tat gtg ctc aat tac tac cgc acg ggc aag ctg cac     384
Gly Val Phe Ala Tyr Val Leu Asn Tyr Tyr Arg Thr Gly Lys Leu His
        115                 120                 125 tgc ccc gcc gac gtg tgc ggg ccg ctc ttc gag gaa gag ctg gct ttc     432
Cys Pro Ala Asp Val Cys Gly Pro Leu Phe Glu Glu Glu Leu Ala Phe
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 130 |     |     |     |     | 135 |     |     |     |     | 140 |     |     |     |      |
| tgg | ggc | atc | gat | gag | acc | gac | gtg | gag | ccc | tgc | tgc | tgg | atg | acc | tac | 480  |
| Trp | Gly | Ile | Asp | Glu | Thr | Asp | Val | Glu | Pro | Cys | Cys | Trp | Met | Thr | Tyr |      |
| 145 |     |     |     |     | 150 |     |     |     |     | 155 |     |     |     |     | 160 |      |
| agg | cag | cac | cgg | gac | gcg | gag | gag | gcc | ctg | gac | atc | ttt | gag | aca | ccc | 528  |
| Arg | Gln | His | Arg | Asp | Ala | Glu | Glu | Ala | Leu | Asp | Ile | Phe | Glu | Thr | Pro |      |
|     |     |     |     | 165 |     |     |     |     | 170 |     |     |     |     | 175 |     |      |
| gac | ctc | atc | ggg | ggc | gac | cct | ggt | gat | gat | gag | gac | cta | gcg | gcc | aag | 576  |
| Asp | Leu | Ile | Gly | Gly | Asp | Pro | Gly | Asp | Asp | Glu | Asp | Leu | Ala | Ala | Lys |      |
|     |     |     | 180 |     |     |     |     | 185 |     |     |     |     | 190 |     |     |      |
| aga | ttg | ggc | att | gag | gat | gct | gcg | ggg | ctg | gga | gga | ccc | gat | ggc | aag | 624  |
| Arg | Leu | Gly | Ile | Glu | Asp | Ala | Ala | Gly | Leu | Gly | Gly | Pro | Asp | Gly | Lys |      |
|     |     | 195 |     |     |     |     | 200 |     |     |     |     | 205 |     |     |     |      |
| tca | ggc | cgc | tgg | agg | aag | ctg | cag | cct | cgc | atg | tgg | gct | ctt | ttt | gag | 672  |
| Ser | Gly | Arg | Trp | Arg | Lys | Leu | Gln | Pro | Arg | Met | Trp | Ala | Leu | Phe | Glu |      |
| 210 |     |     |     |     | 215 |     |     |     |     | 220 |     |     |     |     |     |      |
| gac | ccc | tac | tca | tct | aga | gcc | gct | agg | ttt | att | gct | ttt | gct | tct | ttg | 720  |
| Asp | Pro | Tyr | Ser | Ser | Arg | Ala | Ala | Arg | Phe | Ile | Ala | Phe | Ala | Ser | Leu |      |
| 225 |     |     |     |     | 230 |     |     |     |     | 235 |     |     |     |     | 240 |      |
| ttc | ttc | att | ttg | gtt | tcc | atc | aca | acc | ttt | tgc | ctg | gag | aca | cat | gaa | 768  |
| Phe | Phe | Ile | Leu | Val | Ser | Ile | Thr | Thr | Phe | Cys | Leu | Glu | Thr | His | Glu |      |
|     |     |     |     | 245 |     |     |     |     | 250 |     |     |     |     | 255 |     |      |
| gct | ttc | aat | att | gtt | aaa | aac | aag | acg | gag | ccc | gtc | atc | aat | ggc | acc | 816  |
| Ala | Phe | Asn | Ile | Val | Lys | Asn | Lys | Thr | Glu | Pro | Val | Ile | Asn | Gly | Thr |      |
|     |     |     | 260 |     |     |     |     | 265 |     |     |     |     | 270 |     |     |      |
| agc | ccg | gtc | ctc | cag | tac | gaa | atc | gaa | acg | gat | ccc | gcc | ctg | acg | tac | 864  |
| Ser | Pro | Val | Leu | Gln | Tyr | Glu | Ile | Glu | Thr | Asp | Pro | Ala | Leu | Thr | Tyr |      |
|     |     | 275 |     |     |     |     | 280 |     |     |     |     | 285 |     |     |     |      |
| gtg | gaa | gga | gta | tgt | gtg | gtg | tgg | ttt | acg | ttt | gaa | ttt | tta | gtc | cga | 912  |
| Val | Glu | Gly | Val | Cys | Val | Val | Trp | Phe | Thr | Phe | Glu | Phe | Leu | Val | Arg |      |
| 290 |     |     |     |     | 295 |     |     |     |     | 300 |     |     |     |     |     |      |
| att | gtt | ttc | tca | ccc | aat | aaa | ctt | gaa | ttc | atc | aaa | aat | ctc | ttg | aac | 960  |
| Ile | Val | Phe | Ser | Pro | Asn | Lys | Leu | Glu | Phe | Ile | Lys | Asn | Leu | Leu | Asn |      |
| 305 |     |     |     |     | 310 |     |     |     |     | 315 |     |     |     |     | 320 |      |
| atc | att | gac | ttt | gtg | gcc | atc | ctc | ccc | ttc | tac | cta | gag | gtg | gga | ctc | 1008 |
| Ile | Ile | Asp | Phe | Val | Ala | Ile | Leu | Pro | Phe | Tyr | Leu | Glu | Val | Gly | Leu |      |
|     |     |     |     | 325 |     |     |     |     | 330 |     |     |     |     | 335 |     |      |
| agc | ggg | ctg | tcc | tcc | aaa | gcg | gcc | aaa | gat | gtg | ctc | ggc | ttt | ctc | agg | 1056 |
| Ser | Gly | Leu | Ser | Ser | Lys | Ala | Ala | Lys | Asp | Val | Leu | Gly | Phe | Leu | Arg |      |
|     |     |     | 340 |     |     |     |     | 345 |     |     |     |     | 350 |     |     |      |
| gtg | gtt | agg | ttt | gtg | agg | atc | ctg | aga | atc | ttc | aag | ctc | acc | cgc | cat | 1104 |
| Val | Val | Arg | Phe | Val | Arg | Ile | Leu | Arg | Ile | Phe | Lys | Leu | Thr | Arg | His |      |
|     |     | 355 |     |     |     |     | 360 |     |     |     |     | 365 |     |     |     |      |
| ttc | gta | ggt | ctg | agg | gtg | ctc | gga | cat | act | ctt | cgg | gcg | agc | acc | aac | 1152 |
| Phe | Val | Gly | Leu | Arg | Val | Leu | Gly | His | Thr | Leu | Arg | Ala | Ser | Thr | Asn |      |
| 370 |     |     |     |     | 375 |     |     |     |     | 380 |     |     |     |     |     |      |
| gaa | ttt | ttg | ttg | ctg | atc | atc | ttc | ctg | gcg | ctg | gga | gtt | tgt | ata | ttc | 1200 |
| Glu | Phe | Leu | Leu | Leu | Ile | Ile | Phe | Leu | Ala | Leu | Gly | Val | Leu | Ile | Phe |      |
| 385 |     |     |     |     | 390 |     |     |     |     | 395 |     |     |     |     | 400 |      |
| gct | acg | atg | atc | tac | tac | gct | gag | aga | gta | ggg | gct | cag | ccc | aat | gac | 1248 |
| Ala | Thr | Met | Ile | Tyr | Tyr | Ala | Glu | Arg | Val | Gly | Ala | Gln | Pro | Asn | Asp |      |
|     |     |     |     | 405 |     |     |     |     | 410 |     |     |     |     | 415 |     |      |
| cct | tca | gct | agt | gag | cac | acg | cag | ttc | aaa | aac | atc | ccc | att | ggt | ttc | 1296 |
| Pro | Ser | Ala | Ser | Glu | His | Thr | Gln | Phe | Lys | Asn | Ile | Pro | Ile | Gly | Phe |      |
|     |     |     | 420 |     |     |     |     | 425 |     |     |     |     | 430 |     |     |      |
| tgg | tgg | gcc | gta | gtg | acc | atg | act | acc | tta | ggt | tac | ggg | gat | atg | tac | 1344 |
| Trp | Trp | Ala | Val | Val | Thr | Met | Thr | Thr | Leu | Gly | Tyr | Gly | Asp | Met | Tyr |      |
|     |     | 435 |     |     |     |     | 440 |     |     |     |     | 445 |     |     |     |      |
| ccc | caa | aca | tgg | tca | ggg | atg | ttg | gtg | ggg | gcc | ttg | tgt | gcc | ctg | gcc | 1392 |

```
Pro Gln Thr Trp Ser Gly Met Leu Val Gly Ala Leu Cys Ala Leu Ala
    450                 455                 460 gga gtg ctg aca ata gcc atg cct gtg cct gtc att gtc aac aat ttt    1440
Gly Val Leu Thr Ile Ala Met Pro Val Pro Val Ile Val Asn Asn Phe
465                 470                 475                 480 gga atg tac tac tcc ttg gca atg gcg aag cag aaa ctt cca aga aag    1488
Gly Met Tyr Tyr Ser Leu Ala Met Ala Lys Gln Lys Leu Pro Arg Lys
                485                 490                 495 aga aag aag cat att cct cct gcc cct ctg gca agc tcg cct aca ttt    1536
Arg Lys Lys His Ile Pro Pro Ala Pro Leu Ala Ser Ser Pro Thr Phe
            500                 505                 510 tgc aag aca gaa ttg aac atg gct tgc aac agt acc cag agt gac aca    1584
Cys Lys Thr Glu Leu Asn Met Ala Cys Asn Ser Thr Gln Ser Asp Thr
        515                 520                 525 tgt ctg ggc aaa gaa aac cgg ctt ctg gaa cat aac aga tca gtg tta    1632
Cys Leu Gly Lys Glu Asn Arg Leu Leu Glu His Asn Arg Ser Val Leu
    530                 535                 540 tca ggt gac gac agt aca gga agt gag ccg cca tta tca cct cca gaa    1680
Ser Gly Asp Asp Ser Thr Gly Ser Glu Pro Pro Leu Ser Pro Pro Glu
545                 550                 555                 560 agg ctc cct atc aga cgc tct agt acc aga gac aaa aac aga aga ggg    1728
Arg Leu Pro Ile Arg Arg Ser Ser Thr Arg Asp Lys Asn Arg Arg Gly
                565                 570                 575 gaa acg tgt ttc ctg ttg acg aca ggt gat tac acg tgc gct tct gat    1776
Glu Thr Cys Phe Leu Leu Thr Thr Gly Asp Tyr Thr Cys Ala Ser Asp
            580                 585                 590 gga gga atc agg aaa gaa gag gtc ccg cat ctt atg agg cat tta aag    1824
Gly Gly Ile Arg Lys Glu Glu Val Pro His Leu Met Arg His Leu Lys
        595                 600                 605 ctt ata aaa ggg act gtg gct gga act gag atg gtg ctc gcc atg gga    1872
Leu Ile Lys Gly Thr Val Ala Gly Thr Glu Met Val Leu Ala Met Gly
    610                 615                 620 ata ttc tgc ttg tcg aca gac ctg agt cca cgg aac agc tgt aaa tac    1920
Ile Phe Cys Leu Ser Thr Asp Leu Ser Pro Arg Asn Ser Cys Lys Tyr
625                 630                 635                 640 caa ccg tgt gca tgg acc tgc cca ctc tca ccg tct cat aga cag tga    1968
Gln Pro Cys Ala Trp Thr Cys Pro Leu Ser Pro Ser His Arg Gln
                645                 650                 655

<210> SEQ ID NO 53
<211> LENGTH: 655
<212> TYPE: PRT
<213> ORGANISM: Mus musculus

<400> SEQUENCE: 53

Met Gly Lys Ile Glu Ser Asn Glu Arg Val Ile Leu Asn Val Gly Gly
1               5                   10                  15

Thr Arg His Glu Thr Tyr Arg Ser Thr Leu Lys Thr Leu Pro Gly Thr
            20                  25                  30

Arg Leu Ala Leu Leu Ala Ser Ser Glu Pro Gln Gly Asp Cys Leu Thr
        35                  40                  45

Ala Ala Gly Asp Lys Leu Gln Pro Leu Pro Pro Leu Ser Pro Pro
    50                  55                  60

Pro Arg Pro Pro Leu Ser Val Pro Ser Gly Cys Phe Glu Gly
65                  70                  75                  80

Gly Ala Gly Asn Cys Ser Ser His Gly Gly Asn Gly Asn Gly
                85                  90                  95

Ser Asp His Pro Gly Gly Gly Arg Glu Phe Phe Asp Arg His Pro
            100                 105                 110
```

```
Gly Val Phe Ala Tyr Val Leu Asn Tyr Tyr Arg Thr Gly Lys Leu His
            115                 120                 125

Cys Pro Ala Asp Val Cys Gly Pro Leu Phe Glu Glu Glu Leu Ala Phe
        130                 135                 140

Trp Gly Ile Asp Glu Thr Asp Val Glu Pro Cys Cys Trp Met Thr Tyr
145                 150                 155                 160

Arg Gln His Arg Asp Ala Glu Ala Leu Asp Ile Phe Glu Thr Pro
                165                 170                 175

Asp Leu Ile Gly Gly Asp Pro Gly Asp Glu Asp Leu Ala Ala Lys
        180                 185                 190

Arg Leu Gly Ile Glu Asp Ala Ala Gly Leu Gly Gly Pro Asp Gly Lys
            195                 200                 205

Ser Gly Arg Trp Arg Lys Leu Gln Pro Arg Met Trp Ala Leu Phe Glu
    210                 215                 220

Asp Pro Tyr Ser Ser Arg Ala Ala Arg Phe Ile Ala Phe Ala Ser Leu
225                 230                 235                 240

Phe Phe Ile Leu Val Ser Ile Thr Thr Phe Cys Leu Glu Thr His Glu
                245                 250                 255

Ala Phe Asn Ile Val Lys Asn Lys Thr Glu Pro Val Ile Asn Gly Thr
            260                 265                 270

Ser Pro Val Leu Gln Tyr Glu Ile Glu Thr Asp Pro Ala Leu Thr Tyr
    275                 280                 285

Val Glu Gly Val Cys Val Val Trp Phe Thr Phe Glu Phe Leu Val Arg
            290                 295                 300

Ile Val Phe Ser Pro Asn Lys Leu Glu Phe Ile Lys Asn Leu Leu Asn
305                 310                 315                 320

Ile Ile Asp Phe Val Ala Ile Leu Pro Phe Tyr Leu Glu Val Gly Leu
                325                 330                 335

Ser Gly Leu Ser Ser Lys Ala Ala Lys Asp Val Leu Gly Phe Leu Arg
    340                 345                 350

Val Val Arg Phe Val Arg Ile Leu Arg Ile Phe Lys Leu Thr Arg His
        355                 360                 365

Phe Val Gly Leu Arg Val Leu Gly His Thr Leu Arg Ala Ser Thr Asn
370                 375                 380

Glu Phe Leu Leu Leu Ile Ile Phe Leu Ala Leu Gly Val Leu Ile Phe
385                 390                 395                 400

Ala Thr Met Ile Tyr Tyr Ala Glu Arg Val Gly Ala Gln Pro Asn Asp
                405                 410                 415

Pro Ser Ala Ser Glu His Thr Gln Phe Lys Asn Ile Pro Ile Gly Phe
        420                 425                 430

Trp Trp Ala Val Val Thr Met Thr Thr Leu Gly Tyr Gly Asp Met Tyr
            435                 440                 445

Pro Gln Thr Trp Ser Gly Met Leu Val Gly Ala Leu Cys Ala Leu Ala
    450                 455                 460

Gly Val Leu Thr Ile Ala Met Pro Val Pro Val Ile Val Asn Asn Phe
465                 470                 475                 480

Gly Met Tyr Tyr Ser Leu Ala Met Ala Lys Gln Lys Leu Pro Arg Lys
                485                 490                 495

Arg Lys Lys His Ile Pro Pro Ala Pro Leu Ala Ser Ser Pro Thr Phe
            500                 505                 510

Cys Lys Thr Glu Leu Asn Met Ala Cys Asn Ser Thr Gln Ser Asp Thr
        515                 520                 525
```

-continued

```
Cys Leu Gly Lys Glu Asn Arg Leu Leu Glu His Asn Arg Ser Val Leu
    530                 535                 540
Ser Gly Asp Asp Ser Thr Gly Ser Glu Pro Pro Leu Ser Pro Pro Glu
545                 550                 555                 560
Arg Leu Pro Ile Arg Arg Ser Ser Thr Arg Asp Lys Asn Arg Arg Gly
                565                 570                 575
Glu Thr Cys Phe Leu Leu Thr Thr Gly Asp Tyr Thr Cys Ala Ser Asp
            580                 585                 590
Gly Gly Ile Arg Lys Glu Val Pro His Leu Met Arg His Leu Lys
        595                 600                 605
Leu Ile Lys Gly Thr Val Ala Gly Thr Glu Met Val Leu Ala Met Gly
    610                 615                 620
Ile Phe Cys Leu Ser Thr Asp Leu Ser Pro Arg Asn Ser Cys Lys Tyr
625                 630                 635                 640
Gln Pro Cys Ala Trp Thr Cys Pro Leu Ser Pro Ser His Arg Gln
                645                 650                 655
```

METHOD FOR SCREENING A SALTY TASTE MODULATING SUBSTANCE

TECHNICAL FIELD

The present invention relates to a method for screening a salty taste modulating substance including a substance that alternatively shows a salty taste, or modifies a salty taste. A salt alternative or a salty taste modulating substance are useful in the field of food industry and so forth.

BACKGROUND ART

Taste is important for detection of nutritional components or harmful components in foodstuffs. Taste perception of mammals is attained with the taste receptor cells contained in the taste buds present in the oral cavity. The received signals are transmitted from the taste receptor cells to taste nerves entering into the taste buds, and to the central nerve system. Tastes sensed by mammals are generally divided into five kinds of fundamental quality of tastes, that is, sweet taste, bitter taste, acid taste, salty taste, and umami taste, and these are called five basic tastes.

The receptors for these five basic tastes are being elucidated in accordance with the progress of researches in recent years (Non-patent documents 1 and 2). Identification and isolation of novel taste receptors enable novel methods of modulating taste perception. For example, search of highly affinitive agonists or antagonists using taste receptors enables screening for taste modulating substances. Such taste modulating substances may provide improvement or refinement of quality of tastes in various consumer products.

Salty taste, one of the five basic tastes, is involved in detection of sodium ions or other inorganic cations, and is very important for maintenance of internal homeostasis. It is considered that, as salty taste perception pathways, there are the amiloride-sensitive pathway which is inhibited by diuretic amiloride, and the amiloride-insensitive pathway which is not affected by amiloride (Non-patent document 3). Molecules involved in both the salty taste perception pathways exist and function in the taste receptor cells in the taste buds (Non-patent document 2).

It is considered that the amiloride-sensitive pathway is mediated by the epithelial sodium channel (ENaC). ENaC is composed of four kinds of subunits, α, β, γ, and δ, and functions as a hetero-multimer consisting of a combination of α, β and γ, or δ, β and γ (Non-patent document 13). However, although marked inhibition of the salty taste perception by amiloride is observed in rodents, such inhibition is observed in only a part of humans, and presence of a different receptor in the human salty taste perception mechanism is suggested. As described above, a significant part of the salty taste perception mechanism including receptors still remains unknown.

Excessive intake of salt from foodstuffs is considered as one of the risk factors of hypertension or cardiovascular system diseases, and there is movement of restricting salt consumption worldwide, including Japan (World Health Organization, Non-patent document 4).

There have been conventional techniques for decreasing intake of salt, for example, low-salt seasonings and low-salt food using potassium chloride as a substitute for sodium chloride. However, potassium chloride has a problem that it has a bitter taste and an irritating taste. Therefore, taste of food using potassium chloride is markedly inferior. In order to improve this drawback, there have been developed a seasoning composition in addition to potassium chloride, such as a mixture of ammonium chloride, calcium lactate, sodium L-aspartate, an L-glutamic acid salt and/or a nucleic acid type taste substance at a specific ratio (Patent document 1), a low sodium salty taste seasoning containing ascorbic acid (Patent document 2), a bitterness suppressing method using carrageenan (Patent document 3), and so forth. However, salt reduction techniques do not reach such a level that unpleasant tastes other than salty taste are eliminated, and salty taste intensity equivalent to that of sodium chloride is provided at the same time.

Furthermore, there are salt reduction methods using a salty taste enhancing substance, which does not reduce salty taste intensity even if sodium chloride is reduced. For example, it is known that a basic amino acid, especially L-arginine, has an effect of enhancing salty taste (Non-patent documents 5 and 6). As techniques applying the above knowledge, there have been developed a combination of L-arginine, L-aspartic acid and sodium chloride (Patent document 4), a taste improving agent using neutralized salts of a basic amino acid and citric acid (Patent document 5), and so forth. However, any technique that can sufficiently compensate insufficiency by reduction of sodium chloride has not been developed yet, in view of salt reduction effect, flavor, salty taste intensity and so forth.

Meanwhile, the Kv3 family is known as a family of potassium channel that is originally considered to function in a nerve cell that shows stimulation at high frequency, and release potassium ions when cell membrane potential is depolarized to −20 mV or higher to show outward current (Non-patent document 7). However, for these, only the function as a voltage-dependent potassium channel is known (Non-patent documents 8 to 11), and a function as a cation channel depending on extracellular sodium concentration around the resting membrane potential (about −60 to −80 mV) is not known at all.

In connection with taste, expression of Kv3.1 and Kv3.2 genes confirmed by PCR in taste cells isolated from rat fungiform papillae has been reported (Non-patent document 12). However, functions thereof in the taste cells are not known at all.

PRIOR ART REFERENCES

Patent Documents

Patent document 1: Japanese Patent Laid-open (KOKAI) No. 11-187841
Patent document 2: Japanese Patent Laid-open No. 1-281054
Patent document 3: Japanese Patent Laid-open No. 4-262758
Patent document 4: U.S. Pat. No. 5,145,707
Patent document 5: Japanese Patent Laid-open No. 2003-0144088

Non-Patent Documents

Non-patent document 1: Chandrashekar, J. et al., Nature, 444:288-294 (2006)
Non-patent document 2: Bachmanov, A. A. et al., Ann. Rev. Nutr, 27:387-412 (2007)
Non-patent document 3: DeSimone, J. A. et al., Am. J. Physiol. Regulatory Integrative Comp. Physiol., 249: 52-61 (1985)
Non-patent document 4: Reducing salt intake in populations—Report a WHO Forum and Technical Meeting, [online], [searched on Sep. 20, 2009], Internet URL:

Non-patent document 5: Riha, W. et al., Chem. Senses, 22:778 (1997)

Non-patent document 6: Estrella, N. L. et al., Chem. Senses, 34:A117-8 (2009)

Non-patent document 7: Rudy, B. et al., Trends in Neuroscience, 24:517-526 (2001)

Non-patent document 8: Gutman, G. A. et al., Pharmacological Reviews 57:473-508 (2005)

Non-patent document 9: McCormack, T. et al., Proc. Natl. Acad. Sci. USA., 87:5227-5231 (1990)

Non-patent document 10: HERNANDEZ-PINEDA, R. et al., J. Neurophysiol., 82:1512-1528 (1999)

Non-patent document 11: Madeja, M. et al., Neuropharmacology, 39:202-210 (2000)

Non-patent document 12: Liu, L. et al., Am. J. Physiol. Cell Physiol., 289:868-880 (2005)

Non-patent document 13: Stahler, F. et al., Chemosensory Perception, 1:78-90 (2008)

SUMMARY OF THE INVENTION

Object to be Achieved by the Invention

An object of the present invention is to identify a salty taste receptor protein and a gene encoding the protein, and provide a screening system for searching a compound that enhances or inhibits salty taste perception or a salt alternative substance.

Means for Achieving the Object

The inventors of the present invention conceived that if a salty taste receptor or a molecule controlling such a receptor was used, it became possible to efficiently search and identify a compound that could enhance or inhibit salty taste perception or a salt alternative substance, which can result in development of effective salt reduction method that did not alter tastes, and as a result, enable production of foodstuffs having a low salt concentration with maintaining tastes. Then, they conducted various researches, as a result, succeeded in identifying molecules involved in salty taste perception, and thus accomplished the present invention.

The present invention is as follows.

(1) A method for screening a salty taste modulating substance, which comprises the step of contacting a test substance with a cell that expresses a Kv3.2 protein, and comparing observed cation influx into the cell with cation influx into the cell observed when the test substance is not contacted with the cell.

(2) The method according to (1), wherein the cation influx is measured by measuring cell membrane current of the cell in the presence of sodium ions.

(3) The method according to (1), wherein the cation influx is measured by measuring cell membrane current of the cell in the absence of sodium ion.

(4) The method according to (1) or (2) described above, wherein the salty taste modulating substance is a salty taste enhancing substance or a salty taste inhibiting substance.

(5) The method according to (1) or (3) described above, wherein the salty taste modulating substance is a salt alternative substance.

(6) The method as described above, wherein the Kv3.2 protein has the amino acid sequence of SEQ ID NO: 2, 4, 6, 8, 10, 12, 14, 16, 18, 40, 47, 49, 51 or 53.

(7) The method as described above, wherein the Kv3.2 protein shows a sequence identity of at least 78% or more to the sequence of SEQ ID NO: 2, 4, 6, 8, 10, 12, 14, 16, 18, 40, 47, 49, 51 or 53, and is able to constitute a cation channel of which activity changes according to change of extracellular sodium ion concentration.

(8) The method as described above, wherein the Kv3.2 protein has the amino acid sequence of SEQ ID NO: 2, 4, 6, 8, 10, 12, 14, 16, 18, 40, 47, 49, 51 or 53 including substitutions, deletions, insertions and/or additions of one or more amino acid residues, and is able to constitute a cation channel of which activity changes according to change of extracellular sodium ion concentration.

(9) The method as described above, wherein the Kv3.2 protein is encoded by a DNA shown in the following (a) or (b):

(a) a DNA having the nucleotide sequence of SEQ ID NO: 1, 3, 5, 7, 9, 11, 13, 15, 17, 39, 46, 48, 50 or 52;

(b) a DNA which is able to hybridize with the nucleotide sequence complementary to the nucleotide sequence of SEQ ID NO: 1, 3, 5, 7, 9, 11, 13, 15, 17, 39, 46, 48, 50 or 52, or a probe which can be prepared from the nucleotide sequence under stringent conditions, and codes for a protein that can constitute a cation channel of which activity changes according to change of extracellular sodium ion concentration.

(10) The method as described above, wherein the Kv3.2 protein is selected from Kv3.2 protein homologues derived from human, mouse, rat, frog of the genus *Xenopus*, dog, horse, chimpanzee, rhesus monkey, fowl, opossum, swine or bovine, and a mutant thereof, a fragment thereof, and a chimera protein thereof.

(11) The method as described above, wherein the cell is an oocyte into which a polynucleotide encoding a Kv3.2 protein is introduced in an expressible form.

(12) The method as described above, wherein the cell expresses a Kv3.2 gene isolated from a tissue selected from taste cell, tongue epithelium, adrenal gland, pineal body, thyroid, melanocyte and kidney.

(13) A Kv3.2 protein variant, which is a protein shown in any of the following (a) to (c):

(a) a protein having the sequence of SEQ ID NO: 47, 49, 51 or 53;

(b) a protein showing a sequence identity of at least 78% or more to the sequence of SEQ ID NO: 47, 49, 51 or 53, and being able to constitute a cation channel of which activity changes according to change of extracellular sodium ion concentration;

(c) a protein which has the amino acid sequence of SEQ ID NO: 47, 49, 51 or 53 including substitutions, deletions, insertions and/or additions of one or more amino acid residues, and is able to constitute a cation channel of which activity changes according to change of extracellular sodium ion concentration.

(14) A DNA encoding a Kv3.2 protein variant, which is a DNA shown in the following (a) or (b):

(a) a DNA having the nucleotide sequence of SEQ ID NO: 46, 48, 50 or 52;

(b) a DNA which is able to hybridize with the nucleotide sequence complementary to the nucleotide sequence of SEQ ID NO: 46, 48, 50 or 52, or a probe which can be prepared from the nucleotide sequence under stringent conditions, and codes for a protein that can constitute a cation channel of which activity changes according to change of extracellular sodium ion concentration.

(15) A method for searching a protein having a function of positively or negatively regulating the Kv3.2 activity or a protein that constitutes a salty taste receptor, which comprises identifying a gene showing an expression profile similar to that of the Kv3.2 gene or a gene of which expression is suppressed in a Kv3.2 gene-expressing cell among genes expressed in the Kv3.2 gene-expressing cell.

(16) A method for searching a salty taste modulating substance by identifying a compound that acts on a Kv3.2 protein or a cell expressing the protein.
(17) A method for searching a taste substance or a flavor substance, which comprises identifying a compound that acts on a channel or complex constituted by a Kv3.2 protein and a protein specifically expressed in a taste cell.
(18) An isolated oocyte or taste cell into which a polynucleotide encoding a Kv3.2 protein is introduced in an expressible form.

Effect of the Invention

A salty taste receptor protein identified according to the present invention constitutes a salty taste receptor ion channel expressed in a taste cell. A substance that activates this receptor is useful as a candidate substance of salty taste modulating substance, i.e., salt alternative, salty taste enhancer, or salty taste inhibitor. Moreover, if a cell that expresses the receptor on the cell surface is used, a convenient screening system for salt alternative, salty taste enhancer, or salty taste inhibitor can be provided.

Furthermore, a foodstuff containing a salt alternative substance or a salty taste enhancing substance is effective for suppressing excessive intake of salt, and thus prevention of hypertension or circulatory system diseases.

EMBODIMENTS FOR CARRYING OUT THE INVENTION

Figure 1:
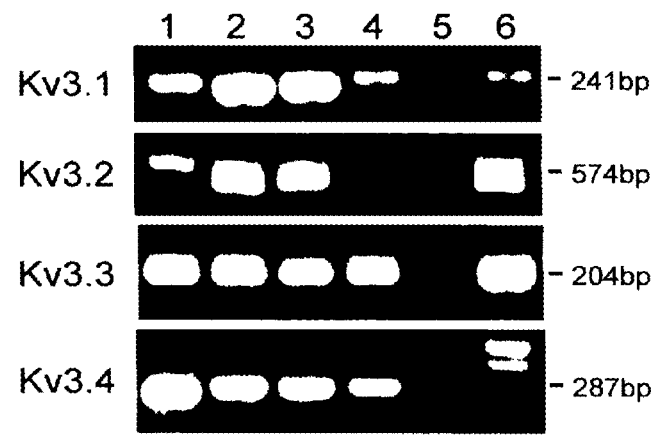
FIG. 1 shows results of RT-PCR indicating expressions of the Kv3.1, Kv3.2, Kv3.3 and Kv3.4 genes in various mouse tissues (electrophoresis photograph): Lane 1: tip of tongue (including fungiform papillae), Lane 2: vallate papillae region, Lane 3: both side portions of tongue (including foliate papillae), Lane 4: tongue epithelium not including taste buds, Lane 5: without reverse transcriptase, Lane 6: kidney.

Hereafter, the present invention will be explained in detail.
The inventors of the present invention confirmed expression of genes encoding the ion channels Kv3.1, Kv3.2, Kv3.3 and Kv3.4 belonging to the Kv3 family (Rudy et al., Trends in Neuroscience, 24:517-526 (2001)) in a mouse tongue epithelial tissue containing taste buds, which ion channels are potassium channels originally considered to function in a nerve cell that shows stimulation at high frequency, and shows current when cell membrane potential is depolarized to −20 mV or higher, and found that expression of a human Kv 3.2 gene in a *Xenopus laevis* oocyte could be involved in the salty taste perception in the form of change of cell membrane current according to change of extracellular sodium ion concentration. On the basis of this finding, they found that Kv3.2 functioned as a salty taste receptor ion channel, and could be used for screening a novel salty taste modulating substance. Moreover, they confirmed that a Kv3.2 gene is expressed in the taste buds, found that, in two kinds of mice of which salty taste response sensitivities were different, there was difference of expression level of the Kv3.2 gene according to the sensitivity, and further confirmed that Kv3.2 is a salty taste receptor. Moreover, the inventors of the present invention newly found splice variants of the Kv3.2 protein in the taste buds.

The method of the present invention comprises the step of contacting a test substance with a cell that expresses a Kv3.2 protein, and comparing observed cation influx into the cell with cation influx into the cell observed when the test substance is not contacted with the cell.

The Kv3.2 protein constitutes a potassium channel, which is a member of the Kv3 family, and it was found by the inventors of the present invention for the first time that the Kv3.2 protein has a cation channel activity, which changes according to change of extracellular sodium ion concentration. The Kv3.2 protein is a polypeptide encoded by the Kcnc2 gene (also written as KCNC2).

In the present invention, examples of the Kv3.2 protein include a protein having the amino acid sequence of SEQ ID NO: 2, 4, 6, 8, 10, 12, 14, 16, 18, 40, 47, 49, 51 or 53.

As polynucleotides encoding human Kv3.2 proteins, four kinds of nucleotide sequences are registered at gene databases (National Center for Biotechnology Information, or Ensembl project, NM_139136, NM_139137, NM_153748, AY243473). The nucleotide sequences of SEQ ID NOS: 1, 3, 5 and 7 correspond to the above nucleotide sequences. The amino acid sequences encoded by the nucleotide sequences are shown in SEQ ID NOS: 2, 4, 6 and 8. These amino acid sequences have a common sequence except for the C terminal region (portion corresponding to the positions 1 to 538 in SEQ ID NO: 2), and they are considered to be splice variants.

Moreover, in a similar database, one kind of polynucleotide encoding a mouse Kv3.2 protein is registered (NM_001025581, SEQ ID NO: 9). The amino acid sequence encoded by the nucleotide sequence of SEQ ID NO: 9 is shown in SEQ ID NO: 10. Moreover, four kinds of nucleotide sequences are registered as polynucleotides encoding rat Kv3.2 proteins (NM_139216, NM_139217, ENSRNOT00000049943, X62839). These nucleotide sequences are shown in SEQ ID NOS: 11, 13, 15 and 17. The amino acid sequences encoded by these nucleotide sequences are shown in SEQ ID NOS: 12, 14, 16 and 18. These amino acid sequences also have a common sequence except for the C terminal region (portion corresponding to the positions 1 to 593 in SEQ ID NO: 12), and they are considered to be splice variants.

Moreover, as shown in the Examples described later, a Kv3.2 protein gene of *Xenopus laevis* was isolated, and it was demonstrated that this protein had a cation channel activity which changed according to change of extracellular sodium ion concentration. The nucleotide sequence of this gene is shown in SEQ ID NO: 39, and the amino acid sequence of the Kv3.2 protein encoded by this gene is shown in SEQ ID NO: 40.

Furthermore, as shown in the Examples described later, four kinds of splice variants of mouse Kv3.2 gene were isolated from a mouse tongue epithelial tissue containing the taste buds. The nucleotide sequences of these splice variants are shown in SEQ ID NOS: 46, 48, 50 and 52. The amino acid sequences encoded by these nucleotide sequences are shown in SEQ ID NOS: 47, 49, 51 and 53, respectively. The amino acid sequences of SEQ ID NOS: 10, 47, 49, 51 and 53 have a common sequence except for the C terminus regions (portion corresponding to the positions 1 to 597 in SEQ ID NO: 10).

The Kv3.2 protein used for the method of the present invention includes interspecific homologues, and it may be, for example, a Kv3.2 protein derived from dog, horse, chimpanzee, fowl, opossum, swine or bovine, in addition to proteins having the sequences derived from human, mouse, rat and *Xenopus laevis* as described above. The sequence information of the genes encoding these proteins are registered with the following numbers, respectively: dog: XM_538289, horse: XM_001488185, chimpanzee: XR_020952, fowl: XM_001235254, opossum: XM_001363374, XM_001363455, swine: XM_001926426, XM_001924780, and bovine: XM_590276. Moreover, as for rhesus monkey, anole lizard, marmoset, guinea pig, sloth, armadillo, kangaroo rat, *Echinops telfairi*, hedgehog, three-spined stickleback, gorilla, elephant, wallaby, lemur, microbat, pika, rabbit, galago, orangutan, hyrax, fruit bat, shrew, squirrel, zebra finch, *Takifugu oblongus*, tarsier, tree shrew and dolphin, the sequence information on the genes encoding the Kv3.2 protein of them are registered with the following numbers, respectively: rhesus monkey: ENSMMUG00000012362, anole lizard: ENSACAG00000007691, marmoset: ENSCJAG00000001261, guinea pig: ENSCPOG00000003474, sloth: ENSCHOG00000007167, armadillo: ENSDNOG00000013383, kangaroo rat: ENSDORG00000000056, *Echinops telfairi*: ENSETEG00000010484, hedgehog: ENSEEUG00000002220, three-spined stickleback: ENSGACG00000019441, gorilla: ENSGGOG00000003896, elephant: ENSLAFG00000031982, wallaby: ENSMEUG00000007789, lemur: ENSMICG00000017734, microbat: ENSMLUG00000010813, pika: ENSOPRG00000017272, rabbit: ENSOCUG00000004467, galago: ENSOGAG00000000768, orangutan: ENSPPYG00000004780, hyrax: ENSPCAG00000015808, fruit bat: ENSPVAG00000010964, shrew: ENSSARG00000006415, squirrel: ENSSTOG00000004842, zebra finch: ENSTGUG00000007354, *Takifugu oblongus*: ENSTRUG00000003532, tarsier: ENSTSYG00000010689, tree shrew: ENSTBEG00000001105, and dolphin: ENSTTRG00000013226.

The gene encoding Kv3.2 is not limited to a gene having the aforementioned gene information or a gene having a known sequence, a gene having a conservative mutation, such as a homologue or an artificially modified version of such a gene as described above can also be used, so long as the Kv3.2 protein encoded by the chosen gene can constitute a cation channel of which activity changes according to change of extracellular sodium ion concentration. That is, it may be a gene encoding a protein having an amino acid sequence of a known protein including substitutions, deletions, insertions, and/or additions of one or more amino acid residues at one or more positions, or the like. The expression that the Kv3.2 protein "can constitute a cation channel of which activity changes according to change of extracellular sodium ion concentration" means that it has an activity of increasing cell membrane potential induced by influx of cations into the cell when the cell expressing the protein is contacted with sodium ions. Examples of the cation include sodium ion, calcium ion, magnesium ion, lithium ion, ammonium ion, and so forth, and sodium ion is preferred.

Although the number of the "one or more" amino acid residues referred to herein may differ depending on the position in the three-dimensional structure of the protein or the types of amino acid residues, specifically, it may be preferably 1 to 20, more preferably 1 to 10, still more preferably 1 to 5, particularly preferably 1 to 3. A typical example of the conservative mutation is conservative substitution. The conservative substitution is a mutation wherein substitution takes place mutually among Phe, Trp, and Tyr, if the substitution site is an aromatic amino acid; among Leu, Ile and Val, if it is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Substitutions considered conservative substitutions include, specifically, substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. The aforementioned amino acid substitutions, deletions, insertions, additions, inversions or the like may be a result of a naturally-occurring mutation or a variation due to an individual difference or difference of species of a microorganism from which the genes are derived (mutant or variant). Such genes can be obtained by, for example, modifying a known nucleotide sequence of a gene by site-specific mutagenesis so that the amino acid residues at the specific sites of the encoded protein include substitutions, deletions, insertions, or additions of amino acid residues.

Furthermore, such genes having a conservative mutations as described above may be a gene encoding a protein having a homology of 78% or more, preferably 80% or more, more preferably 90% or more, still more preferably 95% or more, further preferably 97% or more, particularly preferably 99% or more, to the entire encoded amino acid sequence and having a function equivalent to that of the wild-type Kv3.2 protein. In this specification, the term "homology" may mean "identity".

Moreover, codons in the gene sequences may be replaced with other codons which are easily used in the host into which the genes are introduced.

The gene having a conservative mutation may be a gene obtained by a method usually used for mutation treatment, such as treatment with a mutagen. Furthermore, the Kv3.2 gene may contain one or more introns, so long as the Kv3.2 protein can be expressed when the gene is introduced into a host cell.

Examples of the DNA encoding Kv3.2 (henceforth also referred to as "Kv3.2 gene") include a polynucleotide that is able to hybridize with a nucleotide sequence complementary to a known gene sequence, or a probe which can be prepared from the complementary sequence under stringent conditions, and codes for a protein having a function equivalent to that of a known Kv3.2 protein.

The "stringent conditions" are conditions under which a so-called specific hybrid is formed, and a non-specific hybrid is not formed. Although it is difficult to definitely define the conditions with numerals, examples of the stringent conditions include those under which highly homologous polynucleotides hybridize to each other, for example, polynucleotides not less than 78% homologous, preferably not less than 80% homologous, more preferably not less than 90% homologous, still more preferably not less than 95% homologous, particularly preferably not less than 97% homologous, hybridize to each other, and polynucleotides less homologous than the above do not hybridize to each other, or conditions of washing once, preferably 2 or 3 times, at a salt concentration and temperature corresponding to washing of typical Southern hybridization, i.e., 1×SSC, 0.1% SDS at 60° C., preferably 0.1×SSC, 0.1% SDS at 60° C., more preferably 0.1× SSC, 0.1% SDS at 68° C.

As the probe, a part of the sequence which is complementary to the gene can also be used. Such a probe can be prepared by PCR using oligonucleotides prepared on the basis of a known gene sequence as primers and a DNA fragment containing the nucleotide sequence as a template. For example, when a DNA fragment having a length of about 300 bp is used as the probe, the washing conditions of hybridization may be 50° C., 2×SSC and 0.1% SDS.

When various Kv3 family proteins were compared for homology, the Kv3.2 protein homologues of the aforementioned various animals showed a homology (identity) of 78% or more, but when the Kv3.2 protein and other Kv3 family proteins were compared, the highest homology was 74%.

A Kv3.2 gene can be obtained by designing appropriate primers or probe on the basis of information on nucleotide sequence of a known Kv3.2 gene or a novel Kv3.2 gene disclosed in this specification, such as a polynucleotide encoding a polypeptide having the amino acid sequence shown in SEQ ID NO: 2, 4, 6, 8, 10, 12, 14, 16, 18, 40, 47, 49, 51 or 53, and performing polymerase chain reaction (PCR), Southern hybridization, or Northern hybridization by using the primers or probe and a sample (for example, total RNA, mRNA fraction, cDNA library) derived from an objective organism, for example, a mammal (e.g., human, mouse, rat, dog, horse, chimpanzee, rhesus monkey, fowl, opossum, swine, bovine, etc.).

The Kv3.2 gene may be a fragment or may be a gene encoding a chimera protein of the Kv3.2 protein or a fragment thereof and other protein, so long as the gene codes for a protein that can constitute a cation channel of which activity changes according to change of extracellular sodium ion concentration.

For example, there are splice variants of the Kv3.2 protein as described above, and it is highly possible that the regions on the C-terminal side of the common portions (for example, the positions 1 to 538 of SEQ ID NO: 2) may be deleted or replaced with another sequence.

By introducing a polynucleotide encoding a Kv3.2 protein into an appropriate host cell in an expressible form, and allowing expression of the Kv3.2 protein, a cell having a salty taste receptor ion channel can be obtained. For example, by introducing a linear DNA encoding a Kv3.2 protein or a vector containing a sequence encoding a Kv3.2 protein into a host cell, a Kv3.2 protein can be expressed. Examples of the sequence in an expressible form include a sequence prepared on the basis of the DNA information and comprising a sequence encoding a Kv3.2 protein and sequences required for transcription and translation upstream of the sequence encoding a Kv3.2 protein, so that the Kv3.2 protein can be produced. Furthermore, by injecting a cRNA encoding a Kv3.2 protein into a host cell, a cell having a salty taste receptor ion channel can also be obtained. In this case, the cRNA contains a sequence required for translation on the 5' end side of the cRNA. Examples of the sequence required for transcription include expression control sequences such as promoter and enhancer. Furthermore, it may contain a transcription terminator sequence. Examples of the sequence required for translation include a ribosome-binding site. Furthermore, it may contain, for example, a processing information site, such as RNA splice site, a polyadenylation site, and so forth, as required. Examples of the promoter include promoters derived from immunoglobulin gene, SV40, adenovirus, bovine papilloma virus, cytomegalovirus, and so forth.

As the cell into which the polynucleotide encoding a Kv3.2 protein is introduced, an animal cell, an insect cell, or yeast are preferred, and an animal cell is particularly preferred. For example, a fraction in which taste cells are concentrated, an isolated taste cell, a tissue isolated from a tissue selected from tongue epithelium, adrenal gland, pineal body, thyroid, melanocyte, and kidney, and so forth may be used. Specific examples of cell, which is considered to enable temporary functional expression, when a recombinant vector that expresses a polynucleotide encoding a Kv3.2 protein is introduced, include *Xenopus laevis* oocyte, Chinese hamster ovary cell (CHO), human embryonic kidney (HEK) cell, Sf-9 insect cell, and so forth. The present invention provides a cell introduced with such a polynucleotide encoding a Kv3.2 protein in an expressible form. As the cell, an oocyte or a taste cell is preferred, and a taste cell is especially preferred for use in screening a salty taste modulating substance.

As the method for introducing a polynucleotide encoding a Kv3.2 protein into such cells, a known method can be used. Techniques required for the operations such as introduction of a polynucleotide into a cell are described in Sambrook, J., Fritsch, E. F. and Maniatis, T., "Molecular Cloning A Laboratory Manual and Second Edition", Cold Spring Harbor Laboratory Press (1989), etc.

As shown in the Examples, a cell that expresses the Kv3.2 protein has a cation channel activity which changes according to change of extracellular sodium ion concentration. Therefore, the Kv3.2 protein expressed in a cell can constitute a cation channel of which activity changes according to change of extracellular sodium ion concentration. Although it is presumed that the Kv3.2 protein constitutes a cation channel of which activity changes according to change of extracellular sodium ion concentration as a multimer, the Kv3.2 protein may be monomer or multimer, so long as the cell that expresses the Kv3.2 protein has the cation channel activity which changes according to change of extracellular sodium ion concentration. The "cation channel" means a channel that allows flow of cations such as sodium ion, calcium ion, and potassium ion into or out of cells.

Furthermore, as shown in the Examples, the gene encoding the Kv3.2 protein is expressed in the taste buds of the tongue, which are taste receptors, and since the expression level thereof is higher in a mouse strain showing higher salty taste perception sensitivity as compared with a mouse strain showing lower salty taste perception sensitivity, it is supported that the Kv3.2 protein is a salty taste receptor protein that controls salty taste perception sensitivity.

Therefore, by identifying a compound that acts on a Kv3.2 protein or a cell expressing it, a salty taste modulating substance can be searched for.

Identification of such a compound can be attained by, in addition to the aforementioned methods, for example, measuring binding between a purified Kv3.2 protein and a test substance. In addition, a compound that acts on the Kv3.2 protein can be efficiently searched by estimating stereostructure thereof with a computer with reference to stereostructure information on related proteins (for example, Kv1.2, Chen et al., Proc. Natl. Acad. Sci. USA, 107:11352-11357 (2010)), and choosing a compound showing affinity to a site that may affect the ion channel activity with a computer.

By contacting a test substance with a cell expressing a Kv3.2 protein obtained as described above, and comparing observed cation influx into the cell with cation influx into the cell observed when the test substance is not contacted with the cell, a salty taste modulating substance can be screened for.

If the cation influx observed when a test substance is contacted with a cell that expresses the Kv3.2 protein is larger than cation influx into the cell observed when the test substance is not contacted with the cell, it is judged that the test substance activates the salty taste receptor channel, and if the cation influx observed when a test substance is contacted with a cell that expresses the Kv3.2 protein is smaller than cation influx into the cell observed when the test substance is not contacted with the cell, it is judged that the test substance inactivates the salty taste receptor channel.

Furthermore, by identifying a gene showing an expression profile similar to that of the Kv3.2 gene or a gene of which expression is suppressed in a Kv3.2 gene-expressing cell among genes expressed in the Kv3.2 gene-expressing cell, a protein having a function of positively or negatively regulating the Kv3.2 activity or a protein constituting a salty taste receptor can also be searched for.

The Kv3.2 activity means a function of the Kv3.2 protein for constituting a cation channel which changes in a cell that expresses it according to change of extracellular sodium ion concentration. Moreover, the Kv3.2 activity is also an activity of the Kv3.2 protein as a salty taste receptor protein.

The gene showing an expression profile similar to that of the Kv3.2 gene refers to a gene of which tissue specificity of gene expression is similar to tissue specificity of Kv3.2 gene expression. As one of the methods for identifying a gene showing a similar expression profile, a comprehensive gene expression analysis method such as a DNA microarray method can be exemplified. Specifically, such a gene can be identified by extracting RNAs from various tissues and searching them for a gene showing tissue specificity for gene expression similar to that of the Kv3.2 gene using a comprehensive gene expression analysis method such as a DNA microarray method.

The gene of which expression is suppressed in a Kv3.2 gene-expressing cell refers to a gene of which expression is suppressed in a cell in which Kv3.2 gene is expressed, and of which expression can be confirmed in a cell in which Kv3.2 gene is not expressed. As one of the methods for identifying such a gene of which expression is suppressed, a comprehensive gene expression analysis method such as a DNA microarray method can be exemplified. Specifically, such a gene can be identified by extracting RNAs from various tissues and searching them for a gene of which expression is not observed in a Kv3.2 gene-expressing tissue using a comprehensive gene expression analysis method such as a DNA microarray method.

Such a gene as identified as described above is a gene encoding a protein having a function of controlling the Kv3.2 activity or a protein that constitutes a salty taste receptor, and it is estimated that such a protein constitutes a channel or complex together with the Kv3.2 protein, and is involved in taste perception.

Furthermore, by identifying a compound that acts on a channel or complex constituted by the Kv3.2 protein as a taste receptor and a protein specifically expressed in a taste cell, a taste substance or a flavor substance can also be searched for. The flavor substance is a substance that modifies tastes, and it can be used for foodstuffs as a flavor additive. As the taste substance or flavor substance, specifically, a salty taste modulating substance can be exemplified.

It is known that a substance that activates a taste receptor promotes excitation of a taste receptor cell, and thereby shows a taste or enhances a taste. Therefore, by using a cell in which a salty taste receptor channel is expressed on the cell membrane, a substance that activates or inactivates a salty taste receptor channel, i.e., a salty taste modulating substance, can be screened for. That is, a substance that activates a salty taste receptor channel can be expected to promote excitation of a salty taste receptor cell in which a salty taste receptor ion channel is originally expressed and thereby enhance salty taste perception. Therefore, a substance that activates a salty taste receptor channel in the absence of sodium ion is useful as a candidate substance of a salt alternative substance, and a substance that activates a salty taste receptor channel in the presence of sodium ions is useful as a candidate substance of a salty taste enhancing substance. Therefore, a cell that expresses the Kv3.2 protein itself can be used for screening for a salt alternative or salty taste enhancing substance. Moreover, a substance that inactivates a salty taste receptor channel is useful as a candidate of a salty taste inhibiting substance.

Cation influx into a cell that expresses the Kv3.2 protein can be measured by suspending the cell in a solution containing cations, and directly or indirectly measuring amount of cations flowing into the cell.

Cation influx into a cell can be measured by, for example, measuring electrophysiological characteristics of the cell, for example, cell current, in the presence of extracellular cations. For example, by contacting a cell expressing the Kv3.2 protein with a test substance in the presence of sodium ions, and detecting change in cell membrane potential or membrane current, or intracellular cation concentration, a salty taste modulating substance such as a salty taste enhancing substance or a salty taste inhibiting substance can be screened for. Moreover, by contacting a cell expressing the Kv3.2 protein with a test substance in the absence of sodium ion, and detecting change in cell membrane potential or membrane current, or intracellular cation concentration, a salt alternative substance can be screened for.

Specific methods for screening for a salty taste modulating substance using a cell expressing the Kv3.2 protein are exemplified below.

(1) A *Xenopus laevis* oocyte is allowed to express cRNA encoding the Kv3.2 protein, and a ligand that acts on a salty taste receptor ion channel is searched for on the basis of increase or decrease of the salty taste receptor ion channel current according to the two electrode voltage clamp method. For example, if inward current increases when a test compound is added to an extracellular fluid of a cell of which membrane voltage is clamped at a holding potential of −60 to 80 mV, as compared with the case where the test compound is not added, it can be judged that the test compound is a substance that activates the polypeptide of the present invention. Alternatively, the extracellular sodium ion concentration may be changed stepwise or continuously, and inward current may be measured.

(2) With a cell where a salty taste receptor ion channel is expressed on the cell surface, a ligand that acts on a salty taste receptor ion channel is searched for on the basis of increase or decrease of the salty taste receptor ion channel current with a membrane potential clamped according to the voltage clamp method, especially the whole cell membrane voltage clamp method. For example, if inward current increases when a test compound is added to an extracellular fluid of a cell of which membrane voltage is clamped at a holding potential of −80 mV in the presence of sodium ions, as compared with the case where the test compound is not added, it can be judged that the test compound is a substance that activates the polypeptide of the present invention, i.e., a salty taste enhancing substance.

(3) A cell where a salty taste receptor ion channel is expressed on the cell surface is allowed to incorporate a membrane potential sensitive dye beforehand, then change of fluorescence intensity of the dye in the cell is analyzed (namely, measured or detected) when a test compound is added in the presence of sodium ions, and thereby whether the Kv3.2 protein is activated or not is analyzed. This method uses a property of the membrane potential sensitive dye that it enables optical detection of change of the membrane potential in connection with the opening of the ion channel. More specifically, as the membrane potential sensitive dye, DiBAC [bis-(1,3-dibutylbarbituric acid) trimethineoxonol, Molecular Probes] or a derivative thereof, Membrane Potential Assay Kit (Molecular Devices) etc. can be used.

(4) A cell where a salty taste receptor ion channel is expressed on the cell surface is allowed to incorporate a cation sensitive dye (for example, SBFI, CoroNa Green, Sodium Green (Molecular Probes), etc.) beforehand, and a salty taste enhancing or inhibiting substance is searched for on the basis of change of fluorescence intensity ratio (intracellular cation concentration) at the time of contacting a ligand candidate compound and a salty taste receptor ion channel expressing cell for a certain period in the presence of sodium ions.

(5) By performing the methods of (2) to (4) described above in the absence of sodium ion, a salt alternative substance can be searched for.

EXAMPLES

Hereafter, the present invention will be specifically explained with reference to examples. However, the examples do not limit the scope of the present invention. Unless otherwise indicated, the procedures of the examples were carried out by known methods (Maniatis, T. et al., "Molecular Cloning—A Laboratory Manual", Cold Spring Harbor Laboratory, NY, 1-982; and Hille, B., Ionic Channels of Excitable Membranes, 2nd Ed., Sinauer Associates Inc., MA, 1992).

Example 1

Expression Analysis of Mouse Kv3 Family Channel Genes

Expression distribution of the Kv3 family channel gene encoding a protein having the amino acid sequence shown in SEQ ID NO: 10 in the tongue epithelium was analyzed by RT-PCR according to the following procedures using a mouse tongue epithelial tissue.

The epithelium was isolated from the tongue of mouse, and a tongue tip portion containing fungiform papillae, a region containing vallate papillae (center rear portion of the tongue), both side portions of the tongue containing foliate papillae, and the epithelium not containing taste buds were further excised, respectively. Separately, the kidney was excised and pulverized.

RNA was extracted from each tissue using an RNA extraction kit (Absolutely RNA Microprep Kit, Stratagene). The extracted RNA was reverse transcribed using SuperScript III First Strand Synthesis System for RT-PCR (Invitrogen) to synthesize a first strand cDNA. By using the obtained first strand cDNA as a template, PCR was performed with the combinations of primers shown in Table 1 to amplify cDNAs of the genes of the Kv3.1, Kv3.2, Kv3.3, and Kv3.4 proteins.

TABLE 1

| Gene | Forward primer SEQ ID NO: | Reverse primer SEQ ID NO: |
| --- | --- | --- |
| Kv3.1 | 21 | 22 |
| Kv3.2 | 23 | 24 |
| Kv3.3 | 25 | 26 |
| Kv3.4 | 27 | 28 |

PCR was performed by the hot start method using FastStart Taq DNA polymerase (Roche Applied Science). The nucleotide sequences of the aforementioned primers are specific to a mouse Kv3.1 gene (NM_001112739), mouse Kv3.2 gene (NM_001025581, SEQ ID NO: 9), mouse Kv3.3 gene (NM_008422) and mouse Kv3.4 gene (NM_145922), and allow amplification of the DNA fragments of Kv3.1 (241 bp), Kv3.2 (574 bp), Kv3.3 (204 bp), and Kv3.4 (287 bp), respectively. The GenBank accession numbers are indicated in the parentheses following the gene names.

RT-PCR analysis was performed for mRNAs derived from the tongue tip portion containing fungiform papillae, the region containing vallate papillae (center rear portion of the tongue), the both side portions of the tongue containing foliate papillae, and the epithelium not containing taste buds, and mRNA derived from the kidney. As controls, the same reaction was performed without adding a reverse transcriptase for mRNAs derived from those tissues.

As a result, in the tongue tip portion containing fungiform papillae, the region containing vallate papillae, and the both side portions of the tongue containing foliate papillae, which were epithelial tissues including the taste buds, DNA fragments of expected sizes were amplified for all the proteins, Kv3.1, Kv3.2, Kv3.3 and Kv3.4 (FIG. 1). These results revealed that expression of mRNAs of the ion channel proteins of the Kv3 family was observed in portions containing the taste buds in the tongue epithelium. In particular, it was clarified that the Kv3.2 gene localized only in portions containing taste buds, i.e., the tongue tip portion containing fungiform papillae, the region containing vallate papillae, and the both side portions of the tongue containing foliate papillae, in the tongue epithelium. At the same time, DNA fragments of expected sizes were also amplified for Kv3.1, Kv3.2 and Kv3.3 for the kidney. As for Kv3.4, a DNA fragment of a size different from the expected size was amplified, and there was suggested a possibility of the existence of a splice variant.

Example 2

Isolation of Polynucleotide Encoding Human Kv3.2 Protein and Construction of Expression Vector Therefor Although the full length cDNA encoding a human salty taste receptor protein can be cloned from, for example, human mRNA, it can also be purchased as a corresponding full length cDNA among those included in The Mammalian Gene Collection (MGC: 120670, IMAGE: 7939480, catalog number: MHS1010-98052225, Open Biosystems). By using this commercially available plasmid as a template, an oligonucleotide consisting of the nucleotide sequence shown in SEQ ID NO: 19 (KpnI recognition sequence was added to the 5' end)

as a forward primer, and an oligonucleotide consisting of the nucleotide sequence shown in SEQ ID NO: 20 (XhoI recognition sequence was added to the 5' end) as a reverse primer, PCR was performed. The obtained DNA fragment was digested with the restriction enzymes KpnI and XhoI, and then cloned into the plasmid pcDNA3.1(+). The obtained clone was designated pcDNA3.1-KCNC2. The plasmid pcDNA3.1(+) has a promoter sequence derived from cytomegalovirus, and can be used for expression of a polypeptide encoded by a cloning fragment in an animal cell.

The nucleotide sequence of the obtained clone pcDNA3.1-KCNC2 was analyzed using a DNA sequencer (3130 xl Genetic Analyzer, Applied Biosystems) according to the dideoxy terminator method, and the nucleotide sequence shown in SEQ ID NO: 5 was obtained. The nucleotide sequence shown in SEQ ID NO: 5 has an open reading frame consisting of 1677 base pairs. The amino acid sequence predicted from the open reading frame consists of 558 amino acid residues (SEQ ID NO: 6).

Example 3

Expression of Kv3.2 Protein in *Xenopus Laevis* Oocyte

In order to detect the cation channel activity of a protein having the amino acid sequence shown in SEQ ID NO: 5, which activity changes according to the change of extracellular sodium ion concentration, cRNA was synthesized by using the expression vector pcDNA3.1-KCNC2 obtained in Example 2 described above as a template, and injected into a *Xenopus laevis* oocyte, so that the protein was expressed. The aforementioned expression vector pcDNA3.1-KCNC2 was digested with the restriction enzyme XhoI at one site and thereby made linear, and then cRNA encoding the Kv3.2 protein was synthesized by using a commercially available cRNA synthesis kit, Megascript High Yield Transcription Kit (Ambion). The synthesized cRNA was injected into a *Xenopus laevis* oocyte prepared in a conventional manner using a glass capillary and a microinjector (World Precision Instruments), so that the Kv3.2 protein was expressed. Furthermore, as a control cell, an oocyte into which water was injected was also prepared in the same manner. The obtained these oocytes were stored in a standard oocyte culture medium such as the ND96+ solution (96 mM NaCl, 2 mM KCl, 1 mM MgCl$_2$, 1.8 mM CaCl$_2$, 5 mM HEPES, 2 mM sodium pyruvate, 1/100 penicillin/streptomycin mixture (15140-122, Invitrogen), adjusted to pH 7.4 with NaOH) at 18° C. for two to four days, and then used in Examples 4 described below.

Example 4

Detection of Cation Channel Activity of Kv3.2 Protein, which Activity Changes According to Change of Extracellular Sodium Ion Concentration The total cell current was measured for each of the oocytes obtained in Example 3, of which membrane potential was clamped by the two electrode voltage clamp method. For this measurement, the ND96 solution (96 mmol/L NaCl, 2 mmol/L KCl, 1 mmol/L MgCl$_2$, 1.8 mmol/L CaCl$_2$, and 5 mmol/L HEPES (pH 7.5)) was used.

Figure 2:
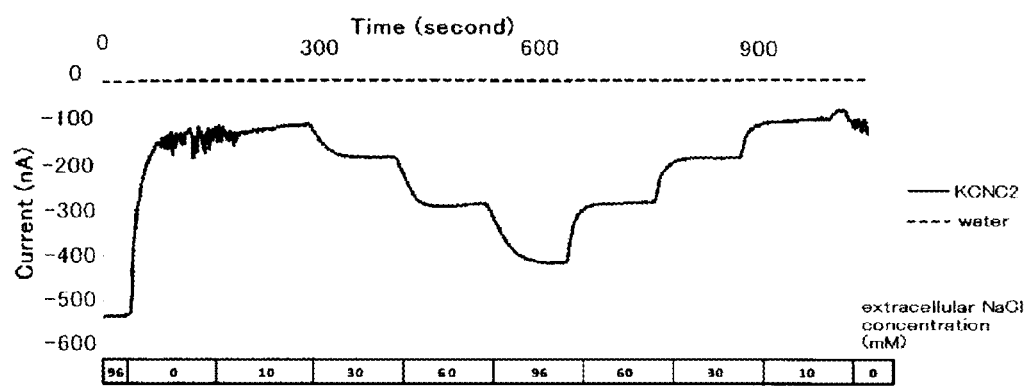
FIG. 2 shows change of cell membrane current observed for *Xenopus laevis* oocyte expressing a Kv3.2 protein (human) when extracellular sodium ion concentration was changed. KCNC2 indicates injection of Kv3.2 cRNA.

In the *Xenopus laevis* oocyte injected with cRNA prepared using the plasmid pcDNA3.1-KCNC2 as the template, an inward current higher than 100 nA was measured at a holding potential of −80 mV, when the NaCl concentration in the extracellular fluid was set to be 96 mM. Increase of this current with increase of the extracellular sodium ion concentration was observed, when the NaCl concentration in the extracellular fluid was changed between 0 to 96 mM by replacing NaCl in the aforementioned ND96 solution with N-methyl-D-glucamine hydrochloride (FIG. 2). On the other hand, in the control oocyte injected with water, such a significant inward current was not observed at a holding potential of −80 mV, when the NaCl concentration in the extracellular fluid was set to be 96 mM, and change of the current was not also observed, even when the sodium ion concentration in the extracellular fluid was changed.

Example 5

Confirmation of Presence or Absence of Cation Channel Activity that Changes According to Change of Extracellular Sodium Ion Concentration for Kv3 Family Proteins Expression vectors were constructed for the channels Kv3.1, Kv3.3 and Kv3.4 belonging to the Kv3 family, like Kv3.2, in the same manner as that of Example 2. Full length cDNAs encoding the corresponding proteins were purchased (Kv3.1: catalog number ORK11519, Promega, Kv3.3: catalog number OHS4559-99848374, Open Biosystems, Kv3.4: catalog number MHS1010-98052650, Open Biosystems). By using each of these full length cDNAs as a template and a combination of the primers shown in Table 2, PCR was performed to prepare gene DNA fragments encoding the proteins of Kv3.1, Kv3.3, and Kv3.4, respectively. Both the 5' and 3' ends of each obtained DNA fragment was digested with restriction enzymes (Kv3.1: XbaI and XhoI, Kv3.3: NheI and EcoRI, Kv3.4: NheI and XhoI), then the digestion product was cloned into the plasmid pcDNA3.1(+). The obtained clones were designated pcDNA3.1-KCNC1 (Kv3.1), pcDNA3.1-KCNC3 (Kv3.3) and pcDNA3.1-KCNC4 (Kv3.4), respectively.

TABLE 2

| Gene | Forward primer SEQ ID NO: | Reverse primer SEQ ID NO: |
| --- | --- | --- |
| Kv3.1 | 29 | 30 |
| Kv3.3 | 31 | 32 |
| Kv3.4 | 33 | 34 | cRNAs were synthesized using these plasmids as templates, and injected into *Xenopus laevis* oocytes in the same manner as that of Example 2, so that the proteins were expressed. The aforementioned expression vectors pcDNA3.1-KCNC1, pcDNA3.1-KCNC3 and pcDNA3.1-KCNC4 were digested with a restriction enzyme (Kv3.1: XhoI, Kv3.3: EcoRI, Kv3.4: XhoI) at one site and thereby made linear, and then cRNAs encoding the Kv3.1, Kv3.3 and Kv3.4 proteins were synthesized respectively using a commercially available cRNA synthesis kit, Megascript High Yield Transcription Kit (Ambion). The synthesized cRNAs were each injected into *Xenopus laevis* oocytes prepared in a conventional manner by using a glass capillary and a microinjector (World Precision Instruments), so that the proteins encoded by the cRNAs were expressed. As control cells, an oocyte injected with Kv3.2 in the same manner as that of Example 2 so that the protein was expressed, and an oocyte into which water was injected were also prepared. The obtained oocytes were stored in a standard oocyte culture medium such as the ND96+ solution (96 mM NaCl, 2 mM KCl, 1 mM MgCl$_2$, 1.8 mM CaCl$_2$, 5 mM HEPES, 2 mM sodium pyruvate, 1/100 penicillin/streptomycin mixture (15140-122, Invitrogen), adjusted to pH 7.4 with NaOH) at 18° C. for two to four days, and then the total cell current was measured for each of the oocytes, of which membrane potential was clamped by the dual electrode voltage clamp method. For this measurement, the ND96 solution (96 mmol/L NaCl, 2 mmol/L KCl, 1 mmol/L MgCl$_2$, 1.8 mmol/L CaCl$_2$, and 5 mmol/L HEPES (pH 7.5)) was used.

Figure 3:
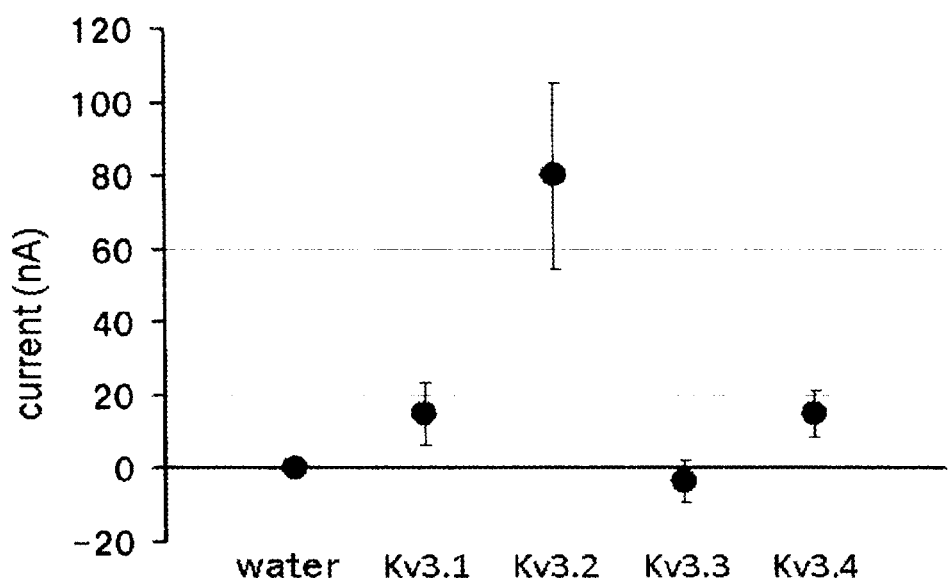
FIG. 3 shows difference of cell membrane current observed for *Xenopus laevis* oocyte expressing a Kv3.2 protein (human) when extracellular sodium ion concentration was changed from 0 mM to 96 mM.

For the case where the NaCl concentration in the extracellular fluid was set to be 96 mM using ND960, and the case where the NaCl concentration in the extracellular fluid was set to be 0 mM by substitution of N-methyl-D-glucamine hydrochloride for NaCl in the ND96 solution, the difference of current amounts at a holding potential of −80 mV was measured for each oocyte. As a result, only when the cRNA encoding the Kv3.2 protein was injected, a current amount difference of about 80 nA or larger in average was measured (FIG. 3). On the other hand, such current amount difference could not be observed for the control oocyte injected with water. For the oocytes injected with each of cRNAs encoding Kv3.1, Kv3.3 and Kv3.4 proteins, which are the other channels of the Kv3 family, only a current smaller than 15 nA was measured, and significant difference was not observed with respect to the control oocyte injected with water. On the basis of these measurement results, it was confirmed that, among the quite similar Kv3 family channels, only the Kv3.2 showed increase in the current amount in connection with the increase of the extracellular sodium ion concentration.

The above results revealed that the Kv3.2 protein could constitute a cation channel of which activity changes according to change of extracellular sodium ion concentration.

Example 6

Comparison of Expression Levels of Kv3.2 Gene In Strains Showing Difference in Salty Taste Perception Sensitivity A method for measuring mouse salty threshold value by using behavioral procedures has been reported (Ishiwatari, Y. and Bachmanov, A. A., Chemical Senses, 34:277-293 (2009)). Moreover, it has also been reported that there is difference in salty taste perception sensitivity among mouse strains (Ishiwatari, Y., and Bachmanov, A. A., Chemical Senses, 32:A26 (2007)). By using the aforementioned behavioral method, difference of salty threshold values was measured for two strains showing difference in salty taste perception sensitivity, C57BL/6J (strain showing high salty taste perception sensitivity), and A/J (strain showing low salty taste perception sensitivity). As a result, it was confirmed that there was difference in the threshold value of about 5 times between the both (Table 3). Then, expression amount of the gene encoding the Kv3.2 protein in the tongue epithelium of both the strains were quantified and compared.

TABLE 3

| Strain | Salty threshold value (mM) |
|---|---|
| C57BL/6J | 8.6 |
| A/J | 43.3 |

The epithelia were isolated from the tongues of mice of the two strains (C57BL/6J, A/J), and a tongue tip portion containing the fungiform papillae and epithelium not containing taste buds were excised, respectively, from each of them. RNA was extracted from each tissue using an RNA extraction kit (Absolutely RNA Microprep Kit, Stratagene). The extracted RNA was reverse-transcribed using SuperScript III First Strand Synthesis System for RT-PCR (Invitrogen) to synthesize a first strand cDNA. By using the obtained first strand cDNA as a template, quantitative RT-PCR analysis was conducted with TaqMan Gene Expression Assays (Life Technologies) and StepOnePlus Real-time PCR System (Life Technologies). The quantification results were corrected by expression amount of β-actin gene (actb) in each site, and then the expression levels of the strains were compared. Two kinds of assays (Probe 1: Mm01234233_m1, Probe 2: Mm01234232_m1) were performed for the Kv3.2 gene, and as a result, difference was observed between expression levels in the tongue tip portions of both the strains, A/J and C57BL/6J. The expression level of the strain C57BL/6J was 3 to 5 times higher than the expression level of the strain A/J, and it is considered that this difference in the expression levels affects the difference of the salty taste perception sensitivity (Table 4). On the other hand, no expression was detected in the epithelia not containing the taste buds of both the strains.

TABLE 4

| | B6/A (actb normalized) * | |
|---|---|---|
| Site | Probe 1 | Probe 2 |
| Tongue tip portion (containing fungiform papillae) | 3.43 | 5.21 |

* Ratio of expression amounts of B6 (C57BL/6J) and A (A/J) standardized with actb gene expression amount On the basis of the above results, it was confirmed that the Kv3.2 gene coded for a protein contributing to salty taste perception.

Example 7

Confirmation of Expression of Mouse Kv3.2 Gene In Taste Buds by In Situ Hybridization Method A cDNA encoding the full length of the mouse salty taste receptor protein can be cloned by designing a primer set with reference to SEQ ID NO: 9 and a similar sequence registered at a gene database (GenBank accession number: BY281762), and performing PCR with it. By using an oligonucleotide consisting of the nucleotide sequence shown in SEQ ID NO: 35 as a forward primer, an oligonucleotide consisting of the nucleotide sequence shown in SEQ ID NO: 36 as a reverse primer, and the first strand cDNA obtained in Example 6, which was prepared from the tongue tip portion containing the fungiform papillae, as a template, PCR was performed. The obtained DNA fragment was cloned in the plasmid pGEM-T Easy (Promega). The obtained clone was designated pGEM-T-mKcnc2. The nucleotide sequence of the obtained clone was analyzed using a DNA sequencer (3130 xl Genetic Analyzer, Applied Biosystems) according to the dideoxy terminator method, and it was confirmed that the same nucleotide sequence as that of SEQ ID NO: 9 was obtained. Furthermore, the plasmid pGEM-T-mKcnc2 was digested with the restriction enzyme SphI at one site and thereby made linear, and an antisense RNA of the mouse Kv3.2 gene labeled with digoxigenin was synthesized by using DIG RNA Labeling Kit (Roche Diagnostics).

Figure 4:
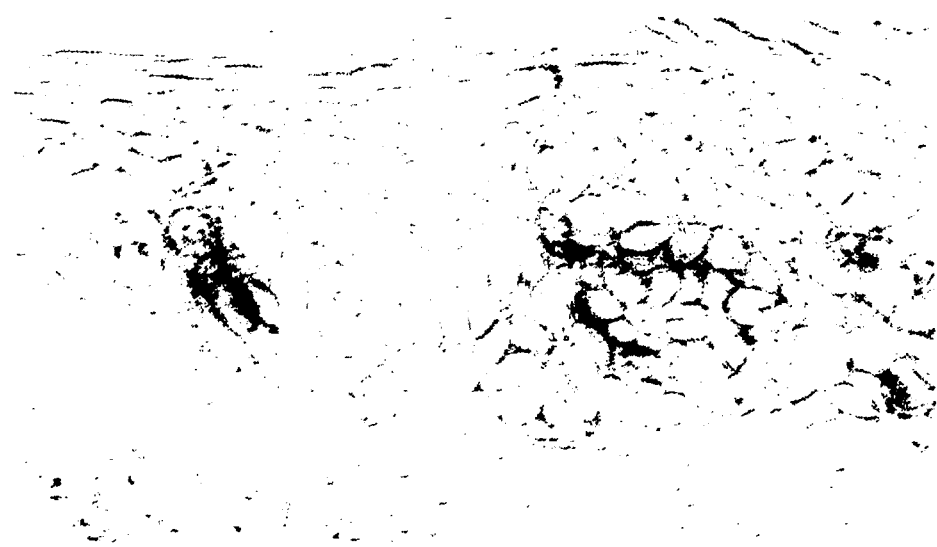
FIG. 4 shows results of in situ hybridization indicating a Kv3.2 gene expression site in mouse tongue epithelium (microphotography).

From a portion of mouse tongue containing taste buds immersed in a frozen tissue embedding agent and cryopreserved at −80° C., sections were prepared using a cryostat. After a fixation treatment (immersion in 4% paraformaldehyde solution for 10 minutes), the sections were subjected to an acylation treatment for 10 minutes, washed 3 times with PBS for 10 minutes, and then immersed in a hybridization buffer (5×SSC, 50% formamide, 1×Denhardt's solution, 1 mg/ml of salmon sperm DNA, 1 mg/ml of tRNA). A cRNA probe was prepared using T7 RNA polymerase in the presence of UTP labeled with digoxigenin. Hybridization was performed at 72° C. in a 5×SSC, 50% formamide solution. For signal detection, a color reaction was performed using an alkaline phosphatase-bound anti-digoxigenin antibody (Roche Diagnostics) and NBT/BCIP as the substrate, and then the sections were observed under a light microscope (BX61, Olympus). As a result of hybridization using the antisense RNA of the mouse Kv3.2 gene labeled with digoxigenin as a probe, signals were detected in the taste buds in a region containing the vallate papillae of the mouse tongue epithelium (FIG. 4). Therefore, it became clear that the Kv3.2 gene was expressed in the taste buds.

From the above results, it was confirmed that the Kv3.2 protein is present in the taste buds. Taking into consideration that the Kv3.2 protein contributes to the salty taste perception sensitivity, and constitutes a cation channel of which activity changes according to change of extracellular sodium ion concentration, it is concluded that the Kv3.2 protein constitutes a salty taste receptor ion channel. The Kv3.2 protein can be used for screening for a novel salty taste modulating substance.

Example 8

Figure 5:
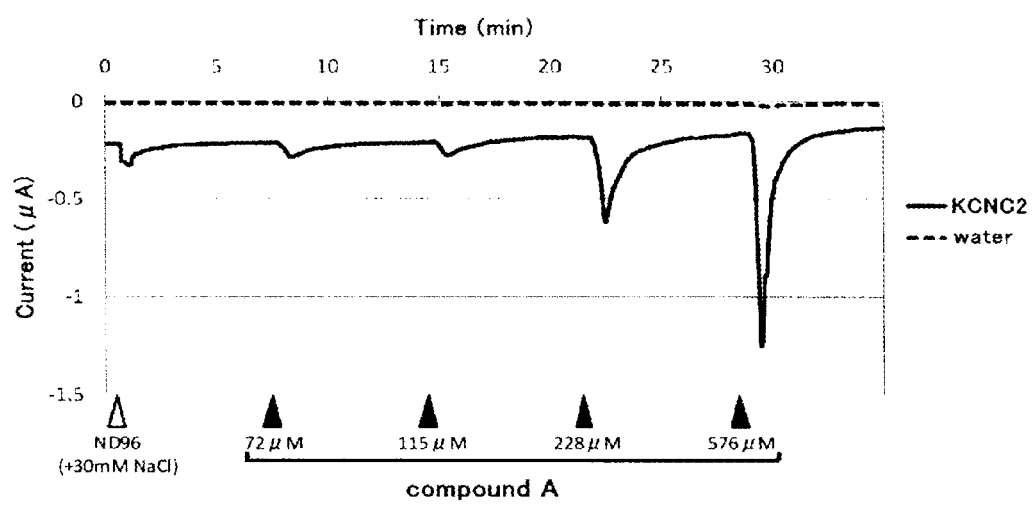
FIG. 5 shows cell membrane current observed for *Xenopus laevis* oocyte expressing a Kv3.2 protein (human), which was contacted with the low molecular organic compound A. KCNC2 indicates injection of Kv3.2 cRNA.

Screening for Channel Activity Modulating Compound Using Kv3.2 cRNA of the human Kv3.2 channel was injected into a matured oocyte taken out from *Xenopus laevis* (female), and the oocyte was stored in a standard oocyte culture medium such as the ND96+ solution (96 mM NaCl, 2 mM KCl, 1 mM $MgCl_2$, 1.8 mM $CaCl_2$, 5 mM HEPES, 2 mM sodium pyruvate, 1/100 penicillin/streptomycin mixture (15140-122, Invitrogen), adjusted to pH 7.4 with NaOH) at 18° C. Two to four days after the injection, the oocyte was set on a parallel clamp system for *Xenopus laevis* oocytes, OpusXpress 6000A (Molecular Devices Japan). The oocyte was perfused with an assay buffer (66 mM N-methyl-D-glucamine hydrochloride, 30 mM NaCl, 2 mM KCl, 1 mM $MgCl_2$, 1.8 mM $CaCl_2$, 5 mM HEPES, adjusted to pH 7.4 with KOH), and the membrane potential was maintained at −80 mV. The cell membrane current was measured in this state, and screening was performed on the basis of detection of change of the current at the time of adding a test substance solution. It is considered that when an inward current is observed for the electric current, the Kv3.2 channel is activated with a compound, and when an outward current is observed, the Kv3.2 channel activity is suppressed. Moreover, in order to distinguish from nonspecific change of electric current due to influence of a test substance on the oocyte itself, the test substance solution was also added to the oocyte injected with water instead of cRNA to confirm that there was no change in the current. For example, a low molecular organic compound A retrieved by the screening increased the current in a concentration dependent manner in the oocyte expressing the human Kv3.2 when the compound was added, but such change of the current was not confirmed in the oocyte injected with water (FIG. 5).

Example 9

Salty Taste Enhancing Effect of Obtained Activity Modulating Compound

Influence on salty taste of the compound for which Kv3.2 channel activity modulating action was found was confirmed by performing a quantitative sensory evaluation test for the compound.

The quantitative sensory evaluation test was performed as follows. The compound A as a sample was mixed in an amount of 0.0001 to 0.002 g/dl with distilled water containing sodium chloride (0.5 g/dl), and intensity of salty taste enhancing activity of the compound was measured. Distilled water containing 0.55 g/dl, 0.60 g/dl or 0.65 g/dl of sodium chloride was used as objects of comparison. A method according to the linear scale method was used, wherein the panelists marked positions corresponding to their grading on a straight line on which positions of sodium chloride concentrations corresponding to 1.0 time (0.50 g/dl), 1.1 times (0.55 g/dl), 1.2 times (0.60 g/dl), and 1.3 times (0.65 g/dl) the concentration of the mixture were indicated. Test scores were obtained by averaging the positions marked by the panelists and indicated as a salty taste enhancing ratio (times). The test was performed with n=6. The panelists consisted of persons who experienced development of flavoring of foodstuffs for one year or more in total, and could distinguish sodium chloride solutions having different concentrations of 0.50 g/dl, 0.55 g/dl and 0.60 g/dl (this ability was periodically confirmed). As the "initial taste", intensity of salty taste within 2 seconds after holding in the mouth was evaluated, and the "middle and after tastes" means the total of middle taste and after taste, and evaluated as intensity of salty taste after 2 seconds from holding in the mouth. The results for typical concentrations are shown in Table 5. As shown by the results, it was found that addition of the compound A enhanced salty taste intensity in a concentration dependent manner.

TABLE 5

| Sample | Concentration (g/dl) | Salty taste enhancing ratio (times) | | Evaluation comment |
| --- | --- | --- | --- | --- |
| | | Initial taste | Middle and after tastes | |
| No additive | — | 1 | 1 | — |
| Compound A | 0.0001 | 1.01 | 1.01 | Almost no effect of addition |
| | 0.001 | 1.04 | 1.04 | Salty taste was slightly enhanced, after taste included bitter taste |
| | 0.002 | 1.05 | 1.07 | Salty taste was enhanced in middle and after tastes, after taste included bitter taste |

Example 10

Cloning of *Xenopus Laevis* Kv3.2 Gene

There has been no information on cDNA encoding the Kv3.2 channel protein of *Xenopus laevis*. However, in the gene database of the closely related species, *Xenopus tropicalis*, a nucleotide sequence predicted to code for Kv3.2

(C_scaffold_541000003) is registered. With reference to this sequence as well as the gene sequence information on the human, mouse and rat Kv3.2 genes, PCR was performed using an oligonucleotide consisting of the nucleotide sequence shown in SEQ ID NO: 37 as a forward primer, an oligonucleotide consisting of the nucleotide sequence shown in SEQ ID NO: 38 as a reverse primer, and cDNA of *Xenopus laevis* brain as a template. The obtained DNA fragment was cloned into the plasmid pGEM-T Easy. The obtained clone was designated pGEM-T-xlKcnc2. The nucleotide sequence of the obtained clone was analyzed by using a DNA sequencer (3130 xl Genetic Analyzer, Applied Biosystems) according to the dideoxy terminator method, and it was confirmed that the nucleotide sequence as shown in SEQ ID NO: 31 was obtained. The nucleotide sequence shown in SEQ ID NO: 39 has an open reading frame consisting of 1716 base pairs. The amino acid sequence predicted from the open reading frame consists of 571 amino acid residues (SEQ ID NO: 40).

Example 11

Expression of *Xenopus Laevis* Kv3.2 Protein in *Xenopus Laevis* Oocyte

In order to detect the cation channel activity of a protein having the amino acid sequence shown in SEQ ID NO: 40, which activity changes according to the change of extracellular sodium ion concentration, cRNA was synthesized by using the clone obtained in Example 10 described above as a template, and injected into a *Xenopus laevis* oocyte, so that the protein was expressed. PCR was performed using the aforementioned plasmid pGEM-T-xlKcnc2 as a template, an oligonucleotide consisting of the nucleotide sequence shown in SEQ ID NO: 41 as a forward primer, and an oligonucleotide consisting of the nucleotide sequence shown in SEQ ID NO: 42 as a reverse primer. The obtained DNA fragment was digested with the restriction enzymes NheI and XhoI, and then cloned into the plasmid pcDNA3.1(+) (Invitrogen). The obtained clone was designated pcDNA3.1-xlKcnc2. The obtained plasmid was digested with the restriction enzyme XhoI at one site and thereby made linear, and then cRNA encoding the Kv3.2 protein was synthesized using a commercially available cRNA synthesis kit, Megascript High Yield Transcription Kit (Ambion). The synthesized cRNA was injected into a *Xenopus laevis* oocyte prepared in a conventional manner using a glass capillary and a microinjector (World Precision Instruments), so that the Kv3.2 protein was expressed. Furthermore, as a control cell, an oocyte into which water was injected was also prepared in the same manner. The obtained these oocytes were stored in a standard oocyte culture medium such as the ND96+ solution (96 mM NaCl, 2 mM KCl, 1 mM $MgCl_2$, 1.8 mM $CaCl_2$, 5 mM HEPES, 2 mM sodium pyruvate, 1/100 penicillin/streptomycin mixture (15140-122, Invitrogen), adjusted to pH 7.4 with NaOH) at 18° C. for two to four days, and then used in Examples 12 described below.

Example 12

Figure 6:
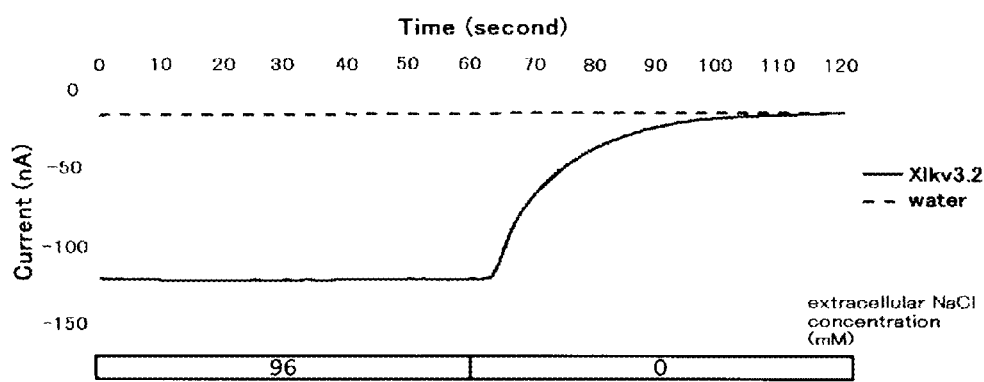
FIG. 6 shows cell membrane current observed for *Xenopus laevis* oocyte expressing a Kv3.2 protein (*Xenopus laevis*) when extracellular sodium ion concentration was changed. X1 Kv3.2 indicates injection of *Xenopus laevis* Kv3.2 cRNA.

Detection of Cation Channel Activity of *Xenopus Laevis* Kv3.2 Protein, which Changes According to Change of Extracellular Sodium Ion Concentration The total cell current was measured for each of the oocytes obtained in Example 11, of which membrane potential was clamped by the dual electrode voltage clamp method. For this measurement, the ND96 solution (96 mmol/L NaCl, 2 mmol/L KCl, 1 mmol/L $MgCl_2$, 1.8 mmol/L $CaCl_2$, and 5 mmol/L HEPES (pH 7.5)) was used. In the *Xenopus laevis* oocyte injected with cRNA prepared using the plasmid pcDNA3.1-xlKcnc2 as the template, an inward current higher than 100 nA was measured at a holding potential of −80 mV, when the NaCl concentration in the extracellular fluid was set to be 96 mM. When the NaCl concentration in the extracellular fluid was 0 mM, this current was not observed, and decrease in the current amount was observed with decrease of the extracellular sodium concentration (FIG. 6). On the other hand, in the control oocyte injected with water, such a significant inward current as described above was not observed at a holding potential of −80 mV, when the NaCl concentration in the extracellular fluid was set to be 96 mM, and change of the current amount was not also observed, even when the sodium ion concentration in the extracellular fluid was changed to 0 mM.

The above results demonstrated that the *Xenopus laevis* Kv3.2 protein could constitute a cation channel of which activity changes according to change of extracellular sodium ion concentration.

Example 13

Cloning of Mouse Kv3.2 Gene Expressed in Taste Buds

One kind of mouse Kv3.2 gene has been registered (SEQ ID NO: 9). As for human, four kinds of genes considered to be splice variants are registered at a gene database (SEQ ID NOS: 1, 3, 5 and 7) as Kv3.2 genes, and a plurality of splice variants may similarly exist for mouse. Therefore, for the purpose of obtaining Kv3.2 genes that were expressed and functioned in the mouse taste buds, mouse Kv3.2 genes were cloned from the tongue epithelium containing the taste buds. First, the epithelium was isolated from the tongue of mouse, a portion containing the taste buds was excised, and RNA was extracted using an RNA extraction kit (Absolutely RNA Microprep Kit, Stratagene). The extracted RNA was reverse-transcribed by using SuperScript III First Strand Synthesis System for RT-PCR (Invitrogen) to synthesize a first strand cDNA. By using the obtained first strand cDNA as a template, cDNA was amplified by PCR. As a forward primer, an oligonucleotide consisting of the nucleotide sequence shown in SEQ ID NO: 35 was used, and as a reverse primer, an oligonucleotide consisting of the nucleotide sequence shown in SEQ ID NO: 36, and oligonucleotides consisting of the nucleotide sequences shown in SEQ ID NOS: 43, 44 and 45, respectively, were used. The oligonucleotides consisting of the nucleotide sequences shown in SEQ ID NOS: 43, 44 and 45 were designed as reverse primers corresponding to mouse Kv3.2 splice variants expected from comparison of human Kv3.2 gene sequences (SEQ ID NOS: 1, 3, 5 and 7) and the mouse genomic DNA sequence containing the mouse Kv3.2 gene (GenBank accession number: NC_000076). For PCR, Phusion Hot Start High-Fidelity DNA Polymerase (New England Biolabs) was used.

Example 14

Splice Variants of Mouse Kv3.2 Gene Isolated From Taste Buds

The obtained DNA fragments were cloned into the plasmid pGEM-T Easy. The nucleotide sequences of the obtained 30 clones were analyzed using a DNA sequencer (3130 xl Genetic Analyzer, Applied Biosystems) according to the dideoxy terminator method, and they were roughly classified into 5 groups of similar kinds of nucleotide sequences. The five groups consisted of sequences having the same nucleotide sequence as that of SEQ ID NO: 9, which is uniquely registered at the gene database as the mouse Kv3.2 gene, and sequences having open reading frames shown in SEQ ID NOS: 46, 48, 50 and 52, respectively. The lengths of the nucleotide sequences and the lengths of the amino acid sequences predicted from the open reading frames (SEQ ID NOS: 47, 49, 51 and 53) are as shown in Table 6. These amino acid sequences have a common sequence except for the C terminal regions (part corresponding to the positions 1 to 597 of SEQ ID NO: 10), and they are considered as splice variants. These splice variants of the mouse Kv3.2 gene cloned from the taste buds may form a salty taste receptor channel by themselves or as a complex with another variant.

TABLE 6

|  | Nucleotide sequence | | Amino acid sequence | |
| --- | --- | --- | --- | --- |
|  | SEQ ID NO: | Sequence length | SEQ ID NO: | Sequence length |
| Mouse Kv3.2 | 9 | 1920 | 10 | 639 |
| Splice variant 1 | 46 | 1929 | 47 | 642 |
| Splice variant 2 | 48 | 1854 | 49 | 617 |
| Splice variant 3 | 50 | 1845 | 51 | 614 |
| Splice variant 4 | 52 | 1968 | 53 | 655 |

The invention claimed is:

1. A method of screening for a salty taste modulating substance, which comprises the step of contacting a test substance with a cell that expresses a Kv3.2 protein, and comparing observed cation influx into the cell with cation influx into the cell observed when the test substance is not contacted with the cell, wherein
   (a) when the cation influx is larger when the test substance is contacted with the cell that expresses a Kv3.2 protein as compared to when the test substance is not contacted with the cell that expresses a Kv3.2 protein, the test substance is correlated with enhancing salty taste, and
   (b) when the cation influx is smaller when the test substance is contacted with the cell that expresses a Kv3.2 protein as compared to when the test substance is not contacted with the cell that expresses a Kv3.2 protein, the test substance is correlated with inhibiting salty taste,
   wherein the Kv3.2 protein has a sequence identity of at least 95% to the sequence of SEQ ID NO: 6, and is able to constitute a cation channel of which activity changes according to change of extracellular sodium ion concentration.

2. The method according to claim 1, wherein the cation influx is measured by measuring cell membrane current of the cell in the presence of sodium ions.

3. The method according to claim 1, wherein the cation influx is measured by measuring cell membrane current of the cell in the absence of sodium ions.

4. The method according to claim 1 or 2, wherein the salty taste modulating substance is a salty taste enhancing substance or a salty taste inhibiting substance.

5. The method according to claim 1 or 3, wherein the salty taste modulating substance is a salt alternative substance.

6. The method according to claim 1, wherein the Kv3.2 protein has the amino acid sequence of SEQ ID NO: 2, 4, 6, 8, 12, or 49.

7. The method according to claim 1, wherein the Kv3.2 protein has the amino acid sequence of SEQ ID NO: 6 including substitutions, deletions, insertions and/or additions of 1 to 10 amino acid residues, and is able to constitute a cation channel of which activity changes according to change of extracellular sodium ion concentration.

8. The method according to claim 1, wherein the Kv3.2 protein is encoded by a DNA shown in the following (a) or (b):
   (a) a DNA having the nucleotide sequence of SEQ ID NO: 1, 3, 5, 7, 11 or 48;
   (b) a DNA which is able to hybridize with the nucleotide sequence complementary to the nucleotide sequence of SEQ ID NO: 5 or a probe which can be prepared from the nucleotide sequence complementary to the nucleotide sequence of SEQ ID NO: 5 under stringent conditions of 0.1×SSC, 0.1% SDS at 68° C., and codes for a protein that can constitute a cation channel of which activity changes according to change of extracellular sodium ion concentration.

9. The method according to claim 1, wherein the Kv3.2 protein is selected from Kv3.2 protein homologues derived from human, mouse or rat.

10. The method according to claim 1, wherein the cell is an oocyte into which a polynucleotide encoding a Kv3.2 protein is introduced in an expressible form.

11. The method according to claim 1, wherein the cell expresses a Kv3.2 gene isolated from a tissue selected from taste cell, tongue epithelium, adrenal gland, pineal body, thyroid, melanocyte and kidney.

12. The method according to claim 1, wherein the Kv3.2 protein shows a sequence identity of at least 97% to the sequence of SEQ ID NO: 6, and is able to constitute a cation channel of which activity changes according to change of extracellular sodium ion concentration.

13. The method according to claim 1, wherein the Kv3.2 protein shows a sequence identity of at least 99% to the sequence of SEQ ID NO: 6, and is able to constitute a cation channel of which activity changes according to change of extracellular sodium ion concentration.

14. The method according to claim 1, wherein the Kv3.2 protein has the amino acid sequence of SEQ ID NO: 2, 4, 6, 8, 12 or 49 including substitutions, deletions, insertions and/or additions of 1 to 5 amino acid residues, and is able to constitute a cation channel of which activity changes according to change of extracellular sodium ion concentration.

15. The method according to claim 1, wherein the Kv3.2 protein has the amino acid sequence of SEQ ID NO: 2, 4, 6, 8, 12 or 49 including substitutions, deletions, insertions and/or additions of 1 to 3 amino acid residues, and is able to constitute a cation channel of which activity changes according to change of extracellular sodium ion concentration.

* * * * *